(12) United States Patent
Beasley et al.

(10) Patent No.: US 9,644,203 B2
(45) Date of Patent: May 9, 2017

(54) METHOD OF PROTEIN DISPLAY

(71) Applicant: Affinity Biosciences Pty Ltd, Scoresby (AU)

(72) Inventors: Matthew Beasley, Fitzroy North (AU); Ben Kiefel, Mitcham (AU)

(73) Assignee: Affinity Biosciences Pty Ltd, Scoresby (AU)

( * ) Notice: Subject to any disclaimer, the term of this patent is extended or adjusted under 35 U.S.C. 154(b) by 653 days.

(21) Appl. No.: 14/142,298

(22) Filed: Dec. 27, 2013

(65) Prior Publication Data

US 2014/0121131 A1    May 1, 2014

Related U.S. Application Data

(63) Continuation of application No. PCT/AU2012/000761, filed on Jun. 28, 2012.

(30) Foreign Application Priority Data

Jun. 29, 2011   (AU) ................................ 2011902568

(51) Int. Cl.
  *C40B 30/04* (2006.01)
  *C12N 15/10* (2006.01)
  *C12N 15/70* (2006.01)
  *C12Q 1/02* (2006.01)

(52) U.S. Cl.
  CPC ..... *C12N 15/1055* (2013.01); *C12N 15/1034* (2013.01); *C12N 15/1037* (2013.01); *C12N 15/70* (2013.01); *C12Q 1/025* (2013.01); *C40B 30/04* (2013.01)

(58) Field of Classification Search
  None
  See application file for complete search history.

(56) References Cited

U.S. PATENT DOCUMENTS

| | | |
|---|---|---|
| 4,788,135 A | 11/1988 | Davis |
| 4,946,778 A | 8/1990 | Ladner et al. |
| 5,223,409 A | 6/1993 | Ladner et al. |
| 5,571,698 A | 11/1996 | Ladner et al. |
| 5,591,604 A | 1/1997 | Fuchs et al. |
| 5,837,500 A | 11/1998 | Ladner et al. |
| 6,818,418 B1 | 11/2004 | Lipovsek et al. |

(Continued)

FOREIGN PATENT DOCUMENTS

| | | |
|---|---|---|
| AU | 2003304195 | 7/2002 |
| AU | 2008243161 | 12/2008 |

(Continued)

OTHER PUBLICATIONS

International Search Report for International Patent Application No. PCT/AU2010/001702, filed Dec. 20, 2010. Received Feb. 23, 2011. 4 pages.

(Continued)

*Primary Examiner* — Christian Boesen
(74) *Attorney, Agent, or Firm* — Fish & Richardson P.C.

(57) ABSTRACT

The present invention relates to methods for screening a polypeptide for desired activity against a target molecule. In particular, the present invention relates to methods for screening a polypeptide for desired activity against a target molecule by expressing the polypeptide in a Gram-negative bacterial cell and permeabilising the cell. The invention also relates to methods of packaging gene libraries in a bacterial cell.

20 Claims, 25 Drawing Sheets

(56) References Cited

U.S. PATENT DOCUMENTS

Figure 1:
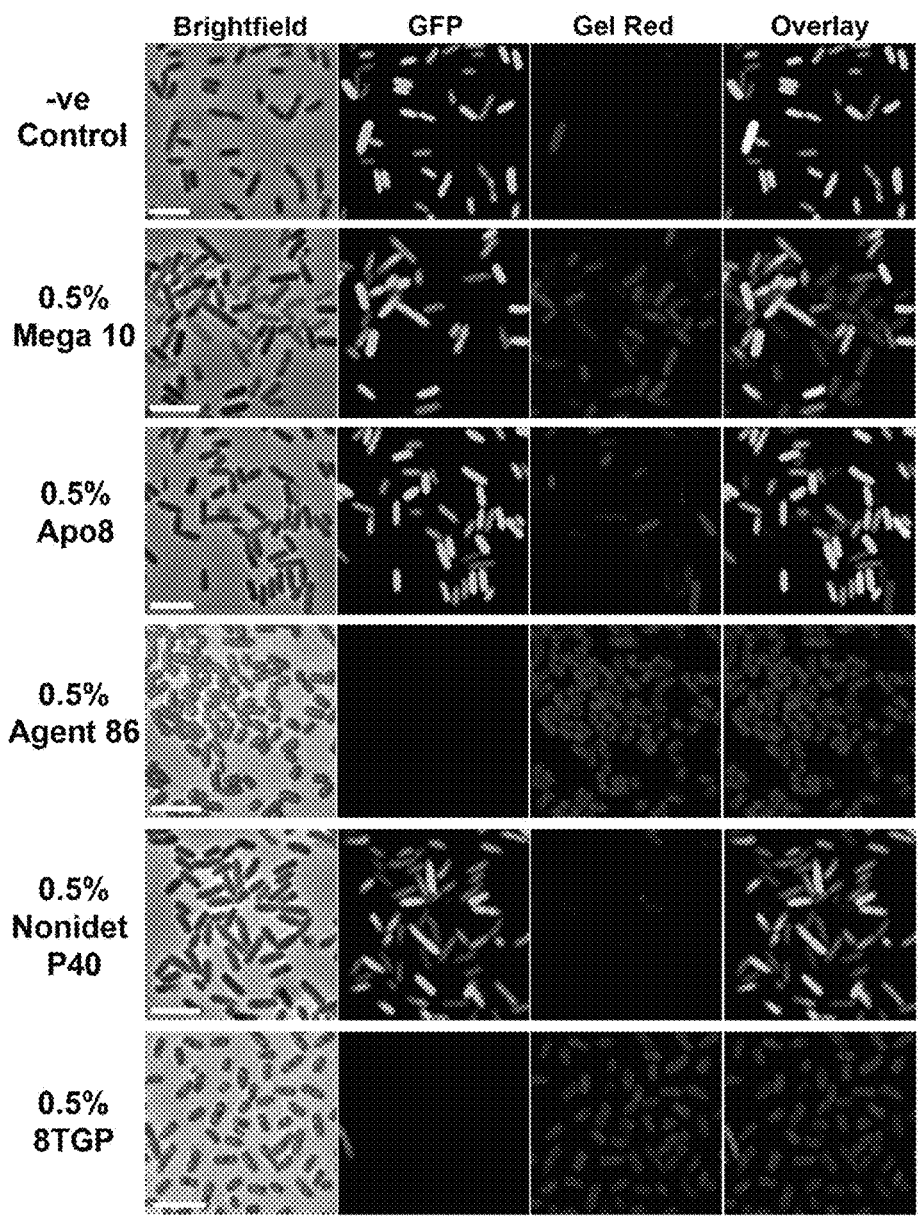

| | | |
|---|---|---|
| 6,916,474 B2 | 7/2005 | Harvey et al. |
| 7,083,945 B1 | 8/2006 | Chen et al. |
| 7,094,571 B2 | 8/2006 | Harvey et al. |
| 7,435,804 B2 | 10/2008 | Kordyum et al. |
| 7,611,866 B2 | 11/2009 | Georgiou et al. |
| 2003/0036092 A1 | 2/2003 | Iverson et al. |
| 2005/0147962 A1 | 7/2005 | Wagstrom |
| 2005/0267294 A1 | 12/2005 | Harvey et al. |
| 2006/0172379 A1 | 8/2006 | Teter et al. |
| 2007/0099267 A1 | 5/2007 | Harvey et al. |
| 2009/0005264 A1 | 1/2009 | Rakestraw et al. |
| 2009/0123921 A1 | 5/2009 | Georgiou et al. |
| 2009/0136936 A1 | 5/2009 | Georgiou et al. |
| 2009/0234101 A1 | 9/2009 | Ladner et al. |

FOREIGN PATENT DOCUMENTS

| | | |
|---|---|---|
| EP | 1279731 | 5/2007 |
| EP | 1820858 | 8/2007 |
| JP | 2004/531206 | 10/2004 |
| JP | 2006/507010 | 3/2006 |
| JP | 2007-121282 | 5/2007 |
| WO | WO92/15677 | 9/1992 |
| WO | WO02034886 A3 | 7/2003 |
| WO | WO2005/019409 | 3/2005 |
| WO | WO2005/074725 | 8/2005 |
| WO | WO2005/103074 | 11/2005 |
| WO | WO2005095988 A3 | 3/2006 |
| WO | WO2008/067547 | 6/2008 |
| WO | WO2008/074724 | 6/2008 |
| WO | WO2008/137475 | 11/2008 |

OTHER PUBLICATIONS

Extended European Search Report issued regarding European Patent Application No. EP10838401.7. Dated Nov. 12, 2013. 9 pages.

Communication pursuant to Article 94(3) EPC issued regarding European Patent Application No. EP10838401.7. Dated Oct. 7, 2015. 6 pages.

Australian Examination Report No. 1 issued against Australian Patent Application No. 2010336004. Issued on Dec. 5, 2014. 3 pages.

Chinese Office Action for Chinese Patent Application No. 201280041236.9. Dated Nov. 4, 2014. 14 pages.

Australian Examination Report No. 1 issued against Australian Patent Application No. 2012276282. Issued on Jun. 19, 2014. 5 pages.

Australian Examination Report No. 2 issued against Australian Patent Application No. 2012276282. Issued on Aug. 25, 2015. 3 pages.

Fuchs, P. et al. *Separation of E.coli expressing functional cell-wall bound antibody fragments by FACS*. Immunotechnology, vol. 2. Published Jun. 1996. pp. 97-102.

Georgiou, G. et al. *Display of β-lactamase on the Escherichia coli surface: outer membrane phenotypes conferred by Lpp'-OmpA'-β-lactamase fusions*. Protein Engineering, vol. 9, No. 2. Published Feb. 1996. pp. 239-247.

Japanese Office Action issued against Japanese Patent Application No. 2012-545011. Dated Mar. 10, 2015. 3 pages.

Japanese Office Action issued against Japanese Patent Application No. 2012-545011. Dated Nov. 4, 2015. 3 pages.

Ljungquist, E., et al., 'DNA Sequences of the Repressor Gene and Operator Region of Bacteriophage P2,' Proceedings of the National Academy of Sciences, 1984, vol. 81, pp. 39888-3992.

International Search Report for International Application No. PCT/AU2012/000761, mailed Oct. 11, 2012.

Breeuwer, P. et al. "Assessment of the membrane potential, intracellular pH and respiration of bacteria employing fluorescence techniques" Molecular Microbial Ecology Manual, Second Edition. 2004. 8.01: 1563-1580. MMEM-8.01/1563-MMEM-8.01/1579.

Chen, W. et al. "A simple and rapid method for the preparation of Gram-negative bacterial genomic DNA". Nucleic Acids Research, vol. 21, No. 9. Published May 11, 1993. p. 2260.

De Leij, F. et al. "Lac as a marker gene to track microbes in the environment" Molecular Microbial Ecology Manual, Second Edition. 2004. 6.01: 1187-1200. MMEM6.01/1187-MMEM-6.01/1199.

Devereux, R. et al. "Amplification of ribosomal RNA sequences". Molecular Microbial Ecology Manual, Second Edition. 2004. 3.01:509-522, MMEM-3.01/509-MMEM3.01/521.

Goldenberger, D. et al. "A simple 'universal' DNA extraction procedure using SDS and proteinase K is compatible with direct PCR amplification". PCR Methods Appl., vol. 4, Issue 6. Published Jun. 1995. pp. 368-370.

Harvey, B. et al. "Anchored periplasmic expression, a versatile technology for the isolation of high-affinity antibodies from *Escherichia coli*-expressed libraries" Proceedings of the National Academy of Sciences of the United States of America, vol. 101, No. 25. Published Jun. 22, 2004. pp. 9193-9198.

Insam, H. et al. "Use of Biolog® for the Community Level Physiological Profiling (CLPP) of environmental samples" Molecular Microbial Ecology Manual, Second Edition. 2004. 4.01: 853-860. MMEM-4.01/853-MMEM-4.01/560.

Moore, E., et al. "Simplified protocols for the preparation of genomic DNA from bacterial cultures" Molecular Microbial Ecology Manual, Second Edition. 2004. 1.01:3-18 MMEM-1.01/3-MMEM-1.01/17.

Paul, J. et al. "Natural transformation in aquatic environments" Molecular Microbial Ecology Manual, Second Edition. 2004. 5.01: 1047-1068. MMEM-5.01/1047-MMEM-5.01/1068.

Torsvik, Vigdis. "Quantification of nucleic acids". Molecular Microbial Ecology Manual, Second Edition. 2004. 2.01: 215-222. MMEM-2.01/215-MMEM-2.01/222.

Bershtein S., et al. *Advances in Laboratory Evolution of Enzymes*. Current Opinion in Chemical Biology, 12:151-158. Mar. 2008. 8 pages.

Skerlavaj et al. *Rapid Membrane Permeabilization and Inhibition of Vital Functions of Gram-Negative Bacteria by Bactenecins*. Infection and Immunity Nov. 1990. pp. 3724-3730.

Tracewell, C. et al. *Directed Enzyme Evolution: Climbing Fitness Peaks One Amino Acid at a Time*. Current Opinion in Chemical Biology, 13(1):3-9. Feb. 2009. 7 pages.

Aharoni et al., "High-Throughput Screening of Enzyme Libraries: Thiolactonases Evolved by Fluorescence-Activated Sorting of Single Cells in Emulsion Compartments," Chem Biol 2005, 12:1281-1289, 9 pages.

Barondess et al., "bor Gene of Phage λ, Involved in Serum Resistance, Encodes a Widely Conserved Outer Membrane Lipoprotein," J Bacteriology 1995, 177(5):1247-1253, 7 pages.

Becker et al., "Ultra-high-throughput screening based on cell-surface display and fluorescence-activated cell sorting for the identification of novel biocatalysts," Current Opinion in Biotechnology 2004, 15:323-329, 7 pages.

Bertani, "Abortive Induction of Bacteriophage P21," Virology 1968, 36:87-103, 17 pages.

Bradley et al., "Isolation of Phage P2-186 Intervarietal Hybrids and 186 Insertion Mutants," Molec Gen Genet 1975, 140:123-135, 13 pages.

Briani et al., "The Plasmid Status of Satellite Bacteriophage P4," Plasmid 2001, 45:1-17, 17 pages.

Briers et al., "The high-affinity peptidoglycan binding domain of Pseudomonas phage endolysin KZ144," Biochemical and Biophysical Research Communications 2009, 383:187-191, 5 pages.

Chang et al., "Incorporation of scaffolding protein gpO in bacteriophages P2 and P4," Virology 2008, 370:352-361, 10 pages.

Chen et al., "ComE, a Competence Protein from Neisseria gonorrhoeae with DNA-Binding Activity," J Bacteriology 2001, 183(10):3160-3168, 9 pages.

Cherepanov et al., "Gene disruption in *Escherichia coli*: TcR and KmR cassettes with the option of Flp-catalyzed excision of the antibiotic-resistance determinant," Gene 1995, 158:9-14, 6 pages.

Dai et al., "Using T7 phage display to select GFP-based binders," Protein Engineering, Design & Selection 2008, 21(7):413-424, 12 pages.

(56) References Cited

OTHER PUBLICATIONS

Daugherty et al., "Flow cytometric screening of cell-based libraries," J Immunol Methods 2000, 243:21-227, 17 pages.
Farinas, "Fluorescence Activated Cell Sorting for Enzymatic Activity," Combinatorial Chemistry & High Throughput Screening 2006, 9:321-328, 8 pages.
George et al., "An analysis of protein domain linkers: their classification and role in protein folding," Protein Engineering 2003, 15(11):871-879, 9 pages.
Gupta et al., "High-density Functional Display of Proteins on Bacteriophage Lambda," J Mol Biol 2003, 34:241-254, 14 pages.
Hamilton et al., "New Method for Generating Deletions and Gene Replacements in *Escherichia coli*," J Bacteriology 1989, 171(9):4617-4622, 6 pages.
Kahn et al., "Bacteriophage P2 and P4," Methods in Enzymology 1991, 204:264-280, 17 pages.
Karasawa et al., "A Green-emitting Fluorescent Protein from Galaxeidae Coral and Its Monomeric Version for Use in Fluorescent Labeling," J Biol Chem 2003, 278(36):34167-34171, 5 pages.
Kenrick et al, "Flow Cytometric Sorting of Bacterial Surface-Displayed Libraries," Current Protocols in Cytometry 2007, 4.6.1-4.6.27, 27 pages.
Kim et al., "Isolation and Characterization of the Smallest Bacteriophage P4 Derivatives Packaged into P4-Size Head in Bacteriophage P2-P4 System," J Microbiology 2006, 44(5):530-536, 7 pages.
King et al., "Nucleotide Sequence Analysis of in vivo Recombinants Between Bacteriophage λ DNA and pBR322," Mol Gen Genet 1982, 186:548-557, 10 pages.
Levy et al., "Isolation of trans-acting genes that enhance soluble expression of scFv antibodies in the *E. coli* cytoplasm by lambda phage display," J Immunological Methods 2007, 321:164-173, 10 pages.
Lindqvist et al., "Mechanisms of Genome Propagation and Helper Exploitation," Microbiological Reviews 1993, 57(3):683-702, 20 pages.
Lindqvist et al., "Peptide presentation by bacteriophage P4," FEMS Microbiology Reviews 1995, 17:33-39, 7 pages.
Liu et al., "Derepression of Prophage P2 by Satellite Phage P4: Cloning of the P4 e Gene and Identification of Its Product," J Virology 1997, 71(6):4502-4508, 7 pages.
Lutz et al., "Novel methods for directed evolution of enzymes: quality, not quantity," Current Opinion in Biotechnology 2004, 15:291-297, 7 pages.
Magnet et al., "Identification of the L,D-Transpeptidases Responsible for Attachment of the Braun Lipoprotein to *Escherichia coli* Peptidoglycan," J Bacteriology 2007, 189(10):3927-3931, 5 pages.
Maruyama et al., "λfoo: A λ phage vector for the expression of foreign proteins," Proc Natl Acad Sci 1994, 91:8273-8277, 5 pages.

Mikawa et al., "Surface Display of Proteins on Bacteriophage λ Heads," J Mol Biol 1996, 262:21-30, 10 pages.
Miller et al., "Directed evolution by in vitro compartmentalization," Nature Methods 2006, 3(7):561-570, 10 pages.
Montigiani et al., "Alanine Substitutions in Calmodulin-binding Peptides Result in Unexpected Affinity Enhancement," J Mol Biol 1996, 258:6-13, 8 pages.
Parsons et al., "Peptidoglycan Recognition by Pal, an Outer Membrane Lipoprotein," Biochemistry 2006, 45:2122-2128, 7 pages.
Rao et al., "Assembly of the Small Outer Capsid Protein, Soc, on Bacteriophage T4: A Novel System for High Density Display of Multiple Large Anthrax Toxins and Foreign Proteins on Phage Capsid," J Mol Biol 2007, 370:1006-1019, 14 pages.
Santini et al., "Efficient Display of an HCV cDNA Expression Library as C-terminal Fusion to the Capsid Protein D of Bacteriophage Lambda," J Mol Biol 1998, 282:125-135, 11 pages.
Sasaki et al., "Growth abnormalities in Hfr Derivatives of *Escherichia coli* Strain c," J gen Microbiol 1965, 40:365-376, 13 pages.
Sauer et al., "Interaction of Satellite Phage P4 with Phage 186 Helper," Virology 1982, 116:523-534, 12 pages.
Schaefer et al., "Construction of scFv Fragments from Hybridoma or Spleen Cells by PCR Assembly," Antibody Engineering 2010, 1:21-44, 24 pages.
Smith, "Filamentous Fusion Phage: Novel Expression Vectors That Display Cloned Antigens on the Virion Surface," Science 1985, 228:1315-1317, 3 pages.
Sternberg et al., "Display of peptides and proteins on the surface of bacteriophage λ," Proc Natl Acad Sci USA 1995, 92:1609-1613, 5 pages.
Vaccaro et al., "Efficient display of scFv antibodies on bacteriophage lambda," J Immunological Methods 2006, 310:149-158, 10 pages.
Wiman et al., "Genetic Map of *Escherichia coli* Strain C," Molec Gen Genetics 1970, 107:1-31, 31 pages.
Woods et al., "Prophage Induction of Noninducible Coliphage 186," J of Virology 1974, 14(6):1349-1356, 8 pages.
Yankovsky et al., "Phasmids as effective and simple tools for construction and analysis of gene libraries," Gene 1989, 81:203-210, 8 pages.
Younghusband et al., "Characterization of the DNA from Bacteriophage P2-186 Hybrids and Physical Mapping of the 186 Chromosome," Molec gen Genet 1975, 140:101-110, 10 pages.
Ziermann et al., "Functions Involved in Bacteriophage P2-Induced Host Cell Lysis and Identification of a New Tail Gene," J of Bacteriology 1994, 176(16):4974-4984, 11 pages.
Virta, M. et al "Real-time measurement of cell permeabilization with low-molecular-weight membranolytic agents." Journal of Anitmicrobial Chemotherapy, vol. 36, No. 2. Published Aug. 1, 1995. pp. 303-315.

METHOD OF PROTEIN DISPLAY

REFERENCE TO SEQUENCE LISTING

The present application is filed with a Sequence Listing in Electronic format. The Sequence Listing is provided as a file entitled 392190002001SequenceListing.txt, created Dec. 27, 2013, which is approximately 69 kb in size. The information in the electronic format of the sequence listing is incorporated herein by reference in its entirety.

FIELD OF THE INVENTION

The present invention relates to methods for screening a polypeptide for a desired activity against a target molecule. In particular, the present invention relates to methods for screening a polypeptide for a desired activity against a target molecule by expressing the polypeptide in a Gram-negative bacterial cell and permeabilising the bacterial cell. The invention also relates to methods of packaging gene libraries in a bacterial cell.

BACKGROUND OF THE INVENTION

The earliest method of protein display is phage display (Smith, 1985), in which the protein of interest is fused to one of the outer-coat proteins of the phage where it may be present along with wild-type copies of the protein. For example, a display platform based on the M13 filamentous phage using fusions to the gIII protein.

Other display methods include 'in vitro' display methods where the protein is expressed using a cellular translation extract, and the coupling between the protein and the coding nucleic acid is achieved through physical linkage (e.g. ribosome display, mRNA display) or through attachment to a common scaffold or encapsulation within a membrane, such as in in vitro compartmentalization (IVC) where the mRNA is translated within a micelle suspension that may also include a microbead (magnetic or sepharose) capture system for both mRNA and protein.

Another method of protein display is microbial surface display which involves the targeted location of expressed proteins to the exterior of a microbial cell, either Gram-negative or Gram-positive eubacteria or yeast. The proteins are fused to anchor domains that attach them to the cell surface. The anchor domains may have motifs dictating lipidation or covalent attachment to the cell wall, or they may be a fusion to an integral membrane protein within an exposed loop region. Due to the scalability of production, microbial surface display may not only be used for screening for improved protein variants from a diverse library, but may also be used to present antigens for vaccination or as a cellular-scaffold for enzymes for industrial biotechnology.

Protein display methods are commonly applied to the evolution of affinity proteins, such as antibodies. Single molecule display methods are historically the most popular, but they suffer from high background and low resolution between affinity scales. Antibodies identified by in vitro display or by phage systems are usually reformatted for expression in the *E. coli* periplasm, even though periplasmic yields are often extremely poor comparable to expression in the cytoplasm. When antibodies are expressed in the cytoplasm at high yield, however, in almost every instance they form insoluble inclusion bodies that must be laboriously refolded and tested for activity.

Thus, there remains a need for methods of protein display, particularly for the screening of affinity protein display libraries and enzyme libraries.

SUMMARY OF THE INVENTION

The present inventors have developed a protein display method in which a polypeptide being screened for a desired activity is produced in the cytoplasm of a Gram-negative bacterial cell, and the polynucleotide encoding the polypeptide is packaged within a lysis-defective phage that is also retained within the bacterial cell. One or more of the bacterial cell membranes are permeabilised, whereby the bacterial cell can be contacted with a target molecule in order to screen for the desired activity.

Accordingly, the present invention provides a method of screening a polypeptide for a desired activity against a target molecule, the method comprising:

a) culturing a Gram-negative bacterial cell comprising an exogenous polynucleotide encoding the polypeptide such that the polypeptide is produced in the cell, b) allowing a lysis-defective phage to package the polynucleotide encoding the polypeptide, wherein the lysis-defective phage is retained within the bacterial cell, c) permeabilising:
  i) the outer membrane of the bacterial cell, or
  ii) the inner and outer membranes of the bacterial cell, d) contacting the bacterial cell with the target molecule, and e) screening the polypeptide for the desired activity, wherein the polypeptide is retained within the bacterial cell by the bacterial cell wall or inner membrane and/or the polypeptide is attached to the bacterial cell wall or inner membrane.

In one embodiment, the polypeptide may be expressed and retained within the cytoplasm of the bacterial cell by the bacterial cell wall. Thus, in one embodiment, the method comprises permeabilising the inner and outer membranes of the bacterial cell.

The polypeptide may be of sufficient size such that it is retained within the bacterial cell comprising permeabilised inner and outer membranes by the intact cell wall. Alternatively, if the polypeptide is sufficiently small in size it may diffuse through the intact cell wall. In order to prevent the polypeptide diffusing through the cell wall, in one embodiment the polypeptide is associated with at least a second polypeptide to form a protein complex that is retained within the permeabilised bacterial cell and/or is attached to the bacterial cell wall. In one embodiment, the polypeptide is fused to the second polypeptide or a subunit thereof.

In one particular embodiment, the second polypeptide is selected from:

i) a polypeptide having a molecular size such that the protein complex is retained inside the permeabilised bacterial cell wall;

ii) a DNA-binding protein;

iii) a bacterial cell wall-binding protein; and/or iv) a phage coat protein of the lysis-defective phage.

While any suitable method may be used to permeabilise the inner and outer bacterial membranes, in one embodiment, the inner and outer bacterial membranes are permeabilised with one or more detergents or an organic solvent.

In one embodiment, the one or more detergents is a non-ionic detergent.

In another embodiment, the non-ionic detergent is selected from Decanoyl-N-methylglucamide (Mega10), demithyloctylphosphine oxide (Apo8), n-octyl-β-D-thioglucopyranoside (8TGP), and a mixture of Decanoyl-N-methylglucamide (Mega10) and demihyloctylphosphine oxide (Apo8).

Alternatively, the inner and outer membranes of the bacterial cell may be permeabilised with an organic solvent such as chloroform. For example, in one embodiment, the inner and outer membranes of the bacterial cell are permeabilised by incubating the bacterial cell in an aqueous solution saturated with chloroform.

In one particular embodiment, the bacterial cell is incubated in the aqueous solution saturated with chloroform for about 10 minutes at about 25° C.

In another embodiment of the invention, the polypeptide is produced in the bacterial cell and attached to the inner membrane of the bacterial cell. Thus, the outer membrane of the bacterial cell is permeabilised and the cell wall is at least partially hydrolysed, while the inner membrane is left intact.

Accordingly, in one embodiment of the method of the invention:
  i) the bacterial outer membrane is permeabilised;
  ii) the bacterial cell wall is at least partially hydrolysed; and
  iii) the polypeptide is attached to the inner membrane.

In one particular embodiment, the bacterial cell wall is at least partially hydrolysed with lysozyme.

In a further embodiment, the polypeptide is fused to a protein that attaches to the inner membrane. In one particular embodiment, the polypeptide is attached to the outer face of the inner membrane.

In yet another embodiment, the polypeptide is associated with a bacteriophage coat protein. In one particular embodiment, the polypeptide is fused to either end of the lambda bacteriophage capsid protein, gpD. In another embodiment, the polypeptide is fused to the N-terminal end of the P2 bacteriophage capsid protein, gpL.

The DNA encoding the polypeptide may be genomic DNA and/or episomal DNA. In one embodiment, the polynucleotide encoding the polypeptide is a plasmid, cosmid, phagemid or phage DNA.

In one embodiment, the lysis-defective phage is a temperate phage selected from lambda phage, 186, P2, a hybrid of 186 and P2, and/or P4.

The lysis-defective phage may be present in the Gram-negative bacterial cell as a phage or integrated into the host cell genome as a prophage. Thus, in one embodiment, the lysis-defective phage is a prophage.

In one particular embodiment, the bacterial cell comprises lysis-defective lambda, 186, P2, a hybrid of 186 and P2, and/or P4 prophage.

In another embodiment, the bacterial cell comprises P2 and P4 prophage.

In one particular embodiment, the bacterial cell comprises lambda prophage.

In yet another embodiment, the bacterial cell comprises a hybrid of 186 and P2 prophage.

In one embodiment, allowing the lysis-defective phage to package the polynucleotide encoding the polypeptide comprises inducing activation of the prophage in the bacterial cell to produce phage, wherein the phage package the polynucleotide.

In one embodiment, inducing activation of the prophage comprises producing one or more phage activator proteins in the bacterial cell.

In one particular embodiment, the bacterial cell comprises P2 and P4 prophages and the method comprises producing P2 and/or P4 activator proteins in the bacterial cell.

In one embodiment, the P2 and/or P4 activator proteins are selected from one or more of P2 cox, P2 ogr, P4 δ and/or P4ε.

In another embodiment, inducing activation of the prophage comprises inactivating one or more phage repressor proteins in the bacterial cell.

In one embodiment, the bacterial cell comprises P2 and/or P4 prophage and inducing activation of P2 prophage comprises inactivating a temperature-sensitive repressor allele of P2 protein C in the bacterial cell.

In one embodiment, the bacterial cell comprises lambda prophage and inducing activation of the lambda prophage comprises inactivating a temperature-sensitive repressor allele of lambda phage repressor protein cI in the bacterial cell.

In another embodiment, the bacterial cell comprises 186 prophage and inducing activation of the 186 prophage comprises inactivating a temperature-sensitive repressor allele of 186 protein cI in the bacterial cell.

In another embodiment, the bacterial cell comprises a hybrid of 186 and P2 prophage and inducing activation of prophage comprises inactivating a temperature-sensitive repressor allele of the hybrid phage in the bacterial cell.

In yet another embodiment, the prophage is lysis-defective due to deletion or mutation to an inactive form of either of the lysozyme or holin genes, or deletion or mutation to an inactive form of both the holin and lysozyme genes. In one particular embodiment, the P2 prophage lysozyme gene comprises a sequence of nucleotides comprising SEQ ID NO:17 and the P2 holin gene comprises a sequence of nucleotide comprising SEQ ID NO:18. In another embodiment, the lambda prophage holin gene comprises a sequence of nucleotides comprising SEQ ID NO:23 and the lambda lysozyme gene comprises a sequence of nucleotides comprising SEQ ID NO:24.

In another embodiment, inducing activation of the prophage comprises increasing the incubation temperature of the bacterial cells. In one particular embodiment, the incubation temperature of the bacterial cells is increased from about 30° C. to about 42° C. to induce activation of the prophage. In one embodiment, the prophage is lambda phage. In another embodiment, the prophage is 186 or a hybrid of 186 and P2 prophage.

The person skilled in the art will understand the method of the present invention may be used together with other known phage display systems. In contrast to the present invention, known phage display systems do not package the polynucleotide encoding the polypeptide into a lysis-defective phage and/or do not retain the polypeptide within the bacterial cell or attached to the bacterial cell wall or cell membranes.

Accordingly, in one embodiment, the method further comprises an additional screening of the polypeptide for a desired activity against a target molecule in a Gram-negative bacterial cell, wherein
  i) the polynucleotide encoding the polypeptide is not packaged into a lysis-defective phage, and/or
  ii) the polypeptide is not retained within the bacterial cell by the bacterial cell wall and/or attached to the bacterial cell wall.

While the additional screening using a known phage display system may be performed prior to and/or after the method of the invention, in one embodiment the additional screening is performed prior to the method of the invention.

In one embodiment, the phage in the additional screening is performed using a lytic phage or temperate phage to package the polynucleotide encoding the polypeptide.

In another embodiment, the bacterial cell in the additional screening is lysed to release the phage.

In yet another embodiment, the phage in the additional screening is a lytic phage which lyses the bacterial cell.

Where the bacterial cell is lysed during the additional screening, it is desirable to attach the polypeptide to the phage particle.

Thus, in one embodiment:

i) the lytic phage comprises a first binding partner on the phage coat, and ii) the polypeptide being screened for a desired activity is a fusion protein comprising a second binding partner, wherein the fusion protein comprising the second binding partner binds to the first binding partner on the lambda phage coat.

In one embodiment, the lytic phage is lambda phage.

In another embodiment, the lytic phage is 186, P2, a hybrid of 186 and P2 prophage, and/or P4.

In one embodiment, the first binding partner is calmodulin and the second binding partner is calmodulin-binding peptide.

In yet another embodiment, the one or more prophages in the additional screening is a lysis-defective phage and the cells are lysed chemically and/or enzymatically. In one particular embodiment, enzymatically lysing the cells comprises lysing the bacterial cells with lysozyme. The lysis-defective phage may be, for example, lysis-defective lambda, 186, P2, a hybrid of 186 and P2 prophage, and/or P4.

While the method of the invention may be used to package any gene library, in one embodiment, the library of polynucleotides encodes polypeptides to be screened for a desired activity against a target molecule.

The present invention further provides a Gram-negative bacterium comprising a lysis-defective phage with a temperature-sensitive repressor protein.

The present invention further provides a Gram-negative bacterium comprising a lysis-defective phage and a polynucleotide encoding one or more phage activator proteins.

In one embodiment, the lysis-defective phage is selected from lambda, 186, P2, a hybrid of 186 and P2 and/or P4.

In an embodiment, the phage activator proteins are selected from P2 cox, P2 ogr, P4 δ and/or P4 ε.

The present invention further provides a kit comprising the Gram-negative bacterium of the invention.

In one embodiment, the kit further comprises an agent capable of permeabilising the Gram-negative bacterial cell. In one particular embodiment, the agent capable of permeabilising the Gram-negative bacterial cell is selected from one or more detergents or an organic solvent.

In an embodiment, the detergent is a non-ionic detergent selected from Decanoyl-N-methylglucamide (Mega10), demithyloctylphosphine oxide (Apo8), n-octyl-β-D-thioglucopyranoside (8TGP), polysorbate 20 (Tween20), and a mixture of Decanoyl-N-methylglucamide (Mega10) and demithyloctylphosphine oxide (Apo8).

In another embodiment, the organic solvent is chloroform.

The present invention further provides a method of screening a polypeptide for a desired activity against a target molecule, the method comprising:

a) culturing a Gram-negative bacterial cell comprising a polynucleotide encoding the polypeptide such that the polypeptide is produced, b) permeabilising the inner and outer membranes of the bacterial cell with chloroform, wherein the polypeptide and polynucleotide encoding the polypeptide are retained inside the permeabilised bacterial cell, c) contacting the permeabilised bacterial cell with the target molecule such that it diffuses into the permeabilised bacterial cell, and d) screening the polypeptide for the desired activity.

The present invention further provides a method of screening a polypeptide for a desired activity against a target molecule, the method comprising:

a) culturing a Gram-negative bacterial cell comprising a polynucleotide encoding the polypeptide such that the polypeptide is produced and attaches to the bacterial cell wall, b) permeabilising the inner and outer membranes of the bacterial cell with chloroform, wherein the polynucleotide encoding the polypeptide is retained inside the permeabilised bacterial cell, c) contacting the permeabilised bacterial cell with the target molecule, and d) screening the polypeptide for the desired activity.

In one embodiment, step d) comprises:

i) determining if the polypeptide binds, and/or the extent of binding to, the target molecule, and/or ii) determining if the polypeptide enzymatically modifies, and/or the rate of enzymatic modification of, the target molecule.

In one embodiment, the polypeptide is associated with at least a second polypeptide to form a protein complex that is retained inside the permeabilised bacterial cell and/or attached to the bacterial cell wall.

In one embodiment, the polypeptide is fused to the second polypeptide, or a subunit thereof.

In the method of the invention, the second polypeptide may be selected from:

i) a polypeptide having a molecular size such that the protein complex is retained inside the permeabilised bacterial cell wall;

ii) a DNA-binding protein;

iii) a bacterial cell wall-binding protein, and/or iv) a phage coat protein.

The present invention further provides a method for identifying a polypeptide with a desired activity, the method comprising:

a) screening a library of polypeptides using a method of the invention; and b) selecting one or more polypeptides with the desired activity.

The present invention further provides a Gram-negative bacterial cell obtained by permeabilising the inner and outer membranes of the bacterial cell with chloroform, wherein the bacterial cell comprises an exogenous polypeptide associated with a second polypeptide to form a protein complex that is retained inside the permeabilised bacterial cell.

The present invention further provides a Gram-negative bacterial cell obtained by permeabilising the inner and outer membranes of the bacterial cell with chloroform, wherein the bacterial cell comprises an exogenous polypeptide attached to the bacterial cell wall.

The present invention further provides a kit comprising:

a) a vector comprising i) a site for inserting into the vector a polynucleotide encoding a first polypeptide, and ii) an open reading frame encoding a second polypeptide which associates with the first polypeptide to form a protein complex that is retained inside a permeabilised Gram-negative bacterial cell, and b) chloroform for permeabilising a bacterial cell.

The present invention further provides a kit comprising:
a) a vector comprising
   i) a site for inserting into the vector a polynucleotide encoding a first polypeptide, and
   ii) an open reading frame encoding a second polypeptide which associates with the first polypeptide to form a protein complex that attaches to a Gram-negative bacterial cell wall, and
b) chloroform for permeabilising a bacterial cell.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Detergent permeabilisation of E. coli cells. E. coli cells expressing GFP were treated with detergents to determine the effectiveness of membrane permeabilisation. Cells were viewed by either brightfield (first column) or fluorescence microscopy (second and third columns). Permeabilisation was effective if GFP (column 2) was released from the cell concurrent with uptake of the membrane-impermeable DNA-binding dye, Gel Red (third column) Detergents 8TGP (0.5%) and 0.5% Mega10/0.5% Apo 8 ('Agent86') were found to be most effective in permeabilising E. coli cells.

Figure 2:
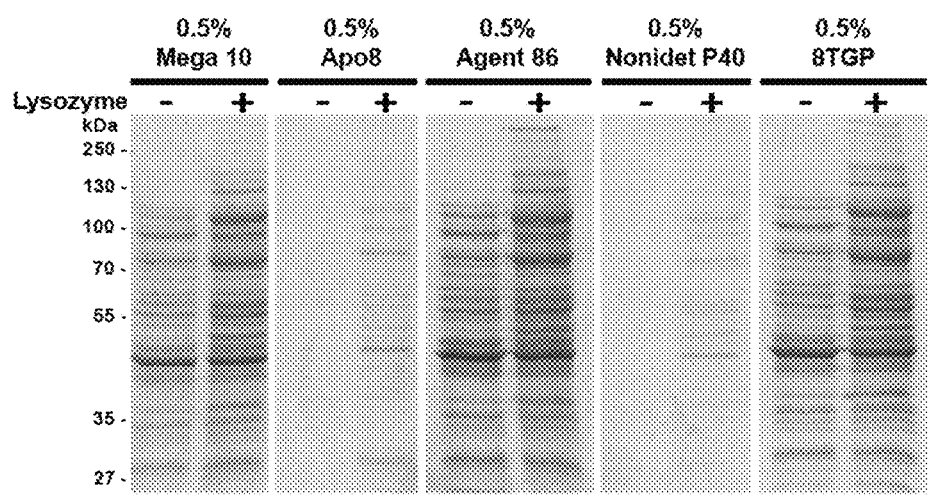

FIG. 2. SDS-PAGE of detergent supernatants. The supernatant of the detergent permeabilisation of E. coli cells shown in FIG. 1 were loaded onto a 9% SDS-PAGE to qualitatively judge protein release by the detergents (first lane). To demonstrate retention of a subset of cellular proteins by the cell wall capsule in detergent permeabilised cells, a sample of detergent permeabilised cells was treated with lysozyme (2 mg/mL) to hydrolyse the cell wall (second lane).

Figure 3:
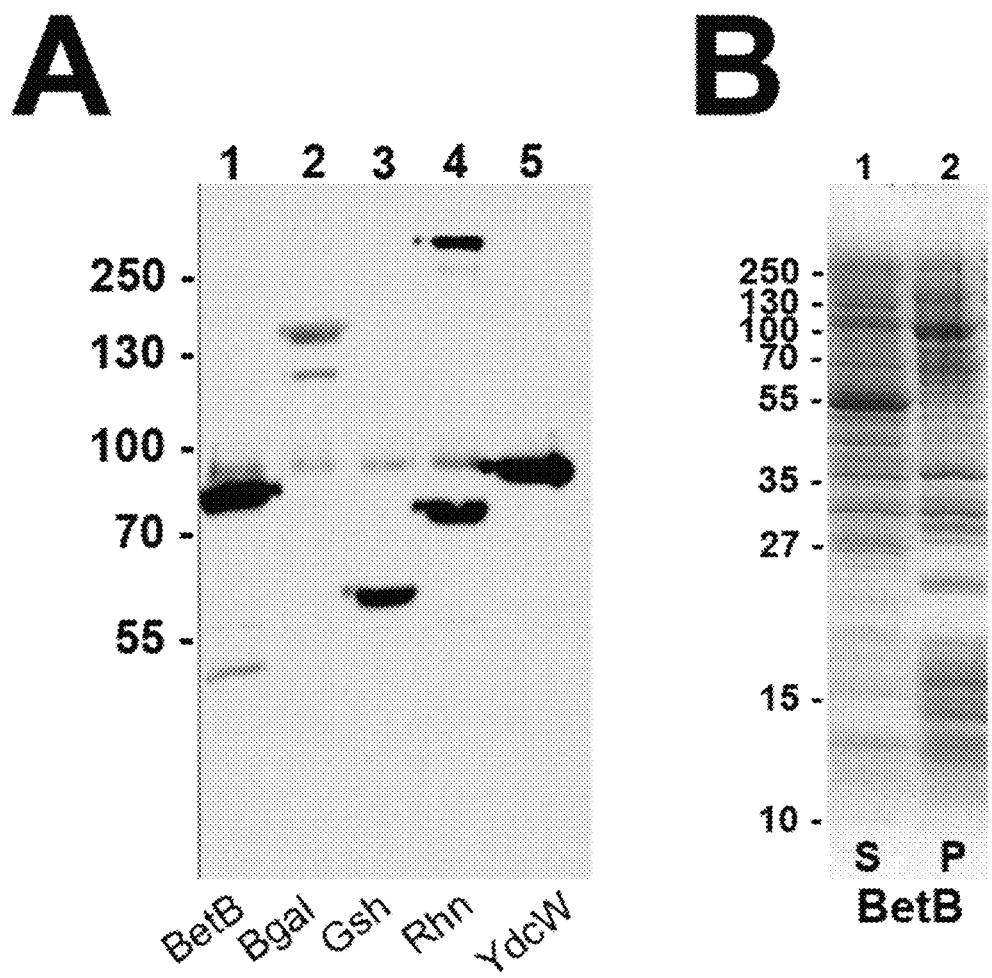

FIG. 3. Tetrameric-fusion protein expression. (A) Expression of His 6::SNAP::tetramer fusion proteins in E. coli was examined by Western blot using an αHis antibody probed against total cellular protein. A high-molecular weight band of >250 kD was observed in the RhnA tetramer fusion (lane 4), in addition to a band of the expected molecular weight, which is a presumptive SDS-resistant form of the complex that migrated as a tetramer. (B) The BetB tetrameric fusion protein extract was separated into the detergent-soluble and detergent-insoluble (cell capsule pellet) extracts, and examined by SDS-PAGE.

Figure 4:
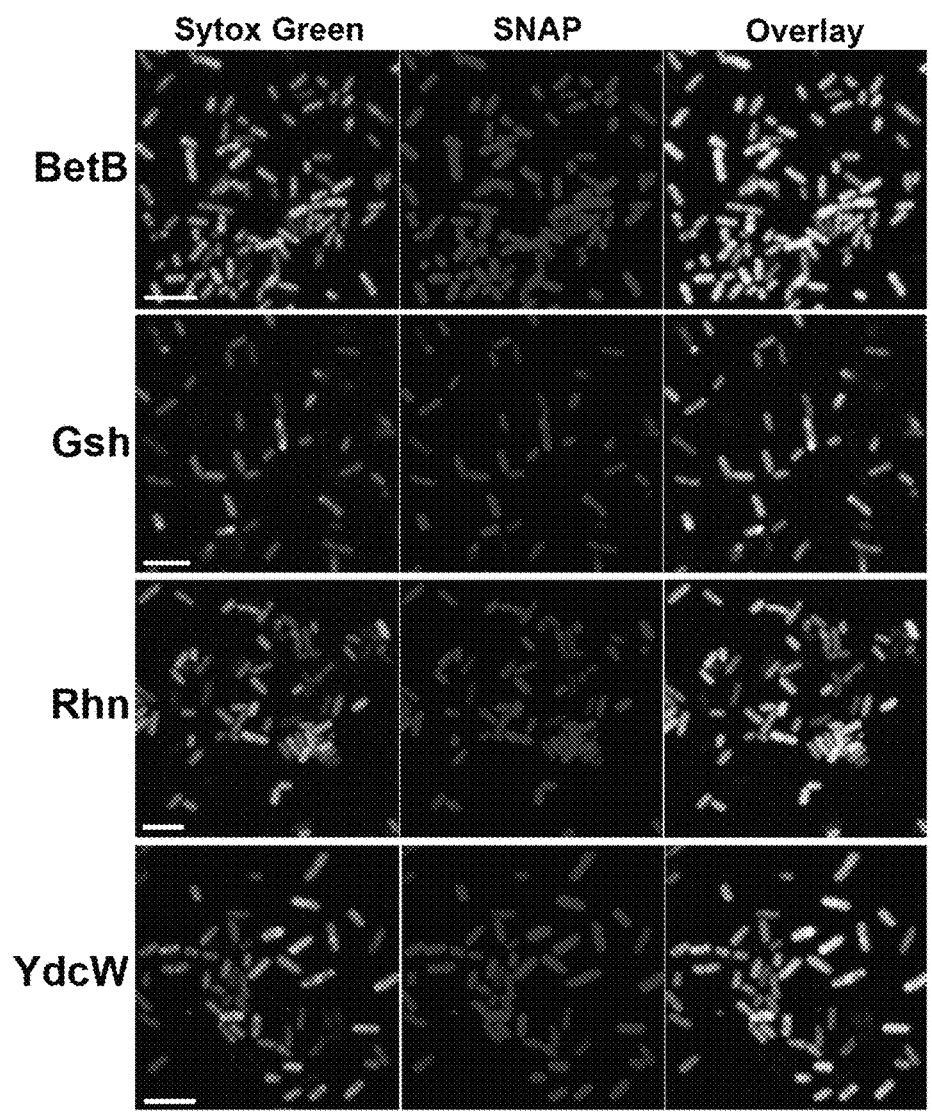

FIG. 4. SNAP labeling of tetramer-fusion proteins. The His 6::SNAP::tetramer fusion proteins were expressed in E. coli, and the cells were permeabilised with 8TGP, as described by Example 1. Expression of the fusion protein was detected by fluorescence microscopy of permeabilised cells labeled with the membrane-impermeable SNAP ligand BG-547 (second column), as described in Example 3. Cellular DNA was labeled with the membrane-permeable dye, Sytox Green (first column). The overlay of the SNAP and Sytox Green signal is presented in the third column.

Figure 5:
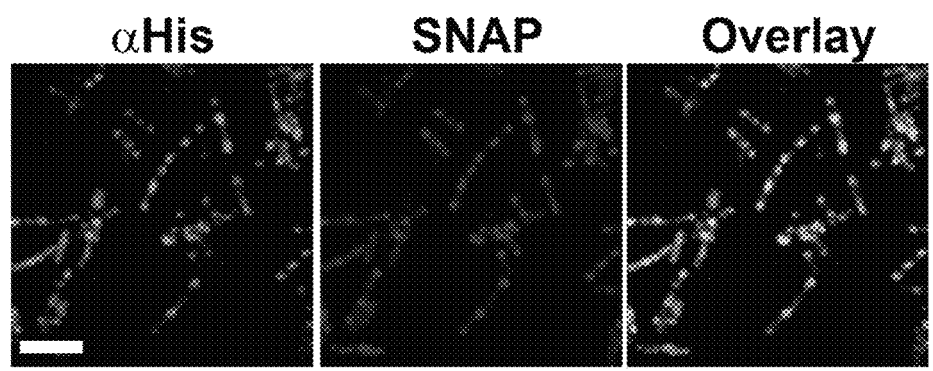

FIG. 5. αHis antibody labeling of His6::SNAP::BetB tetramer in permeabilised cells. Fluorescence microscopy of permeabilised cells expressing the His6::SNAP::BetB tetramer probed with an αHis antibody (first panel), as described in Example 3. Cells were labeled with the SNAP ligand BG-547 (second panel). The co-localisation of both αHis and SNAP (third panel) indicates that the αHis antibody penetrated through the cell wall of permeabilised cells.

Figure 6:
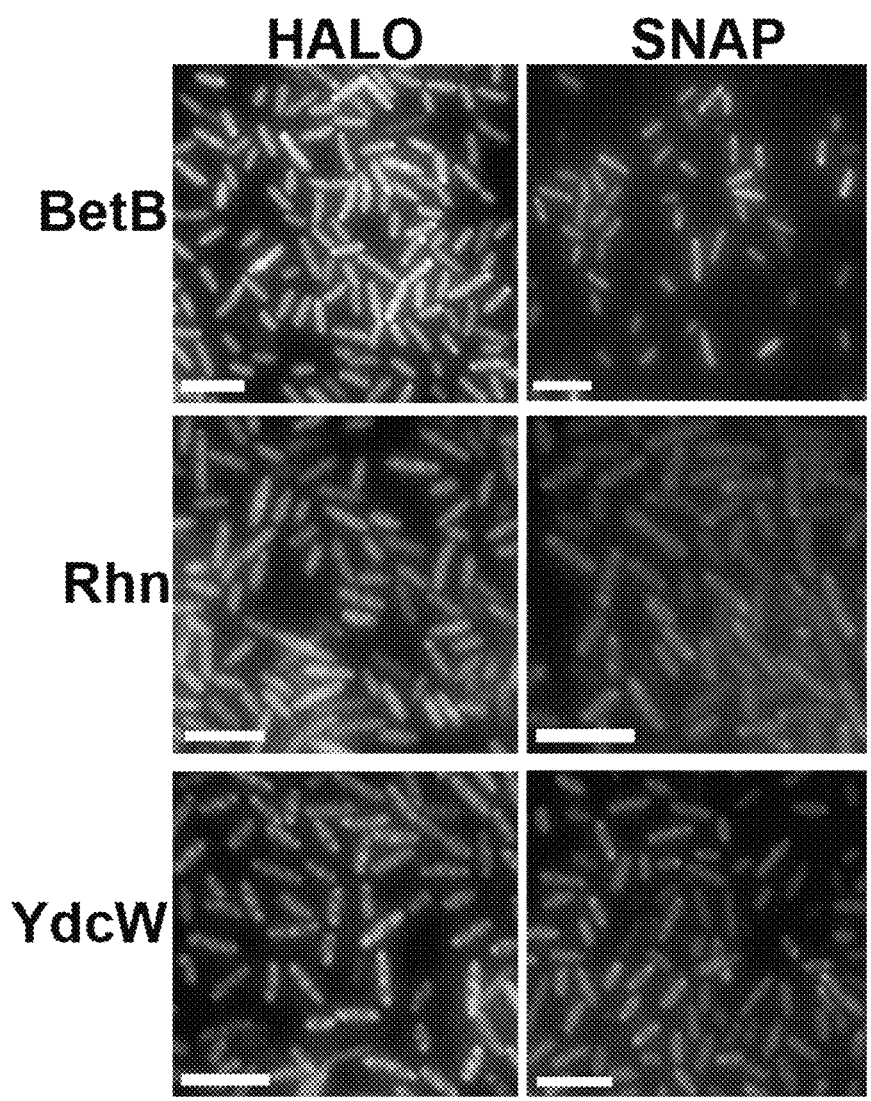

FIG. 6. BetB, RhnA and YdcW tetramer fusions with HALO and SNAP expression reporters. The BetB, RhnA and YdcW tetramers were separately fused to the expression reporters, HALO and SNAP. Cells expressing the fusion protein were permeabilised and the host DNA was labeled with Gel Red and the fusion protein was detected using the fluorescent ligands for HALO (G1001) and SNAP (BG-488).

Figure 7:
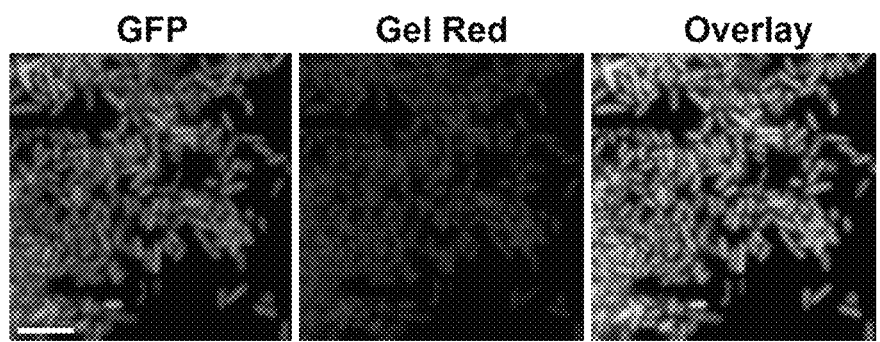

FIG. 7. Expression of the GFP5::DNA Binding Protein (DBP) fusion. The non-specific, high-affinity, DNA binding protein, ComE, from N. gonorrhoeae was fused to the C-terminus of GFP5 and expressed in E. coli. Cells were permeabilised and viewed by fluorescence microscopy for GFP (first panel) and Gel Red (second panel). Co-localisation (third panel) of the fluorescence indicates that both the fusion protein and host DNA were retained within the permeabilised cell capsule.

Figure 8:
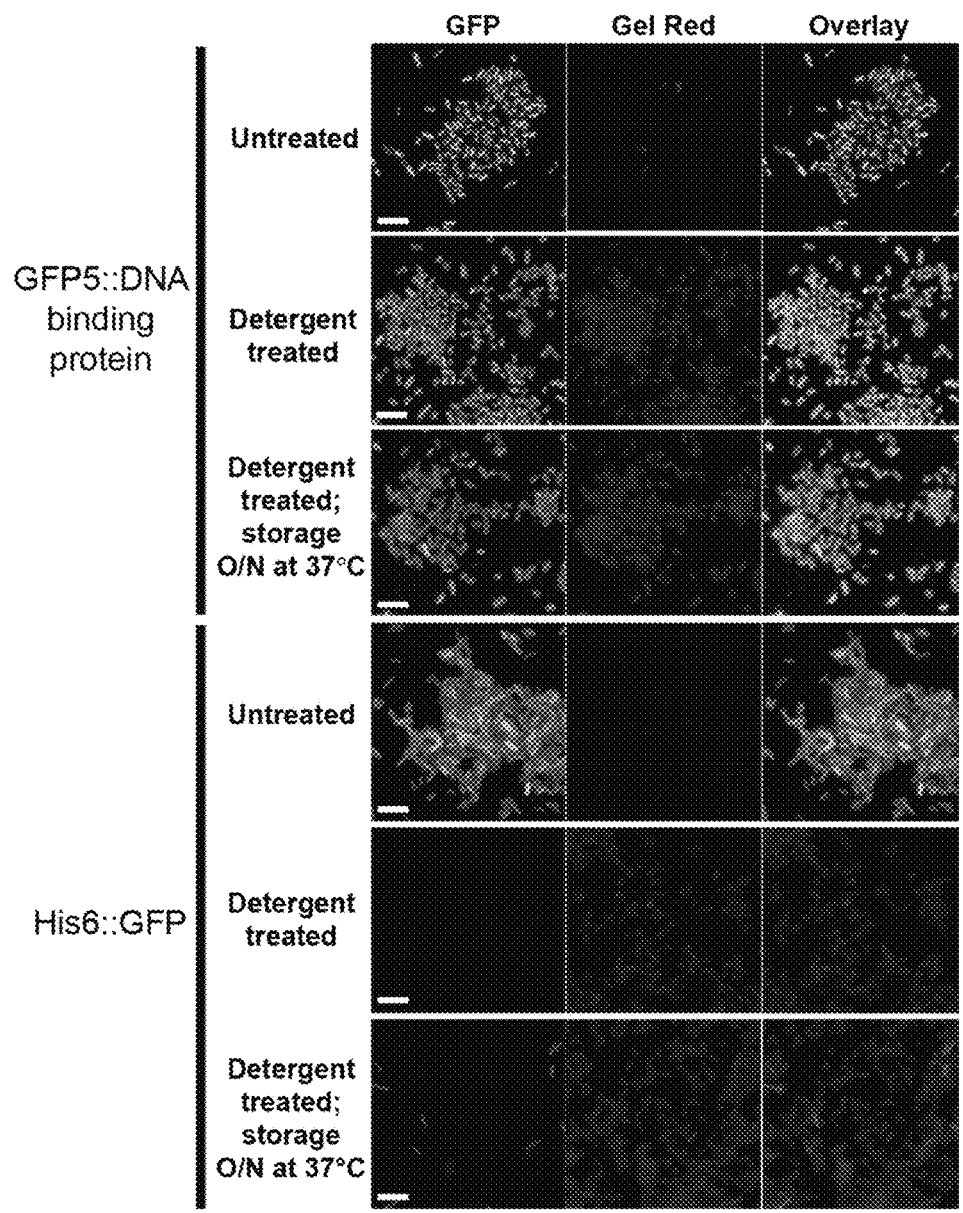

FIG. 8. Retention of DNA in permeabilised cells. E. coli cells expressing the GFP5::DBP fusion, or a His6::eGFP fusion were either left untreated (rows 1 and 4) or were permeabilised (rows 2, 3, 5 and 6) as described in Example 1. Permeabilised cells were either stored overnight at 4° C. or resuspended in TBS and shaken overnight at 37° C. before being viewed by fluorescence microscopy for GFP (first column) or Gel Red (second column) Co-localisation of GFP and Gel Red is presented in the third column.

Figure 9:
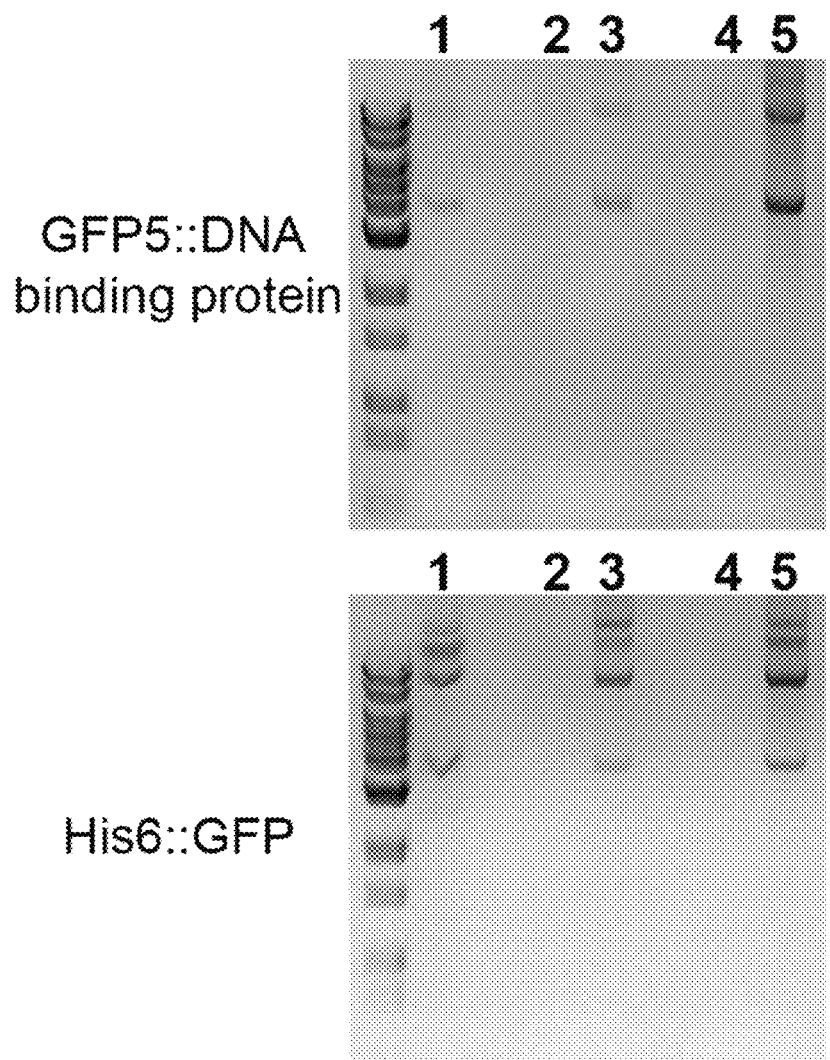

FIG. 9. DNA extraction from permeabilised cells. E. coli cells expressing (top panel) GFP5::DBP or (bottom panel) His6::eGFP fusion proteins were permeabilised as described in Example 1. Permeabilised cells were stored overnight at 4° C. or resuspended in TBS and shaken overnight at 37° C. before plasmid DNA was extracted and electrophoresed on an ethidium-bromide stained 1% agarose gel with TAE buffer. Lane 1 is the total plasmid DNA in untreated cells. Lanes 2 and 4 are the supernatants from the permeabilisation step of cell capsules stored overnight at 4° C. and shaking at 37° C., respectively, and lanes 3 and 5 are plasmid preparations from the cell capsules stored overnight at 4° C. and shaking at 37° C., respectively.

Figure 10:
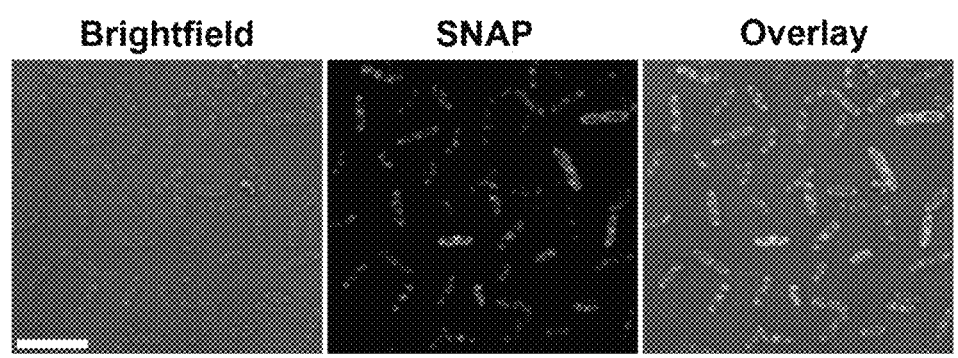

FIG. 10. SNAP labeling of the OmpF::SNAP::LPP fusion protein. E. coli cells expressing the OmpF::SNAP::LPP fusion protein were permeabilised as described in Example 1. Fusion protein localization was detected by labeling with the SNAP ligand BG-488 as described in Example 3. Labeled cells were viewed by brightfield microscopy (first panel) and by fluorescence microscopy (second panel). The third panel is the overlay of both brightfield and fluorescent views.

Figure 11:
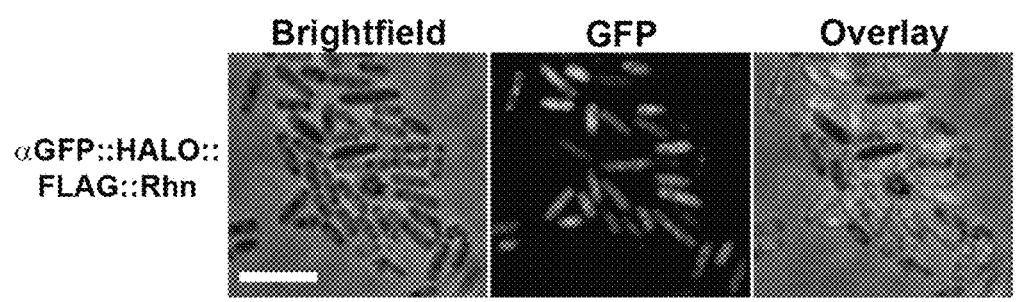

FIG. 11. Binding of eGFP by αGFP::HALO::RhnA fusion protein. E. coli cells expressing the αGFP::HALO::RhnA fusion protein were permeabilised as described in Example 1. Purified eGFP protein was bound to the cell capsules as described in Example 8 and eGFP was visualized by fluorescence microscopy. First panel, brightfield view; second panel, eGFP fluorescence; third panel, overlay of brightfield and fluorescence.

Figure 12:
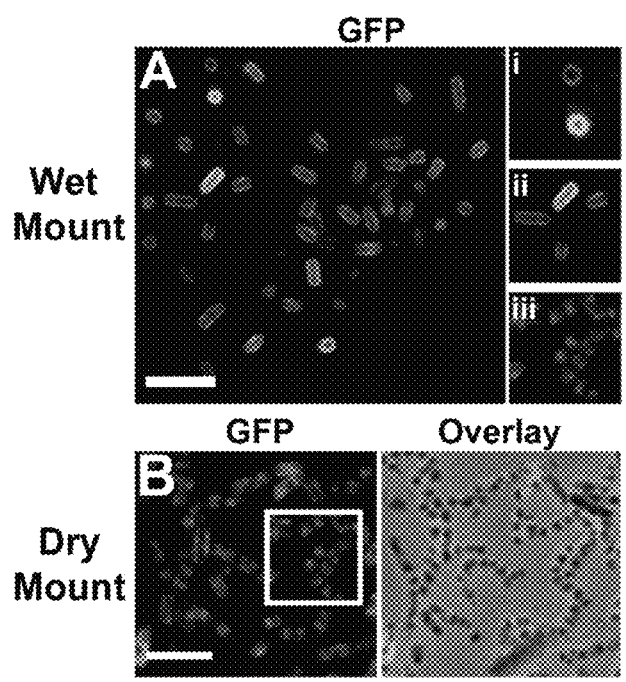

FIG. 12. Binding of eGFP by αGFP::KzPG::SNAP::DBP fusion protein. E. coli cells expressing the αGFP::KzPG::SNAP::DBP fusion protein were permeabilised as described in Example 1. Purified eGFP protein was bound to the cell capsules as described in Example 8 and eGFP was visualized by fluorescence microscopy by two methods, wet mount and dry mount, as described in Example 3. (A) eGFP bound to wet-mounted cell capsules. Inset panels (i) and (ii) show the cell-wall localization of the eGFP bound by the αGFP::KzPG::SNAP::DBP fusion protein. (B) and inset panel (Aiii) show the same cells prepared for microscopy by dry mount in DABCO/glycerol.

Figure 13:
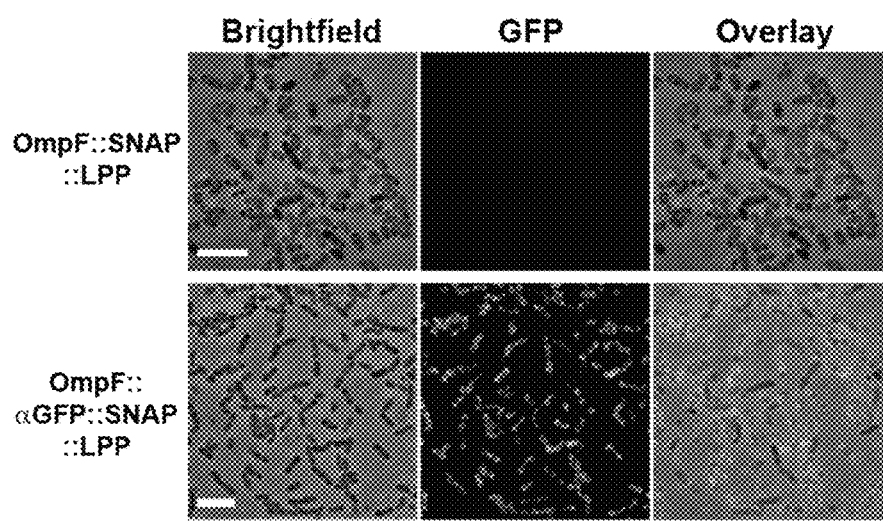

FIG. 13. Binding of eGFP by OmpF::αGFP::SNAP::LPP fusion protein. *E. coli* cells expressing the OmpF::SNAP::LPP or the OmpF::αGFP::SNAP::LPP fusion protein were permeabilised as described in Example 1. Purified eGFP protein was bound to the cell capsules as described in Example 8 and eGFP was visualized by fluorescence microscopy by dry mount, as described in Example 3. Cells expressing the OmpF::SNAP::LPP fusion protein lack eGFP fluorescence (second panel, top row), unlike cells expressing the OmpF::αGFP::SNAP::LPP fusion protein (second panel, bottom row).

Figure 14:
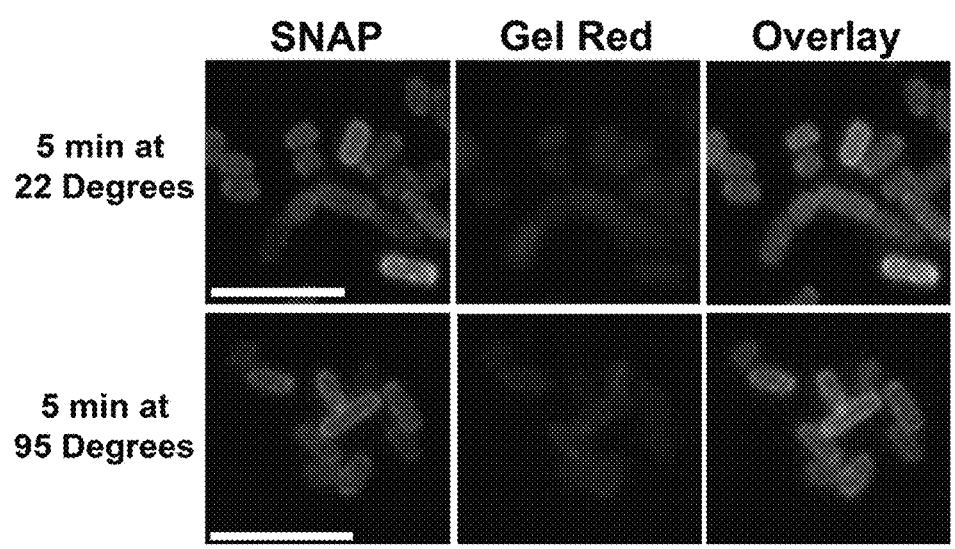

FIG. 14. Demonstration of covalent attachment to the cell wall by the LPP fusion protein. *E. coli* cells expressing the OmpF::αGFP::SNAP::LPP fusion protein were permeabilised as described in Example 1. Fusion protein localization was detected by labeling with the SNAP ligand BG-488 as described in Example 3 and DNA was stained with Gel Red. Samples were heated for 5 minutes at 22° C. (top row) or at 95° C. (bottom row) before being dry mounted and viewed by fluorescence microscopy.

Figure 15:
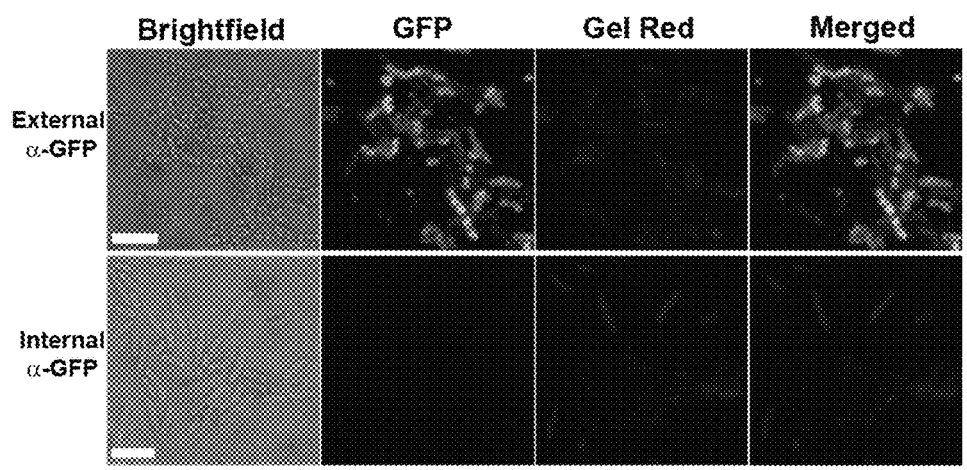
Figure 15:
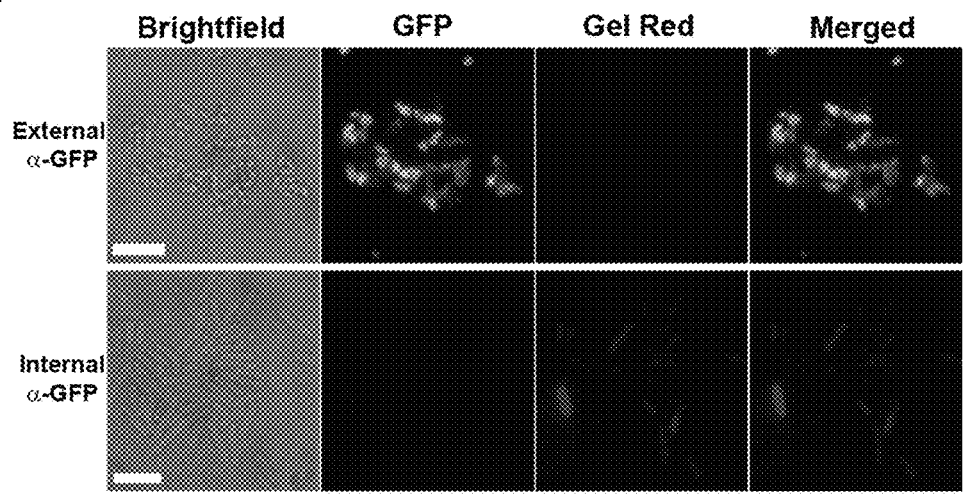

FIG. 15. Outer membrane permeabilisation using a detergent/$Ca^{2+}$ buffer. *E. coli* cells expressing the OmpF::αGFP::SNAP::LPP fusion protein (external αGFP or the αGFP::HALO::FLAG::RhnA fusion protein (internal αGFP) were permeabilised as described in Example 10. Permeabilisation of the outer membrane to large ligands was assessed by binding of eGFP to the αGFP domain attached to the cell wall. Permeabilisation of the inner membrane was assessed using a large ligand (eGFP) and small ligand (Gel Red). Both detergents Apo8 (A) and Tween20 (B) in $Ca^{2+}$ buffer demonstrated selective permeability of the outer membrane to large ligands.

Figure 16:
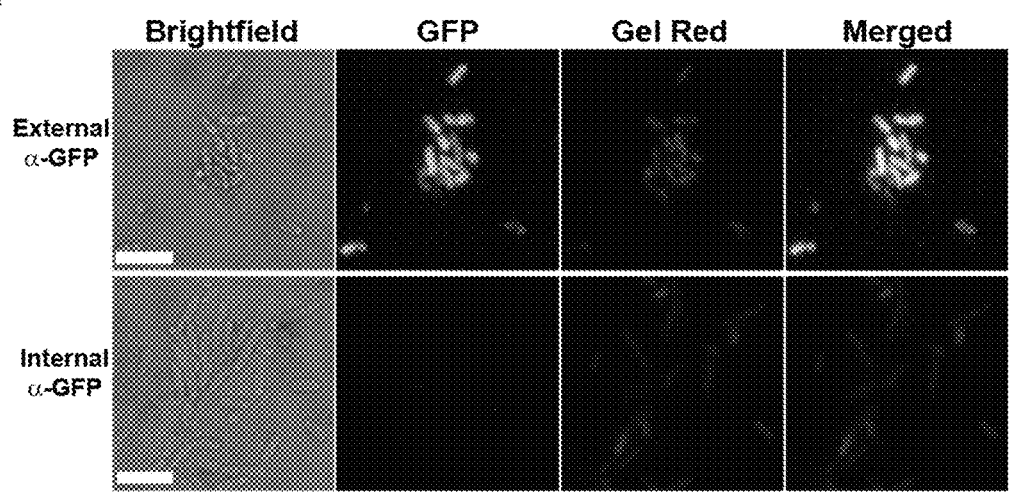
Figure 16:
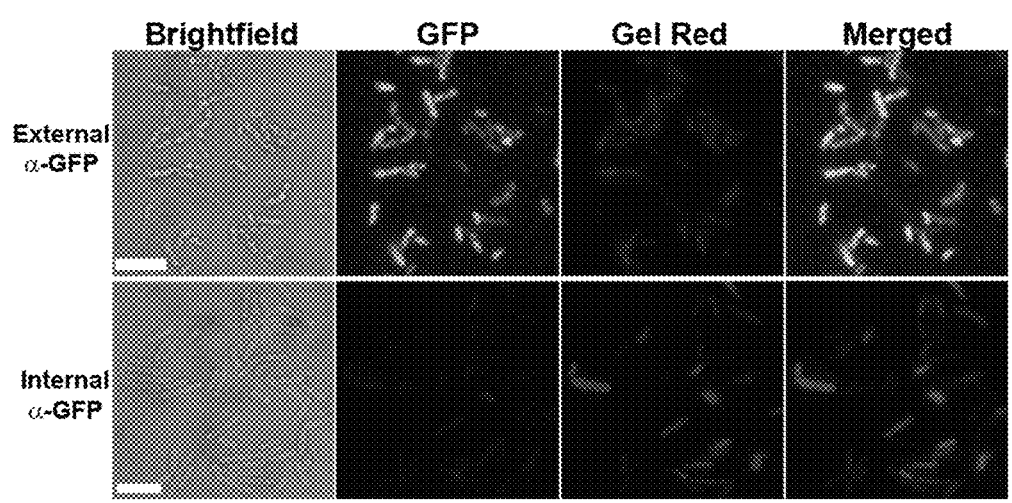

FIG. 16. Outer membrane permeabilisation using a detergent/EDTA buffer. *E. coli* cells expressing the OmpF::αGFP::SNAP::LPP fusion protein (external αGFP) or the αGFP::HALO::FLAG::RhnA fusion protein (internal αGFP) were permeabilised as described in Example 10. Permeabilisation of the outer membrane to large ligands was assessed by binding of eGFP to the αGFP domain attached to the cell wall. Permeabilisation of the inner membrane was assessed using a large ligand (eGFP) and small ligand (Gel Red). Both detergents Apo8 (A) and Tween20 (B) in EDTA buffer demonstrated selective permeability of the outer membrane to large ligands.

Figure 17:
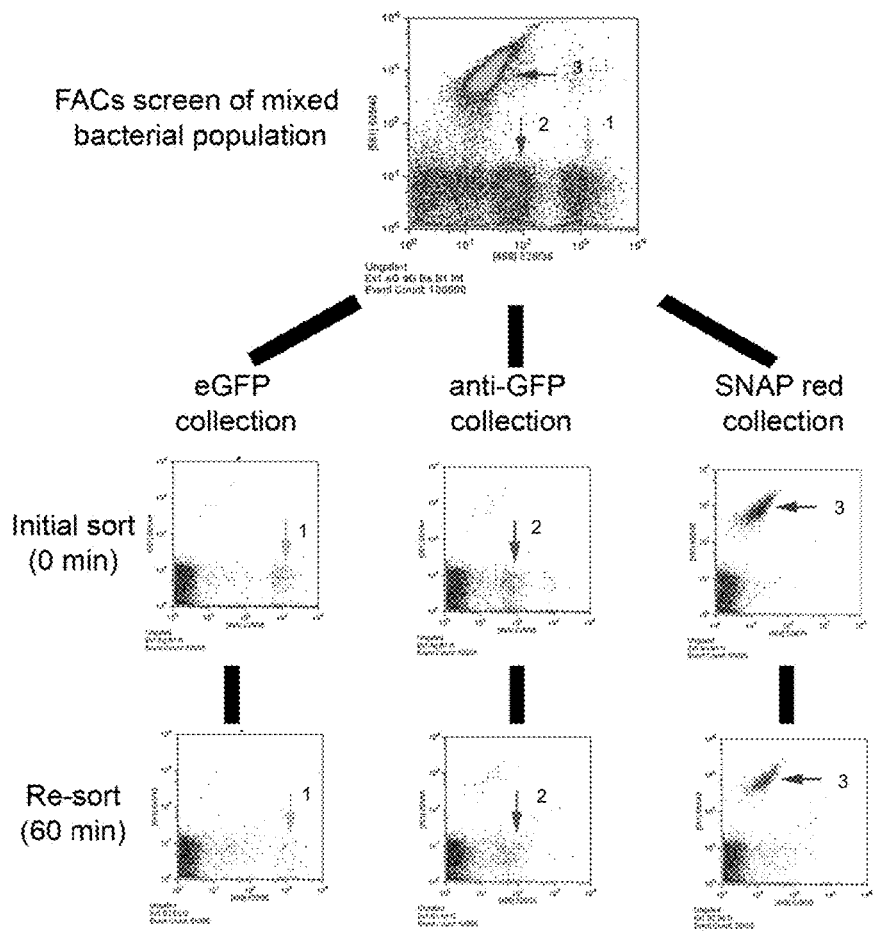

FIG. 17. FACS analysis of a mixed population of eGFP and SNAP-labeled cells. Three populations of *E. coli* cells expressing; eGFP (#1 arrow); the αGFP::KzPG::SNAP::DBP fusion protein labeled with SNAP ligand BG-488 (#2 arrow); and His6::SNAP::BetB labeled with SNAP ligand BG-547 (#3 arrow) were sorted by FACS. Sorted populations were reanalysed for purity and cell integrity 60 minutes after the first sort.

Figure 18:
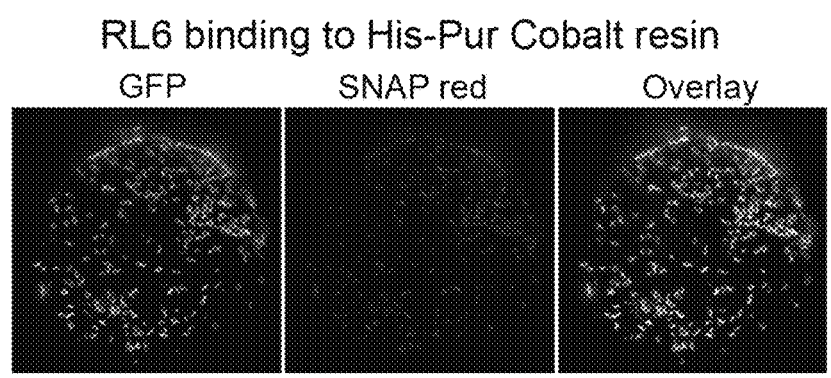

FIG. 18. A peptide linker between the αGFP and KzPG domains enables binding of *E. coli* cells expressing a αGFP::KzPG::SNAP::DBP fusion protein to a sepharose support. Cells expressing a αGFP::KzPG::SNAP::DBP fusion protein with a 12-mer linker region, RL6, between the αGFP and KzPG domains were bound to a $Co^{2+}$-sepharose support through a His6::eGFP intermediate. GFP binding is shown in the left panel (green); SNAP ligand (red) binding of the fusion protein is shown in the middle panel; overlay of each is shown on the right.

Figure 19:
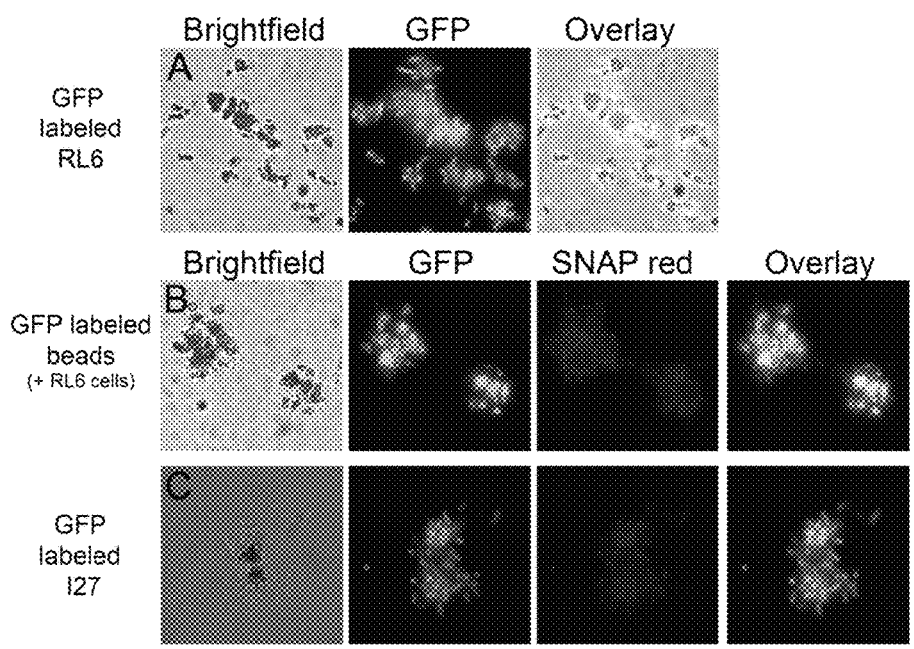

FIG. 19. Binding of *E. coli* cells expressing αGFP::RL6::KzPG::SNAP::DBP fusion protein to streptavidin-labeled magnetic beads. (A) Biotin-labeled eGFP (middle and right panels) was bound to cells expressing the αGFP::RL6::KzPG::SNAP::DBP fusion protein which was in turn bound to streptavidin-labeled magnetic particles. (B) Converse binding of cells expressing the αGFP::RL6::KzPG::SNAP::DBP fusion protein to streptavidin-labeled magnetic particles which had first been labeled with biotinylated-eGFP. In this example the beads are labeled green (GFP panel), the cells were labeled with the BG-547 SNAP ligand (red, SNAP red panel). (C) A domain linker, the $27^{th}$ Ig domain of human titin, was also effective as a binding spacer. *E. coli* cells expressing the αGFP::I27::RL6::KzPG::SNAP::DBP fusion protein were first bound to biotinylated eGFP (green, GFP panel) and labeled with the BG-547 SNAP ligand (red, SNAP red panel) before being bound to streptavidin-labeled magnetic particles.

Figure 20:
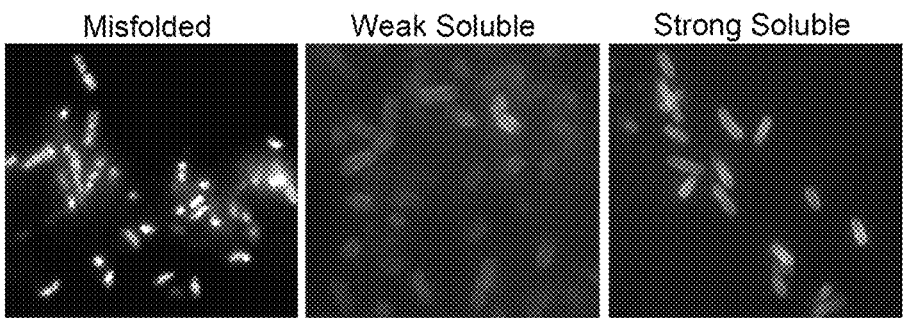

FIG. 20. Expression of mouse scFv genes in the *E. coli* cytoplasm as scFv::I27::RL6::KzPG::SNAP::DBP fusion proteins. A mouse scFv library was constructed and displayed according to the method of the invention in the *E. coli* cytoplasm. Clones with detectable expression were detected via SNAP ligand binding and were categorised as misfolded (left panel), weakly expressed but soluble (middle panel) or highly expressed and soluble (right panel).

Figure 21:
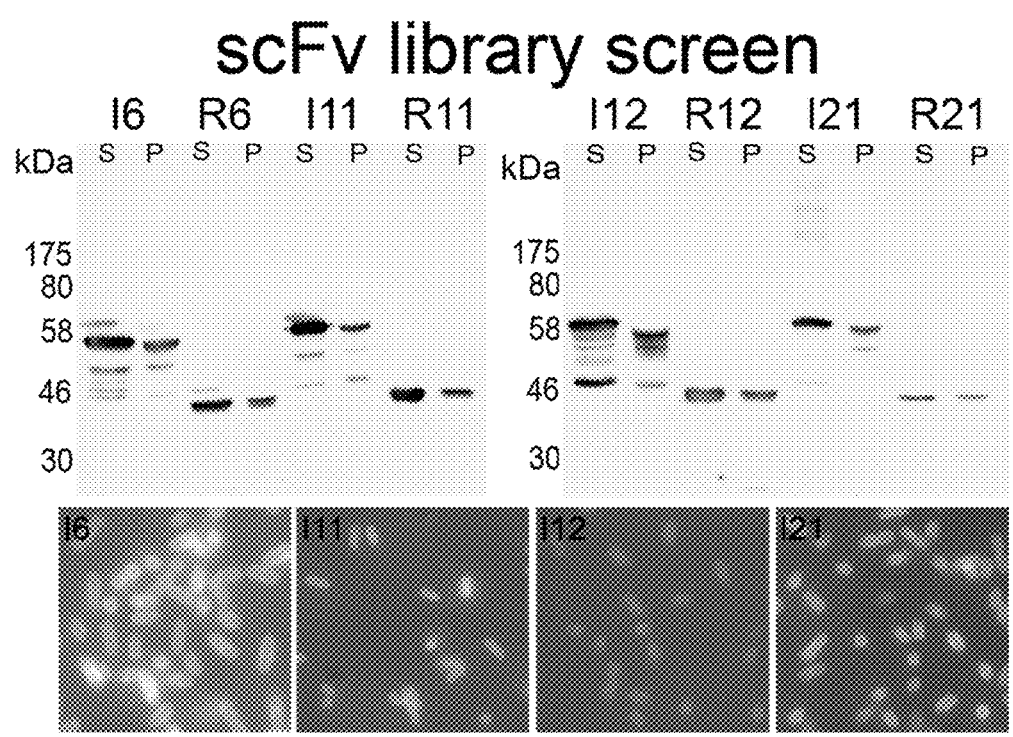

FIG. 21. Detection of soluble and insoluble scFv expression in the *E. coli* cytoplasm. Selected clones that were found to be highly expressed and soluble in a limited screen from the mouse scFv expression library were subcloned into expression constructs as scFv::I27::RL6::FLAG and scFv::RL6::FLAG fusion proteins. Protein fractions were loaded as either soluble or insoluble onto SDS-PAGE gels, transferred to nitrocellulose membranes and detected using αFLAG antibodies. Samples are paired for soluble (S) or insoluble (P) fractions, as well as each clone being expressed with the I27::RL6 (I) or RL6 (R) linker. A fluorescence microscopy image of the original scFv clone in the I27::RL6::KzPG::SNAP::DBP display construct isolated from the library screen is also shown in the lower panels.

Figure 22:
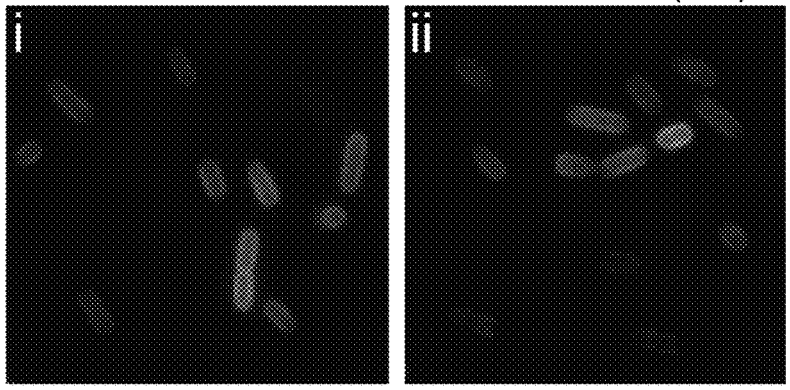

FIG. 22. Permeabilisation of *E. coli* membranes using organic solvents. *E. coli* cells expressing an αGFP::RL6::KzPG::SNAP::DBP fusion protein were suspended in aqueous mixtures of organic solvents. Membrane permeabilisation was indicated by the binding of (A) a small molecular weight DNA-binding fluorescent ligand, Gel Red; and of a 30 kD protein, eGFP. Of the organic solvents tested, only chloroform permeabilised both inner and outer membranes to enable entry into the cell of the high-molecular weight eGFP (B).

Figure 23:
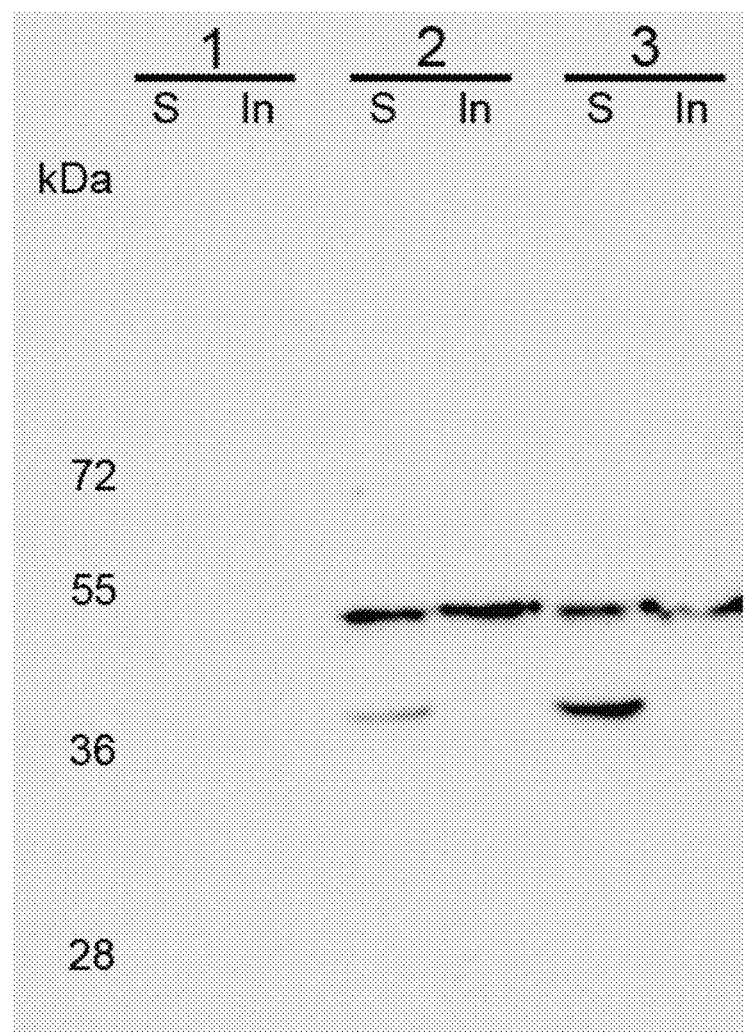

FIG. 23. Expression of αGFP:I27:gpL fusion protein in *E. coli*. Expression of the αGFP:I27:gpL fusion protein was induced by arabinose induction, as described in Example 20. Soluble protein was released from *E. coli* cells by permeabilisation with 0.5% 8TGP and the remainder of the sample was considered insoluble. Samples were boiled in SDS loading buffer and electrophoresed on a 15% SDS-PAGE. Proteins were transferred to nitrocellulose membrane and probed with αFLAG monoclonal antibody to detect the αGFP:I27:gpL fusion protein. (1) sample 1: uninduced αGFP:I27:gpL fusion clone 1; (2) induced αGFP:I27:gpL fusion clone 1; (3) induced αGFP:I27:gpL fusion clone 2. S=soluble fraction; In=insoluble fraction.

Figure 24:
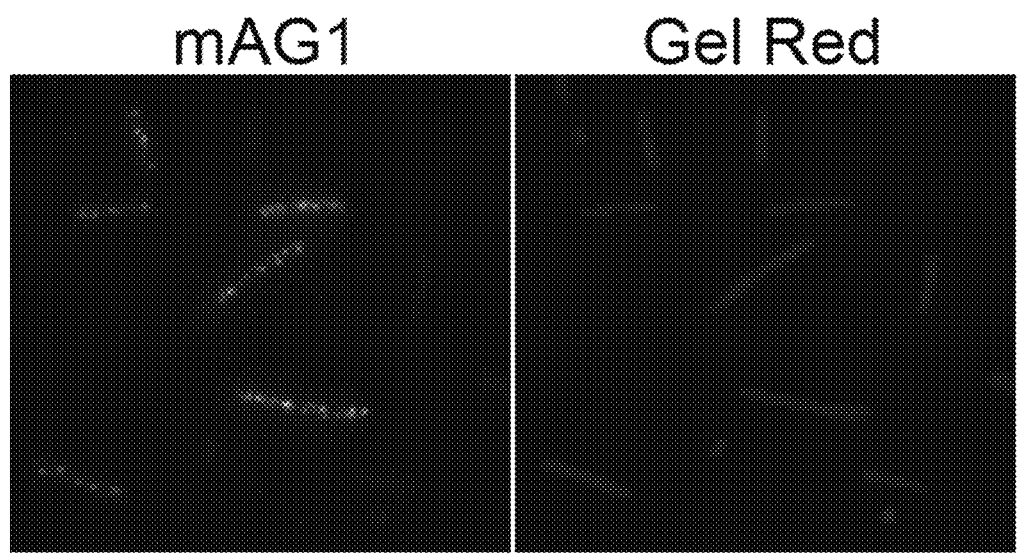

FIG. 24. Fluorescence imaging of mAG1-labeled encapsulated lambda phage displaying the gpD::α-mAG1 fusion protein. *E. coli* cells induced for a lambda prophage and expressing the gpD::α-mAG1 fusion protein were permeabilised and stained with the mAG1 protein and the DNA binding dye, Gel Red. mAG1 was observed by fluorescence microscopy to bind in a punctate pattern within permeabilised cells (left panel).

Figure 25:
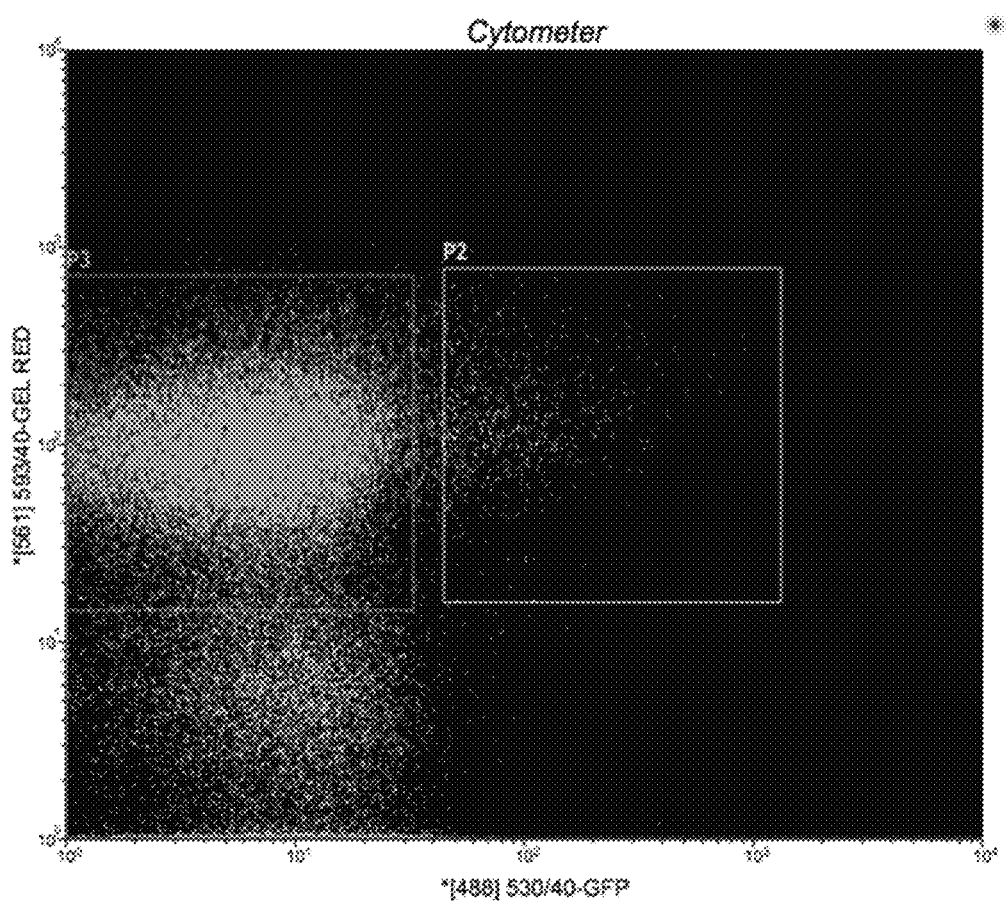

FIG. 25. Screenshot of Influx FACS analysis of encapsulated lambda phage displaying the gpD::α-mAG1 fusion protein. Shown is the fluorescence graph for 100 K events on an Influx FACS (BD Biosciences) with an input of ~1% of α-mAG1-positive cells. The cell population has been co-stained with the DNA binding dye, Gel Red (red; 561 nm), and the fluorescent mAG1 protein (green; 488 nm). The P2 gated population is α-mAG1-positive and the P3 gated population is α-mAG1-negative.

KEY TO THE SEQUENCE LISTING

SEQ ID NO:1—Nucleotide sequence of pAra3::His6::SNAP arabinose vector
SEQ ID NO:2—Nucleotide sequence of pAra3::His6::KzPG::SNAP::DBP vector
SEQ ID NO:3—Nucleotide sequence of pAra3::OmpF::SNAP::LPP vector
SEQ ID NO:4—Nucleotide sequence of pAra3::αGFP (R35)::HALO::FLAG::RhnA vector
SEQ ID NO:5—Randomized peptide spacer domain
SEQ ID NOs:6 to 12—Peptide linker spacers
SEQ ID NO:13—I27::RL6::KzPG::SNAP::DBP
SEQ ID NO:14—I27:: RL6::KzPG::SNAP::DBP coding sequence
SEQ ID NO:15—Library scaffold vector
SEQ ID NO:16—I27 spacer
SEQ ID NO:17—Nucleotide sequence of enterobacteriophage P2 endolysin gene
SEQ ID NO:18—Nucleotide sequence of enterobacteriophage P2 holin gene
SEQ ID NO:19—Nucleotide sequence of temperature-inducible P4 δ vector
SEQ ID NO:20—Amino acid sequence of the αGFP::I27::gpL fusion protein
SEQ ID NO:21—Amino acid sequence of the gpL::αGFP::I27 fusion protein
SEQ ID NO:22—Nucleotide sequence of the αGFP::I27::gpL fusion protein expression vector
SEQ ID NO:23—Nucleotide sequence of lambda phage holin gene
SEQ ID NO:24—Nucleotide sequence of lambda phage lysozyme gene
SEQ ID NO:25—Amino acid sequence of lambda lysis cluster deletion remnant
SEQ ID NO:26—Nucleotide sequence of the lambda cos region
SEQ ID NO:27—Nucleotide sequence of the lambda SR deletion (ΔSR) vector

DETAILED DESCRIPTION

General Techniques and Definitions

Unless specifically defined otherwise, all technical and scientific terms used herein shall be taken to have the same meaning as commonly understood by one of ordinary skill in the art (e.g., in protein chemistry, biochemistry, cell culture, molecular genetics, microbiology, and immunology).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook and Russell., Molecular Cloning: A Laboratory Manual, $3^{rd}$ edn, Cold Spring Harbour Laboratory Press (2001), R. Scopes, Protein Purification—Principals and Practice, $3^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The terms "polypeptide", "protein" and "peptide" are generally used interchangeably herein. As used herein, the term "exogenous polypeptide" refers to a polypeptide encoded by an exogenous polynucleotide. The term "exogenous polynucleotide" as used herein refers to a polynucleotide which is foreign to the cell into which it has been introduced, or that the sequence is homologous to a sequence in the cell into which it is introduced but in a position within the host cell nucleic acid in which the polynucleotide is not normally found.

The term "antibody" as used in this invention includes polyclonal antibodies, monoclonal antibodies, bispecific antibodies, diabodies, triabodies, multibodies, heteroconjugate antibodies, chimeric antibodies including intact molecules as well as fragments thereof, such as Fab, F(ab')2, Fv and scFv and other antibody-like molecules.

The term "about" as used herein refers to a range of +/−5% of the specified value.

Lysis-Defective Phage

In one embodiment of the invention, a polypeptide is screened for a desired activity in a Gram-negative bacterial cell, wherein the polypeptide is produced in the cell and the polynucleotide encoding the polypeptide is packaged into a lysis-defective phage. By "lysis-defective phage" it is meant a lytic or temperate phage that would normally have a lytic stage in its life-cycle but which has been modified so that, although it may enact all other functions of a lytic cycle, it is incapable of lysing a Gram-negative bacterial cell to release packaged phage. Thus, lysis-defective phage include temperate phage that are capable of having a lysogenic cycle in which the viral genome is integrated into the host cell DNA as a prophage, or which replicates as a plasmid (phagemid). The prophage remains dormant in the bacterial cell until host cell conditions allow for the prophage to become active and initiate the reproductive cycle. Whereas initiation of the reproductive cycle of a prophage would normally result in lysis of the bacterial host cell, the lysis-defective phage in the method of the present invention has been modified so that the bacterial host cell is not lysed and the phage remains within the bacterial cell.

The term "lysis-defective phage" as used herein does not include reference to a phage that does not normally have a lytic stage in its lifecycle, hence the skilled person will understand that it does not include reference to phage that are released from a bacterial cell by extrusion, for example filamentous phage such as M13, f1 or f2, or that are released from a bacterial cell by budding.

Examples of lytic phages that may be modified to remove the lytic stage from their life-cycle so as to produce a lysis-defective phage include phiX174, T1, T2, T3, T4, T5, T6 and T7 bacteriophages. Examples of lysogenic phage which may be modified so as to remove the lytic stage of their life-cycle include lambda phage, N15 phage, P22 phage, Mu phage, P2 phage, phage 186 and the P2 satellite phage, P4 (Lindqvist et al., 1993; Ziermann et al., 1994; Liu et al., 1997; and Briani et al., 2001).

The skilled person will understand that some temperate phages that are capable of packaging a polynucleotide in a bacterial cell require the presence of another phage, for example, a helper phage, in order to undergo polynucleotide packaging and/or for bacterial cell lysis to occur. An example of this relationship is the P2 phage and its satellite phage, P4. The requirement for the presence of a helper phage for polynucleotide packaging and/or for bacterial cell lysis is known as a helper-phage system. In a helper-phage system, the activity of a helper-phage, or of phage polypeptides (i.e. "activator proteins"), induces another phage to undergo polynucleotide packaging and/or cause bacterial cell lysis. Thus, the skilled person will understand that while a polynucleotide may be packaged into one phage (i.e. one phage in a helper-phage system), the activity of another phage (i.e. a helper-phage) may be required to lyse the bacterial cell in which both the phages are present. For use in some embodiments of the method of the present invention, the phage which would normally provide the lytic activity is modified so that it is no longer capable of lysing a bacterial cell. Accordingly, the term "lysis-defective phage" as used herein also refers to a phage into which a polynucleotide is packaged, wherein the phage would normally rely on a second phage to provide lytic activity, but in which the second phage has been modified so that it is no longer capable of lysing a Gram-negative bacterial cell.

The skilled person will appreciate that the polynucleotide may also be physically separate from the genome of the lysis-defective phage. For example, the polynucleotide may be operably linked to sequences that are sufficient for packaging of the polynucleotide by the phage structural and replicative proteins to form an infectious unit that morphologically resembles, or is identical to, the parental strain of the lysis-defective phage.

As a non-limiting example, plasmid vectors of the appropriate size may contain the sequence around the cos region required for DNA packaging into the lambda bacteriophage. These plasmid vectors may be packaged in vivo by helper phage, and may also be packaged in vitro by purified extracts containing the phage structural and replicative proteins. A sequence sufficient for lambda packaging is provided as SEQ ID NO:26. These vectors are known as cosmids (cos+plasmid), and are well-known to the skilled person for their ability to clone exogenous polynucleotides and propagate them as bacteriophage particles. Commercial kits for cloning polynucleotides within cosmids, and kits for in vitro packaging are known in the art.

Exemplary Helper-Phage System: The P2-P4 System

One non-limiting example of a helper-phage system is the P2-P4 phage system. While each phage carries the genes necessary to assure its own DNA replication and integration into the host genome, the *E. coli* P4 phage lacks the genetic information necessary for tail and lysis functions, as well as the major structural protein for capsid formation (Kahn et al., 1991; Liu et al., 1997). P4 is therefore reliant on phage P2, or P2-related phage, such as phage 186, in order to make P4 phage structural components, to package its DNA and to lyse the host cell. When P4 infects a P2 lysogenic host cell (for example, *E. coli* comprising a P2 prophage in its genome), the P2 prophage is derepressed by the P4 e gene. Derepression results in P2 early and late-gene expression and is sufficient for the completion of the P4 lytic cycle.

P4 may also be packaged by the P2-like phage, phage 186. This phage has orthologous structural proteins to P2 (~75% identity) and hybrid P2/186 phage have been constructed that contain the P2 structural genes that are regulated by the phage 186 transcription factors (Younghusband et al., 1975). Crucially, the early region of phage 186, and P2/186 hybrids (Hy2 and Hy5) is not related to P2 and thus is not inhibited by the P4ε protein. However, a phage 186 can be used as a P4 helper phage if the temperature-sensitive mutant of the phage 186 immunity repressor is used to induce phage 186 functions to coincide with P4 infection (Sauer et al., 1982) or activation.

The skilled person will understand that a P2/P4 bacteriophage system will be suitable for use in the method of the present invention. Advantageous features of a P2/P4 bacteriophage system include:

i) the preference of P2 terminase enzyme for plasmid templates, unlike other bacteriophage terminases which prefer to package concatamerised, linear polynucleotide templates. Hence, this system is more suitable for in vivo packaging of plasmids that encode the polypeptide being screened for a desired activity, and ii) a cosmid (i.e. a plasmid that comprises bacteriophage cos sequence that dictates bacteriophage packaging) that can be packaged efficiently into a P4-sized capsid (approximately 10-12 kb) is more amenable to routine cloning methods and iterative mutagenesis than larger bacteriophage genomes, such as lambda (48.5 kb).

Genetic Modification to Produce Lysis-Defective Phage

The life-cycle of lytic bacteriophage involves both genome replication and packaging as a phage particle, but also cell lysis for release of the particles for re-infection. Cell lysis of Gram-negative bacteria is a two-stage process, with the inner membrane being first perforated, allowing a cell-wall degrading enzyme (a lysozyme) to access the periplasmic space and act on the peptidoglycan cell wall. The cell is lysed by the difference in osmotic pressure between the cytoplasm and the surrounding solution thereby releasing phage particles into the medium.

The activities of membrane perforation (holin) and lysozyme are usually encoded by two genes in most lytic and lysogenic phage. Due to the parsimony of most phage genomes, these genes are often neighbours in the same operon. To retain the integrity of the cell wall, and to prevent the release of phage particles and proteins that are being functionally screened by a method of the invention, the gene encoding the phage lysozyme, or both the lysozyme and the holin, must be deleted from the phage genome. Due to the frequent use of overlapping reading frames and stop/start codons leading to translational coupling in many phage genes, the effects on the downstream gene/s must be carefully considered when designing these deletions. If the lysis cluster is translationally coupled to downstream structural genes, then preferably the deletion would leave a truncated ORF as the residual 'scar' at the locus having the start region of one gene and the stop region of the other.

In one embodiment, the method of protein screening of the invention uses permeabilisation of both inner and outer membranes of Gram-negative bacterium while retaining the structural integrity of the peptidoglycan cell wall. Thus, in this embodiment, the holin genes may be kept functional in the bacteriophage genome and may help contribute to the permeabilisation of the inner membrane, whereas the lysozyme gene is deleted in order to retain the cell wall structural integrity. In the instance of the lysis-defective phage being used in a screening system that is coupled to a periplasmic-targeted protein, such as described in WO 2002/034886 and WO 2005/095988, or to cell-wall binding fusion proteins, then the holin or holin/lysozyme functions must be deleted from the phage genome in order to retain the integrity of the inner membrane of the cell or spheroplast.

The person skilled in the art will understand that the lysin and/or lysozyme gene functions may be deleted by deleting the gene encoding the molecules from the phage genome, or alternatively by mutating the lysin and/or lysozyme genes such that they are are defective and no longer encode a functional lysin and/or lysozyme protein.

In embodiments of the invention that utilise the P2 and P4 satellite system, the P2 genome contains both the holin (Y) and lysozyme genes (K) used by P4. Thus, a P2 prophage may be modified by deletion of the K, Y or YK genes. Construction of a lysis-defective P2 phage is described in Example 16 with the deletion of the YK genes from the genome of a P2 prophage of a K12 strain of E. coli. The P2ΔYK prophage carrying a P4-sized cosmid may be infected by a P4 bacteriophage thereby inducing packaging of the cosmid. The cosmid may also be induced for expression of the gene to be functionally screened. At the conclusion of induction of both cosmid packaging and gene expression, the cell membranes may be permeabilised and the cellular capsid screened by the method of the invention. Packaging of a cosmid by a lysis-defective P2 phage in an E. coli strain is described in Example 18 using infection of a strain carrying the P2ΔYK prophage by a P4 phage.

In embodiments of the invention that utilise the lambda phage system, the lambda S and R genes encode the holin and endolysin (lysozyme), respectively. Deletion, or mutational inactivation, of the R or SR genes would produce a lysis-defective lambda prophage.

Construction of a lysis-defective lambda phage is described in Example 20 with the deletion of the SR genes from the genome of a lambda prophage of a K12 strain of E. coli. Packaging of a cosmid by a lysis-defective lambda phage in a E. coli strain is described in Example 21 by induction through inactivation of the thermolabile cI repressor.

In embodiments of the invention that utilise a lytic phage, using the T7 phage as an example, a lysis defective phage may be produced by mutational inactivation of gene 3.5 which encodes the T7 lysozyme. As the T7 lysozyme has a regulatory activity on T7 transcription via its inhibitory interaction with T7 RNAP, deletion of the lysozyme would be inadvisable. Therefore, mutants that specifically inactivate the cell-wall amidase activity of the enzyme are required to create lysis-defective mutants that retain T7 replication.

The lysin/holin systems of other lytic or lysogenic phages may be identified through comparison to known phage genomes, or through genetic analysis, and corresponding lysis-defective mutants may be created for their use in packaging libraries in the methods of the present invention.

Polynucleotide Packaging by Lysis-Defective Phage

In the methods of screening of the invention that utilise a lysis-defective phage, the method comprises culturing a Gram-negative cell comprising an exogenous polynucleotide encoding the polypeptide being screened such that the polypeptide is produced within the cell, and allowing the lysis-defective phage to package the polynucleotide encoding the polypeptide. The phrase "allowing a lysis-defective phage to package the polynucleotide" means that conditions are provided within a Gram-negative bacterial cell such that a lysis-defective phage is capable of packaging a polynucleotide.

The skilled person will understand that in some cases the culturing of the Gram-negative bacterial cell to produce the polypeptide and allowing the lysis-defective phage to package the polynucleotide may occur simultaneously. By way of non-limiting example, a Gram-negative bacterial cell comprising a helper prophage and a cosmid encoding a polypeptide of interest may be infected with a lysis-defective phage capable of packaging the cosmid, and then cultured to produce the polypeptide.

Alternatively, a Gram-negative bacterial cell comprising a helper prophage and a cosmid encoding a polypeptide of interest may be treated to induce the packaging functions of the prophage through, for example, heat inactivation of a labile repressor protein, or through co-induction of an activator protein, and then cultured to produce the polypeptide.

In this way, the polypeptide is produced in the Gram-negative bacterial cell while simultaneously the cosmid is packaged into the lysis-defective phage.

In one embodiment, the lysis-defective phage is retained (i.e. encapsulated) within a permeabilised Gram-negative bacterial cell and the polypeptide is screened for a desired activity according to the method of the invention. Specifically, a gene library encoding the polypeptide to be screened is cloned into a lysis-defective phage, or into a cosmid, and introduced into a Gram-negative bacterial cell. Both phage packaging and the polypeptide to be screened may be co-induced (i.e. induced simultaneously) and at the appropriate time point the population of Gram-negative bacterial cells is permeabilised using either a detergent or organic solvent with the polypeptide being retained within the cellular capsid, along with the phage. The population of permeabilised Gram-negative bacterial cells is then screened for the desired polypeptide activity.

The steps of culturing the Gram-negative bacterial cell to produce the polypeptide and allowing the lysis-defective phage to package the polynucleotide encoding the polypeptide may also be performed sequentially rather then simultaneously. Thus, the Gram-negative bacteria may be first cultured to produce the polypeptide, and subsequently the lysis-defective phage is allowed to package the polynucleotide encoding the polypeptide. The sequential production of the polypeptide in the bacterial cell followed by polynucleotide packaging may occur, for example, in instances where the polypeptide is encoded by a cosmid in the bacterial cell, and infecting the bacterial cell with a helper phage allows the lysis-defective phage to package the polynucleotide encoding the polypeptide. In one example of the method of the invention, the bacterial cell comprises P2 and/or P4 prophage and inducing activation of P2 prophage comprises inactivating a temperature sensitive repressor allele of P2 protein C in the bacterial cell and/or expression of P4 activator proteins in the bacterial cell.

Alternatively, the Gram-negative bacteria may be cultured under conditions suitable for the production of the polypeptide, and allowing the lysis-defective phage to package the polynucleotide encoding the polypeptide may comprise inducing activation of a prophage in the bacterial cell to produce phage, wherein the phage packages the polynucleotide. As will be understood by the person skilled in the art, the step of inducing activation of the prophage in the cell could be performed simultaneously or sequentially with the step of culturing the Gram-negative bacterial cell to produce the polypeptide in the cell.

In light of the present specification, the skilled person will understand that there are several ways in which inducing activation of a lysis-defective phage to package a polynucleotide may be achieved. For example, inducing activation of a lysis-defective phage may comprise introducing a satellite or helper phage into a Gram-negative bacterial cell comprising a lysis-defective phage that is present as in the bacterial cell genome as prophage.

Alternatively, inducing activation may comprise producing one or more activator proteins of a prophage in a bacterial cell. For example, the Gram-negative bacterial cell may comprise a P2 and/or P4 prophage, and the P2 and/or P4 activator proteins may be, for example, selected from one or more of P2 cox, P2 ogr, P4 δ and/or P4ε. As a result of activation, a prophage in a bacterial cell produces phage which package the polynucleotide. Alternatively, inducing activation of a lysis-defective phage to package a polynucleotide may comprise inactivating one or more phage repressor proteins in the bacterial cell. In one particular embodiment of the invention, inducing activation comprises inactivating a temperature sensitive repressor allele of lambda prophage in the bacterial cell. In another embodiment, inducing activation of a lysis-defective phage comprises increasing the incubation temperature of the bacterial cells.

Permeabilisation

In certain embodiments of method of the invention, either the outer cellular membrane alone, or both the inner and outer cellular membranes of a Gram-negative bacterial cell are permeabilised, thus allowing at least some of the soluble cellular components to diffuse through the cell wall. The polypeptide to be screened for a desired activity is retained within the bacterial cell wall, or is attached to the bacterial cell wall. As used herein, the terms "permeabilisation", "permeabilised" or "permeabilised bacterial cell" refer to the use of a permeabilising agent or mechanical treatment, or a combination or both, to produce pores in the outer membrane, or both the inner and outer membranes, of a Gram-negative bacterium, or to solubilise the outer membrane, or both the inner and outer membranes, of a Gram-negative bacterium, while not hydrolysing linkages between peptidoglycans thereby keeping the cell wall intact. Non-limiting examples of agents capable of permeabilising a bacterial cell include detergents and organic solvents. A non-limiting example of a mechanical treatment capable of permeabilising a bacterial cell is electroporation.

Permeabilisation advantageously allows the entry of small to moderately sized proteins, for example up to 120 kDa, or other molecules of equivalent or smaller size, into the cellular capsule that remains intact. Further, by maintaining the integrity of the bacterial cell wall, the permeabilised bacterial cells are less fragile than spheroplasts that are produced, for example, by treatment of bacterial cells with Tris-EDTA-lysozyme, in which the bacterial cell wall is at least partially hydrolysed. The permeabilised bacterial cells produced in certain embodiments of the methods of the present invention are well suited to techniques such as fluorescence activated cell sorting (FACS), whereas spheroplasts are damaged by the high shear flow cytometry environment and require controlled osmotic conditions, thus limiting their potential uses.

Preferably, the permeabilisation treatment preserves the cellular proteins in their native state and interactions. Non-ionic detergents are generally less disruptive to protein folding and protein complexes than ionic detergents. Thus, in a preferred embodiment, a non-ionic detergent is used to permeabilise the bacterial cell wall. Non-limiting examples of non-ionic detergents include Triton X-100, Triton X-114, Brij 35, Brij 58, Tween 20, Tween 80, Nonidet P-40 Substitute, Octyl β Glucoside, Mega 8, Mega 9, Mega 10, BigCHAP, Deoxy BigCHAP, Apo8, and 8TGP (n-octyl-β-D-thioglucopyranoside).

Mixtures of detergents may be used to permeabilise the bacterial cell. For example, the detergent may be a mixture of two or more non-ionic detergents. In one embodiment, the detergent is a mixture of Mega 10 and Apo8.

When the polypeptide to be screened for a desired activity is attached to the bacterial cell wall, or integrated or attached to the inner cell membrane, the skilled person will appreciate that it may not be necessary to permeabilise the inner membrane of the bacterial cell. Thus, in one embodiment the bacterial cell is selectively permeabilised. By "selectively permeabilised" it is meant the outer membrane of the permeabilised bacterial cell is permeabilised to a greater extent than the inner membrane, whereby 50% or less, or more preferably 40%, 30%, 20%, 10%, 5%, 4%, 3%, 2%, 1% or less, or none, of a membrane impermeable substance, for example the membrane impermeable DNA-binding ligand Gel Red, permeates the inner membrane of a selectively permeabilised cell when compared to a permeabilised cell in which both the inner and outer membranes have been permeabilised such as by using a solution comprising 0.5% Mega 10 and 0.5% Apo8.

While the skilled person will be able to determine suitable conditions for selectively permeabilising a bacterial cell in accordance with the methods of the present invention, in one embodiment the bacterial cell is selectively permeabilised with a non-ionic detergent. For example, the non-ionic detergent may be selected from Apo8 and Tween20. In one embodiment, a solution for selectively permeabilising the bacterial cell comprises the detergent at a concentration of about 0.2% to about 0.4%, or about 0.2% to about 0.3%, or at about 0.2%. Preferably, the solution for selectively permeabilising the bacterial cell comprises the detergent in a buffer comprising $Ca^{2+}$ or EDTA. Exemplary buffers suitable for selectively permeabilising a bacterial cell include 0.2-0.4% Apo8 or Tween20 in 25 mM Tris, 1 mM EDTA (pH 8.0), or 25 mM Tris, 2 mM $Ca^{2+}$ (pH 8.0). In one embodiment, selective permeabilisation of a bacterial cell may be achieved, for example, by incubating the cell in a suitable buffer at about 25° C. for about 10 minutes.

In another embodiment, the agent capable of permeabilising a Gram-negative bacterial cell is an organic solvent such as chloroform. By way of example, the inner and outer bacterial cellular membranes can be permeabilised by the suspension of the Gram-negative bacterial cells in an aqueous solution that has been saturated with the lipophilic solvent chloroform. To create a saturated solution of chloroform requires mixing of the two immiscible phases of water and the organic solvent by agitating the two, usually by shaking, or on a mechanical vortex, until the chloroform phase is suspended as fine droplets. The two phases are allowed to settle, and a pulsed centrifugation is used to aid in the separation of the phases. A mixture of 5% (v/v) chloroform is sufficient to create a saturated solution. An incubation time of 10 minutes at 25° C. is sufficient for permeabilisation of both cellular membranes. Example 19 and FIG. 22 describe and demonstrate the permeabilisation of E. coli inner and outer membranes using organic solvent, chloroform.

Polypeptide Expression

A polypeptide to be screened for a desired activity may be cloned into a suitable vector for expression in a bacterial cell. "Vector" as used herein refers to any vector known in the art to be suitable for transforming a bacterial cell. Preferably, the vector is also capable of replicating within the bacterial cell independently of the host's genome. Vectors include plasmids, viruses and cosmids as well as linear DNA elements, such as the linear phage N15 of *E. coli*, and/or extrachromosomal DNA that replicates independently of a bacterial cell genome. Preferably, the vector is an expression vector. As would be understood by the skilled person, in embodiments in which the polynucleotide encoding the polypeptide is packaged into a phage, the vector will be in a suitable form, and comprise the necessary sequence (for example, such as the cos sequences in a cosmid), for packaging of the polynucleotide into the phage.

As used herein, an "expression vector" is a vector that is capable of effecting expression of a specified polynucleotide molecule in a bacterial cell. Preferably, the expression vector is also capable of replicating within the bacterial cell. Suitable expression vectors typically contain regulatory sequences such as transcription control sequences, translation control sequences, origins of replication, and other regulatory sequences that are compatible with the recombinant bacterial cell and that control the expression of polynucleotide molecules encoding a polypeptide. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a bacterial cell. A variety of such transcription control sequences are known to those skilled in the art.

Transformation of an expression vector into a bacterial cell can be accomplished by any suitable method by which a polynucleotide molecule can be inserted into the cell. Transformation techniques include, but are not limited to, electroporation and chemical transformation. Transformed polynucleotide molecules can remain extrachromosomal or can integrate into one or more sites within a chromosome of the transformed (i.e., recombinant) cell in such a manner that their ability to be expressed is retained.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules include, but are not limited to, operatively linking polynucleotide molecules to high-copy number plasmids, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

The skilled person will be able to readily determine bacterial strains suitable for expressing polypeptides in the methods of the invention. Those skilled in the art would understand that Gram-negative bacteria suitable for use in the methods of the invention include *Salmonella, E. coli, Shigella, Campylobacter, Fusobacterium, Bordetella, Pasteurella, Actinobacillus, Haemophilus* and *Histophilus*. In a preferred embodiment, the Gram-negative bacteria is *E. coli*.

Protein Complexes

The polypeptide to be screened for a desired activity may be associated with at least a second polypeptide to form a protein complex having a molecular size such that the protein complex is retained inside the permeabilised bacterial cell. The polypeptide may be associated with the second polypeptide by, for example, covalent bonds such as disulphide bridges, or by non-covalent association. "Non-covalent association" refers to molecular interactions that do not involve an interatomic bond. For example, non-covalent interactions involve ionic bonds, hydrogen bonds, hydrophobic interactions, and van der Waals forces. Non-covalent forces may be used to hold separate polypeptide chains together in proteins or in protein complexes. Thus, the polypeptide and second polypeptide may be expressed as separate polypeptides either from the same or different vectors, or one or both of the polypeptides may be expressed from DNA encoding the polypeptides that has been integrated into the bacterial cell genome.

Alternatively, the polypeptide and second polypeptide which are associated in a protein complex may be a fusion protein. As used herein, "fusion protein" refers to a hybrid protein, which consists of two or more polypeptides, or fragments thereof, resulting from the expression of a polynucleotide that encodes at least a portion of each of the two polypeptides and joined by a peptidic bond.

Protein Complexes Retained in the Permeabilised Bacterial Cell by Molecular Size The second polypeptide may be any polypeptide having sufficient molecular size, i.e. sufficient molecular weight or molecular radius, such that at least some of the complex formed with the polypeptide being screened for a desired activity is incapable of diffusion from the permeabilised bacterial cell. Thus, the protein complex is retained within the bacterial cell following permeabilisation of the cell. The person skilled in the art will appreciate that the nature of the second polypeptide, including its molecular weight and whether it is a globular or rod (filamentous) protein, will determine its ability to prevent or inhibit diffusion of the protein complex through the bacterial cell wall. In one embodiment, the molecular weight of the second polypeptide is at least about 30 kDa, or at least about 40, 50, 60, 70, 80, 90, 100, 120, 130, 140, 150 or more kDa. In one embodiment, the second polypeptide is at least about 120 kDa.

In one embodiment, the second polypeptide forms multimers having a molecular size greater than the pore-exclusion size of the permeabilised bacterial cell. As used herein, the term "multimer" and grammatical variations thereof refer to formation of a multimeric complex between two or more distinct molecules. The multimer may comprise, for example, two or more molecules of the same protein (i.e. a homo-multimer) or a mixture of two or more different or non-identical proteins (i.e. a hetero-multimer). Proteins that form multimers suitable for use in the methods of the invention include those that form dimers, trimers, tetramers, pentamers, hexamers, and higher order multimers comprising seven or more subunits.

Multimeric proteins include homodimers, for example, PDGF receptor α and β isoforms, erythropoietin receptor, MPL, and G-CSF receptor, heterodimers whose subunits each have ligand-binding and effector domains, for example, PDGF receptor αβ isoform, and multimers having component subunits with disparate functions, for example, IL-2, IL-3, IL-4, IL-5, IL-6, IL-7, and GM-CSF receptors. Non-limiting examples of other multimeric proteins that may be utilized in the methods of the present invention include factors involved in the synthesis or replication of DNA, such as DNA polymerase proteins involved in the production of mRNA, such as TFIID and TFIIH; cell, nuclear and other membrane-associated proteins, such as hormone and other signal transduction receptors, active transport proteins and ion channels, multimeric proteins in the blood, including hemoglobin, fibrinogen and von Willabrand's Factor; proteins that form structures within the cell, such as actin, myosin, and tubulin and other cytoskeletal proteins; proteins that form structures in the extra cellular environment, such as collagen, elastin and fibronectin; proteins involved in intra- and extra-cellular transport, such as kinesin and dynein, the SNARE family of proteins (soluble NSF attachment protein receptor) and clathrin; proteins that help regulate chromatin structure, such as histones and protamines, Swi3p, Rsc8p and moira; multimeric transcription factors such as Fos, Jun and CBTF (CCAAT box transcription factor); multimeric enzymes such as acetylcholinesterase and alcohol dehydrogenase; chaperone proteins such as GroE, Gro EL (chaperonin 60) and Gro ES (chaperonin 10); anti-toxins, such as snake venom, botulism toxin, *Streptococcus* super antigens; lysins (enzymes from bacteriophage and viruses); as well as most allosteric proteins. In one embodiment, the multimeric protein is an *E. coli* protein. Non-limiting examples of *E. coli* proteins that form multimers include L-rhamnose isomerase (RhnA; for example NCBI accession CAA43002), β-galactosidase (β-gal; for example NCBI accession YP 001461520), betaine aldehyde dehydrogenase (BetB; for example NCBI accession AAA23506), glutamate-5-kinase (GSK; for example NCBI accession AAB08662), glutathione synthase (GshB; for example NCBI accession AP_003504), and a medium chain aldehyde dehydrogenase (YdcW; for example NCBI accession AP_002067).

In one embodiment, the polypeptide being screened for a desired activity has a molecular size sufficient to retain the polypeptide within the bacterial cell wall. Thus, the person skilled in the art will appreciate that such a polypeptide need not necessarily be associated with a second polypeptide in order to retain the polypeptide within the permeabilised bacterial cell.

Capsid Display on Lytic and Lysogenic Phage

In another embodiment, the polypeptide may be attached to a large macromolecular complex, such as a bacteriophage and/or phage coat protein. The attachment of the polypeptide to the phage may be achieved through a direct fusion of the genes for the polypeptide to the gene of a phage coat protein, or it may be via a strong interaction between two separately expressed polypeptides. The attachment of libraries of proteins onto the surface of the head of lytic and lysogenic bacteriophage is known as "capsid display". An example of phage coat proteins that may be suitably adapted for fusion to the polypeptide are the genes for the 11 kD lambda D protein (Sternberg and Hoess, 1995; Mikawa et al., 1996), which decorates lambda bacteriophage heads, or the 25 kD lambda V protein (Maruyama et al., 1994), which is the tail sheath protein. Other lytic phages have also used polypeptide fusions to the 9 kD SOC protein of T4-like phages (Rao et al., 2007) and fusions to the C-terminus of the 42 kD T7 capsid protein, 10B (Dai et al., 2008). In the instance of the P2/P4 bacteriophage system, peptides have been displayed at the N-terminus of the 21 kD P4 Psu protein (Lindqvist and Naderi, 1995).

An exemplary method of capsid display is the fusion of peptides or polypeptides to the capsid protein, gpD, of lambda bacteriophage. This method has been described extensively in the literature (Sternberg and Hoess, 1995; Mikawa et al., 1996; Gupta et al., 2003; Vaccaro et al., 2006; Levy et al., 2007) and in U.S. Pat. No. 7,732,150 and U.S. Pat. No. 6,884,612.

The lambda gpD protein has been shown to tolerate fusions of polypeptides to either the N- or C-terminus (Mikawa et al., 1996) with a valency of up to ~400 per phage, although loading of higher than ~50% of fusion protein per head decreases the phage viability. Direct comparisons of lambda capsid display against filamentous phage display demonstrated superior fusion protein expression and capture efficiencies during target panning (Santini et al., 1998; Gupta et al., 2003). Although lambda capsid display would be of great utility in screening antibody libraries, it has only been cited as in use by three groups. Gupta et al. (2003) demonstrated that a single-chain antibody (scFv) productively folded and was approximately 100-fold more reactive by an ELISA assay than a filamentous-phage displayed antibody. Similarly, Vaccaro et al. (2006) found lambda to be an excellent platform display of a scFv. However, as shown by Vaccaro et al. (2006) this was due to the remarkable and rare stability of the scFv that had been chosen, which was able to be folded in the cytoplasm. These authors demonstrated that for other scFv sequences there was likely to be difficulty in obtaining productive display. Levy et al. (2007) acknowledged and made use of this fact in an attempt to use lambda display as a genetic screen to select for *E. coli* cytoplasmic proteins that would enhance productive folding of scFvs in the cytoplasm. Their result was only a very modest improvement in the productive folding of a scFv. The methods of the present invention can utilise a stable scFv scaffold, such as demonstrated by Gupta et al. (2003) and Vaccaro et al. (2006) in a capsid display system in a lysis-defective phage.

The are a number of advantages of using lysis-defective phage to both package the polynucleotide and display the encoded polypeptide on the capsid surface. Firstly, the phage capsid serves as a stable, endonuclease-protected encapsulation for the polynucleotide in a form that, once released, enables a high-yield of recovery (nearly 100% of packaged phage can be recovered). Secondly, the phage capsid serves as a stable and numerous binding site for the encoded polypeptide within the permeabilised cell. FIG. 25 demonstrates that this property can be utilised to directly visualise a scFv binding to its fluorescent target where the scFv is fused to the lambda gpD protein. Thus, the polynucleotide library packaged into a lysis-defective phage, and further encapsulated by the permeabilised cell may be used in the method of protein display of the invention. An example of display using this embodiment would be to screen for the binding of a fluorescently-tagged target to a capsid-displayed antibody or affinity scaffold, where the binding is detected using either fluorescence microscopy or using FACS. FIG. 25 demonstrates the positive identification of fluorescent target binding to encapsulated phage displaying a capsid-bound antibody using FACS.

A third advantage of library display and packaging using lysis-defective phage is that the failed release of the phage from the induced host cells enables the concentration of phage to high titres through centrifugation of the host cells, followed by permeabilisation using either detergent or chloroform, and induced lysis using purified lysozyme. The inventors can report that the titres of lambdoid phages can be increased 100-fold compared with liquid culture titres of lysed phage when the lysis-defective mutants of the phages are used for packaging. It is routine to achieve titres of >10$^{11}$ phage per mL of Readylyse (Epicentre)-lysed cells when phage are packaged using lysis-defective mutants. In order to achieve titres of this level requires laborious precipitation and ultra-centrifugation of the phage lysates, which risks the loss of surface-bound fusion protein during the long procedure.

Yet another enhancement of capsid display enabled by the method of the invention is that excess soluble capsid fusion protein that is not bound to the encapsulated phage particles may be easily removed by cellular permeabilisation. This feature is important for target binding to the encapsulated bacteriophage particles, as otherwise binding may occur in solution to the fusion protein that is not capsid-bound, and which is usually in excess. Without partition of the capsid-bound and soluble fusion protein the binding and/or capture of bacteriophage that display an affinity protein would be reduced.

Examples 20 and 23 describe the fusion of affinity proteins to both the Hy5 phage (a P2/186 hybrid with the P2 structural genes) and the lambda phage capsid proteins, gpL and gpD, respectively, and their demonstrated use in enrichment through a matrix-bound target.

The polypeptide to be screened need not be directly fused to the phage coat protein, instead it may expressed as a separate polypeptide that is linked in vivo to the exterior of the phage through a stable association of protein domains. An example of such an association may be the high affinity between a protein domain and a peptide ligand, such as observed between calmodulin and calmodulin-binding peptides (CBPs). Alternatively, the association could be established through a covalent interaction between two polypeptides. An example of this would be the SNAP and CLIP proteins (New England Biolabs) that would be separately fused as partners to the display protein and a bacteriophage coat protein, and a ligand that is covalently bound by both proteins.

DNA Binding Proteins

The present inventors have found that DNA is retained within a bacterial cell following permeabilisation. Thus, in one embodiment, the polypeptide is associated with a DNA-binding protein to form a protein complex that binds DNA and that is retained inside the bacterial cell. As used herein, "DNA-binding protein" refers to any protein comprising a DNA-binding domain comprising at least one motif that recognizes double-stranded or single-stranded DNA. As would be known to the person skilled in the art, DNA-binding domains include helix-turn-helix, zinc finger, leucine zipper, winged helix, winged helix turn helix, helix-loop-helix, immunoglobulin fold recognizing DNA, or B3 domains. Associating the polypeptide with a DNA-binding protein advantageously provides for enhanced recovery of DNA, for example a plasmid, encoding the polypeptide in the screening methods of the invention.

Examples of DNA binding proteins include bacterial competence proteins such as, but not limited to, *E. coli* DNA binding proteins, *Neisseria gonorhoeae* DNA binding proteins, for example ComE, Adenovirus E2 proteins, AraC transcription factor, basic helix-loop-helix transcription factors, basic-leucine zipper transcription factors, butyrate response factor, centromere protein B, COUP transcription factors, early growth response transcription factors, G-box binding factors, GATA transcription factors, HMGA proteins, homeodomain proteins, I-kappa B proteins, integration host factors, interferon regulatory factors, interferon-stimulated gene factor 3, Kruppel-like transcription factors, leucine responsive regulatory protein, matrix attachment region binding proteins, methyl-CpG-binding protein, MutS homolog 2 protein, myeloid-lymphoid leukaemia protein, NF-Kappa B, NF1 transcription factors, nuclear respiratory factors, oncogene protein p55, origin recognition complex, paired box transcription factors, POU domain factors, proto-oncogene factors, Rad51 recombinase, Rad52 DNA repair and recombination protein, replication protein A, replication protein C, retinoblastoma protein, Smad proteins, SOX transcription factors, T-box domain proteins, TCF transcription factors, telomere-binding proteins, Toll-like receptor 9, trans-activators, and winged-helix transcription factors. In one embodiment, the DNA binding protein is an *E. coli* DNA binding protein. In another embodiment, the DNA binding protein is a *Neisseria gonorrhoeae* protein, for example ComE, or a domain thereof.

Cell Wall Binding Proteins

The polypeptide that is being screened for a desired activity may be associated with a bacterial cell wall-binding protein. The skilled person will understand that the choice of a cell wall-binding protein would depend on the host cell species, as different bacteria have different cell wall compositions. While bacteria have cell walls made up of peptidoglycan (PG), chemical modifications between species can affect cross-species binding. The skilled person will readily be able to determine cell wall-binding proteins suitable for use in a particular bacterial species.

Bacterial cell wall-binding proteins include proteins known to have a domain structure, whereby part of the polypeptide chain in the native structure is able to recognise and bind specific molecules or molecular conformations on the bacterial cell wall. Thus, the term "bacterial cell wall-binding protein" includes a protein domain which is part of the protein which specifically binds to the bacterial cell wall. Examples of bacterial cell wall-binding proteins include the cell wall hydrolases as coded by bacteriophages, cell wall hydrolases of bacteria and different autolysins. Further encompassed are receptor molecules coded by the DNA of bacteriophages and other viruses. Where the bacterial cell wall-binding protein is from hydrolytic enzymes of bacteriophage origin, which are capable of specific binding to bacteria, the cell wall-binding protein maintain their binding ability but preferably have no significant hydrolytic activity.

In one embodiment, the cell wall-binding protein binds non-covalently to the cell wall of *E. coli*. For example, for an *E. coli* host cell there are endogenous PG-binding proteins with a conserved ~100 amino acid PG-binding domain occurring in PAL, OmpA, YiaD, YfiB, and MotB (Parsons et al., 2006). However, proteins from other organisms have been shown to be well expressed in *E. coli* and to bind the cell wall with high affinity, for example the ~70 amino acid PG-binding domain from *Pseudomonas* ϕKZ phage (KzPG) (Briers et al., 2009). Thus a PG-binding domain from a protein that binds PG may be used as a bacterial cell wall-binding protein in the methods of the invention.

In an exemplary embodiment, the PG-binding domain may be fused to the polypeptide that is being screened for a desired activity and expressed in the cytosol of the bacterial cell. Upon membrane permeabilisation, the PG-binding domain gains access to and binds the cell wall resulting in the retention of the polypeptide of interest within the permeabilised cell. To potentially further enhance retention of the polypeptide of interest within the cell, the skilled person will understand that the polypeptide may be associated with a DNA-binding protein in addition to a bacterial cell wall-binding protein.

Alternatively, the polypeptide of interest may be associated with a protein that is capable of linking covalently to the bacterial cell wall. Preferably the protein comprises a periplasmic-targeting signal. Thus, the polypeptide is expressed in the cytosol of the bacterial cell, but targeted to the periplasm where it is linked to the cell wall before membrane permeabilisation.

By way of non-limiting example, the bacterial cell wall-binding protein that attaches to the cell wall covalently may be a lipoprotein capable of binding to the cell wall and which lacks a functional N-terminal signal sequence necessary for outer membrane attachment. For example, the lipoprotein may be *E. coli* LPP. LPP is an abundant *E. coli* protein that forms a trimeric coiled-coil. In its native form, one end is tethered to the outer membrane via lipidation and the other is covalently bound to the cell wall via a C-terminal lysine. The lipoprotein may further comprise a sequence which targets the lipoprotein to the periplasm, for example an OmpF periplasmic targeting sequence. In one embodiment, the lipoprotein is *E. coli* lipoprotein lacking a functional N-terminal signal sequence necessary for outer membrane attachment.

In light of the teaching of the present specification, the person skilled in the art will be able to identify or design proteins that attach covalently to the bacterial cell wall and that are suitable for use in the methods of the present invention.

In one embodiment of the invention, the polypeptide being screened for a desired activity is a fusion polypeptide comprising a KzPG domain and one or more other domains selected from a spacer, SNAP and/or DBP. In one particular embodiment, the fusion polypeptide comprises one or more spacers and the KzPG, SNAP and DBP domains.

Spacers

In one embodiment, the polypeptide being screened for a desired activity may be expressed as a fusion polypeptide which comprises one or more spacers. A "spacer" as used herein refers a to peptide or polypeptide that may be included in a fusion polypeptide to enhance expression of the polypeptide in a bacterial cell or to decrease steric hindrance such that the polypeptide being screened for a desired activity may assume its desired tertiary structure and/or interact appropriately with its target molecule. Thus, the fusion protein may comprise one or more spacers before, after, or between one or more polypeptide domains in the fusion polypeptide. For spacers and methods of identifying desirable spacers, see, for example, George, et al. (2003).

In one embodiment, the spacer comprises one or more amino acid sequences that are between 1-50 amino acid residues in length, or about 1-25 residues, or about 5-15 residues in length. For example, the spacer may be selected from one or more of I27, RL1, RL2, RL3, RL4, RL5 and/or RL6. The person skilled in the art will understand that a limited number of amino acid substitutions, for example, 1, 2, 3, 4 or 5 amino acid substitutions may be introduced into the spacer without affecting its ability to function as a spacer. In one particular embodiment, the one or more spacers are selected from any one of SEQ ID NOs:6 to 12 or 16. Thus in one embodiment, the polypeptide being screened for a desired activity is a fusion polypeptide comprising I27, RL6, KzPG, SNAP and DBP.

In another embodiment, the spacer region may comprise a peptide sequence that is a high-affinity binding site for a protein domain. For example, calmodulin has a $Ca^{2+}$-dependent affinity for a number of peptide sequences from protein ligands that have been mapped to short peptide regions. These CBPs (Calmodulin Binding Peptides) have been mutated for even higher affinity binding to calmodulin (Kd's between ~1 nM to 1 pM) (Montigiani et al., 1996), enabling a $Ca^{2+}$ switchable, high affinity interaction between two proteins, one having a CBP spacer region and the other fused to calmodulin.

Screening Methods and Protein Evolution

The present invention provides methods for screening polypeptides for a desired activity against a target molecule. As used herein, the term "desired activity" refers to any potential useful activity of a polypeptide and includes, but is not limited to, binding, enzymatic modification, folding stability and/or thermal stability.

The term "target molecule" refers to a molecule that binds to and/or is modified by the polypeptide and may be for example an antibody, a receptor, an antigen, an enzyme etc. Thus, "target molecule" can be used to refer to a substrate such as an enzymatic substrate or a molecule that is being evaluated for binding (e.g., a ligand, epitope, antigen, multimerization partner such as a homo or hetero dimeric partner, etc., or any combination thereof).

It will be appreciated that polypeptide activities may be screened for or selected in the context of a single type of cell expressing a single polypeptide, or in the context of a library of cells each expressing a different polypeptide or polypeptide variant. Thus, the methods of the present invention may be used for in vitro protein evolution. In vitro protein evolution allows for a large number of protein functions and characteristics to be investigated and typically comprises two main steps: diversification and selection. Diversification relies on the ability to generate diverse libraries of nucleic acids coding for polypeptides. Selection can be achieved by screening the libraries for a desired activity and linking the activity to the genotype, for example, by identifying the member of the library that comprises the genotype that is responsible for the observed activity.

DNA libraries are a collection of recombinant vectors containing DNA inserts (DNA fragments) that encode a polypeptide. The origin of the DNA inserts can be genomic, cDNA, synthetic or semi-synthetic. The polypeptide may have any desired activity, for example the polypeptide of interest may be a binding protein, for example an antibody, or an enzyme for example, a polymerase, ligase, restriction enzyme, topoisomerase, kinase, phosphatase, metabolic enzyme, catalytic enzyme, or a growth factor hormone, antimicrobial peptide, antigen, receptor, reporter protein, immunomodulatory protein, neurotransmitter, structural protein, transcription factor or transporter. In one embodiment, the polypeptide is an antibody or an enzyme. Thus, the methods of the present invention can be used for screening for variants of a polypeptide having a desired activity.

The cloning and construction of DNA libraries of, for example, binding proteins or enzymes, can be performed using methods known in the art. For example, Lutz and Patrick (2004) have reviewed methods of generating library variability and strategies for gene recombination for use in protein engineering. For screening of displayed polypeptide variants, the strategies used for surface-displayed libraries could be adopted and adapted for the methods of the present invention (Becker et al., 2004; Daugherty et al., 2000; Kenrick et al., 2007; Miller et al., 2006).

A library of nucleic acids can be introduced into a plurality of bacterial cells resulting in the expression of a member of the library in each of the bacterial cells. In addition to being expressed, the polypeptides are retained within the permeabilised bacterial cell, or attached to the cell wall, in order to evaluate their function or characteristic. Nucleic acid libraries of a polypeptide, for example, a binding protein such as an antibody, or of an enzyme, can be generated through a variety of methods including through the introduction of mutations such as point mutations, deletions, and insertions, or through recombination events. Methods for the generation of libraries of variants are known in the art and include error-prone PCR, synthesis of DNA in DNA repair compromised bacteria, and chemical modification of DNA. Methods for the generation of libraries through recombination are known in the art and include gene shuffling, assembly of DNA in highly recombinogenic bacteria, synthetic nucleic acid library assembly, etc., or any combination thereof. In this way a library of polynucleotides encoding polypeptides can be introduced into a plurality of bacterial cells resulting in the expression of one or members of the library in each of the bacterial cells.

In some embodiments, a library comprises two or more variants of a polypeptide wherein each variant comprises a unique polypeptide with a minor change in amino acid sequence. In other embodiments, a library comprises two or more unrelated sequences. For example, to identify a candidate polypeptide that can inhibit an enzyme, a library of random sequences or predetermined sequences may be interrogated. A library can have at least 2, at least 5, at least 10, at least 50, at least 100, at least 1000, at least 10,000, at least 100,000, at least 1,000,000, at least $10^7$ or more members.

Binding Protein Display

In one embodiment, the methods of the present invention are applied to the evolution of binding proteins, such as for example antibodies. Thus, in one embodiment, the polypeptide that is screened for a desired activity is a binding protein, the target molecule may be any molecule to which the binding protein may bind, and the desired activity is binding, and/or the extent of binding to the target molecule. The methods of the invention may comprise, for example, culturing a bacterial cell comprising a polynucleotide encoding a binding protein so that the protein is produced in the cell. The cell is subsequently permeabilised and the permeabilised cell contacted with a target molecule. Any suitable method in the art may be used for determining if the polypeptide binds, and/or the extent of binding to, the target molecule.

The methods of the invention are particularly suited to the screening of binding protein display libraries. Unlike other methods of in vivo surface display, which absolutely require the targeting of the protein to an extracellular space as the cellular membranes prevent interaction with the labeled target presented to the display protein, the methods of the invention can express and fold the affinity proteins in the cytoplasm of the host cell. Thus, the screening parameters can include the high yield and productive folding of the affinity variant protein in the cytoplasm of bacteria.

Furthermore, as cytoplasmic protein expression and folding is in a reducing environment, the methods of the invention can be applied to select for variants of antibodies, or other proteins that have disulphide bonds in their native form, that can productively fold in a reducing environment. The variants selected would be expected to be more stable as they would not be reliant on intra- or inter-domain disulphide bonds for folding stability. This approach has application towards the development of antibodies that could be used for intracellular binding of targets, to either neutralize or label.

The methods of the invention can therefore be used as a platform for the display and selection of a variety of binding proteins, including those scaffolds known to the art, such as single-chain antibodies (scFv), domain antibodies, Fab, and the non-antibody scaffolds such as lipocalins, FN3, ubiquitin, γ-B-crystallin.

Polypeptide Screening in Combination with Phage Display

Conventional phage display, with the polypeptide being screened attached to the surface of a filamentous phage, generally in only one or a few copies, enables the screening of large numbers of clones in parallel for affinity to a target molecule. However, the background of low- and moderate-affinity clones is high and unique clones cannot be distinguished without subcloning and sequencing, and the determination of the properties of each unique clone (for example, expression levels, solubility and affinity) usually requires a change in the format of expression. Thus, in prior art methods a substantial amount of work lies downstream from the initial phage display screen.

In comparison, the methods of the invention allow the use of FACS to characterise polypeptides within, or attached to, Gram-negative bacterial cells. FACS enables the binding parameters to be defined resulting in clones with the desired characteristics being highly enriched. However, the screening of individual clones is sequential and even with sort rates of $10^4$ clones per second there is a comparatively low upper limit on the number of individuals which may be processed in one screen. For example, screening $10^8$ clones could take over 2 hours.

Thus, in certain circumstances it may be desirable to combine the parallel screening of conventional phage display systems with the clonal characterisation of cellular display analysed by FACS as provided by the present invention. Hence, early screens may be performed by conventional phage display, with the output clones being subsequently analysed by the display system of the present invention in which the polypeptide is retained within the bacterial cell by the cell wall and/or by attachment to the cell wall, or by attachment to an encapsulated lysis-defective phage.

Thus, a gene library can be expressed and displayed on the surface of a lytic phage or filamentous phage using fusions to phage proteins, or through stable association of two polypeptides as described herein. These phage can be screened for activity of the polypeptide ('panning') using standard techniques for bacteriophage display. Phage displaying the fusion protein that adhere to a target molecule, such as an affinity substrate, can be produced and recovered as, for example, cosmids by infection into the helper strain containing the prophage lysogen. This cycle can be iterated until the library is dominated by enriched clones. At this point, the library could be subcloned into a vector system that performs encapsulated display according to the method of the invention.

Accordingly, in one embodiment of the present invention, an additional screening step is performed before and/or after the screening method of the invention. As outlined above, the additional screening involves a conventional phage display system, i.e., a phage display system in which: i) the polynucleotide encoding the polypeptide being screened for a desired activity is not packaged into a lysis defective-phage, and/or ii) the polypeptide is not retained within the bacterial cell by the bacterial cell wall and/or attached to the bacterial cell wall. Such additional screening may involve known methods of phage display such as the use of lytic lambda phage or filamentous M13 phage.

In a further embodiment of the method of the invention, the conventional phage display method can be combined with the use of the lysis-defective phage and encapsulated cellular display to enable the facile switching between the two forms of protein display, without further subcloning of the DNA of the enriched library.

In this embodiment, the protein to be displayed may be encoded as a fusion to a phage capsid protein by a polynucleotide cloned into a lysis-defective bacteriophage or phagemid, or into a cosmid that is packagable by a prophage. Methods for constructing a bacteriophage vector for capsid display such as a lambda vector are described in Mikawa et al. (1996), Sternberg and Hoess (1995), and Vaccaro et al. (2006). Methods for the construction of phagemid and cosmid vectors are also well known in the art. For example, phagemid vectors based on the pUC and pBR322 origins were described by Yankovsky et al. (1989) and King et al. (1982), respectively. For lambda cosmids, Sambrook and Russell (2001), and for P2/P4/186 cosmids, Kahn et al. (1991), both provide good general descriptions and details of vectors. The cosmid will be transformed into a bacterial cell line containing a lysis-defective prophage and induced for both expression of the capsid fusion protein, and packaging of the cosmid vector.

Alternatively, the lysis-defective bacteriophage vector is transformed/infected into a host cell and similarly induced for expression of capsid fusion protein and the bacteriophage vector genome.

Following packaging of the bacteriophage/cosmid vector the cells may be lysed to release the packaged phage by the combined treatment of a permeabilisation step using detergent or an organic solvent such as chloroform, and an enzymatic lysozyme activity, such as available commercially as ReadyLyse (Epicentre). The display library may now be 'panned' for binding to a target by methods commonly used for phage display selection. Following panning, the library may be recovered by re-infection into the bacterial host containing the lysis-defective prophage. Cycles of panning and re-infection may be iterated until the proportion of binding phage is substantially enriched in the library population at which point the next cycle of phage production the cells are permeabilised, but the enzymatic lysis step is omitted, thus producing a sub-library of encapsulated phage. A fluorescently-labelled target may be bound to these encapsulated phage which may then be sorted by FACS, as described in Example 23 and observed for FIG. 25.

The person skilled in the art will appreciate that this embodiment, provides for the display library to be moved between two different modes of display; 1) panning of free phage to immobilised target which is a highly-parallel screen with low clonal selectivity; and 2) FACS characterisation and purification of encapsulated individual clones, which is a highly-selective but low-throughput screen. Thus, this embodiment of the method of the invention enables the ability to utilise the most powerful elements of each system without the user intervention for reformatting which would otherwise be required. Such an embodiment is therefore highly amenable to a robotic, high-throughput, workflow.

In another embodiment of the method of the invention, soluble antibodies may be identified and utilised as scaffolds in gene libraries that can be switched between phage display and Gram-negative bacterial cellular display by the method of the invention.

Enzyme Display

The methods of the invention can be used for the display of enzymes and enzyme libraries and for the evolution of enzyme properties. Thus, in one embodiment, the polypeptide that is screened for a desired activity is an enzyme, the target molecule is a substrate of the enzyme, and the desired activity is binding to and/or enzymatic modification of the target molecule. The skilled person will understand that methods for the development of assays for enzyme activities using other surface display technologies could be equally applied as assays to the methods of the invention.

The methods of the invention would also be well suited in the use of enzyme libraries that are expressed in the host cell, which is permeabilised and then suspended as a water-in-oil-in-water emulsion (w/o/w). Aharoni et al. (2005) demonstrated the utility of using cell surface-displayed enzyme libraries in a w/o/w emulsion by FACS for the improvement of paraoxonase. The advantages of encapsulation in a non-permeable oil membrane are that a diffusible substrate and product can be kept in proximity to the enzyme activity and coding nucleic acid sequence. However, the screen described by Aharoni et al. (2005) requires that the enzyme be displayed on the exterior of the host cell. Using the methods of the invention, intracellular expression and folding of enzyme libraries could be used for the improvement in enzyme function.

In the methods of the invention, a bacterial cell comprising a polynucleotide encoding an enzyme is cultured in order to produce the enzyme. Following permeabilisation of the bacterial cell, the cell is contacted with a substrate of the enzyme and known methods may be used to determine if the enzyme modifies, and/or the rate of enzymatic modification of, the substrate.

In some instances, it may be desirable that the target molecule (for example an enzyme substrate) is linked to the bacterial cell. The skilled person will understand that the target molecule may be linked to any component of the permeabilised bacterial cell, either directly or indirectly. Direct linking may be achieved, by way of non-limiting example, by linking the target molecule to the bacterial cell wall. Indirect linking of the target molecule may be achieved, for example, by linking the target molecule to the second polypeptide that is associated with the polypeptide being screened for a desired activity to form a protein complex. For example, the target molecule may be linked to the polypeptide having a molecular size sufficient to retain the protein complex inside the permeabilised bacterial cell, or it may be linked to the DNA-binding protein, or to the bacterial cell wall-binding protein as used in the methods of the invention. Linking the target molecule to the bacterial cell advantageously enables the isolation of bacterial cells presenting active enzymes using technologies such as, for example, FACS or by magnetic bead selections.

The person skilled in the art will readily be able to determine a coupling chemistry suitable for linking a target molecule to a bacterial cell. Suitable coupling chemistries include cysteine labelling with thiol coupling reagents such as acrydite and maleimide, amine labeling, and carboxyl labeling which are commercially available from suppliers including Pierce Protein Research Products and Invitrogen.

Flow Cytometry Analysis

The cellular display technology of the present invention may present many thousands of molecules of a polypeptide of interest at once and, unlike molecular display technologies such as ribosomal/mRNA display or phage display, may be screened using flow cytometry techniques, for example using fluorescence activated cell sorting (FACS) machines. Not only can positive events in the library be captured but parameters such as protein expression, enzymatic activity or target affinity can be simultaneously defined for each positive member, thereby improving the output of the screen. Instruments for carrying out flow cytometry are known in the art and include FACS Star Plus, FACScan and FACSort (Becton Dickinson), Epics C, and MoFlo. Flow cytometric techniques in general involve the separation of cells in a liquid sample. Typically, the purpose of FACS is to analyse the cells for one or more characteristics, for example, the presence of a target molecule. Methods for performing flow cytometry analysis are well known in the art. For example, a review of methods using FACS for assaying enzyme activity is described by Farinas (2006).

For the present invention, flow cytometry is useful for multiple rounds of screening that can be carried out sequentially. Cells may be isolated from an initial round of sorting and immediately reintroduced into the flow cytometer and screened again to improve the stringency of the screen. Since flow cytometry is essentially a particle sorting technology, the ability to culture cells is not necessary. Techniques for the recovery of nucleic acids from non-viable cells are well known in the art and may include, for example, template-dependant amplification techniques including PCR.

After a Gram-negative bacterial cell has been identified that produces a polypeptide having a desired activity, DNA encoding the polypeptide may be isolated from the bacterial cell using any suitable known technique. Thus, the DNA encoding the polypeptide may be isolated and sequenced using conventional procedures. If desired, the polynucleotide may go through another round of diversification in order to generate another library of variants to be screened for the desired activity. In this way it is possible to use an iterative process to optimise the desired activity of a polypeptide.

In embodiments where the polynucleotide is packaged by a lysis-defective phage, the polynucleotides encoding the polypeptide members of the library having a desired activity may be easily and rapidly recovered from the post-FACS screen for further iterative enrichment or for clonal analysis by recovery of the packaged phage library, or cosmid library, by treatment of the permeabilised bacterial cells with a lysozyme, for example, ReadyLyse (Epicentre), to degrade the cell wall and release the phage for subsequent infection.

Thus, this embodiment of the invention allows for the concurrent characterisation of expression and binding parameters with FACS screening, together with the facile recovery and handling of phage-packaged gene libraries. Iterative rounds of FACS screening using lysis-deficient phage libraries are therefore simplified and do not rely on PCR-amplification of positive clones with both the attendant mutational error and handling required.

Packaging Gene Libraries Using Lysis-Defective Phage

The present inventors have found that using an inducible lysis-defective prophage allows for high efficiency cloning and packaging of a gene library in Gram-negative bacteria. An inducible prophage is one that is present in the genome of a Gram-negative bacterial cell, wherein upon inducing activation of the prophage, the prophage is activated as a phage in the bacterial cell. The phage in the cell may then be capable of packaging a polynucleotide.

The polynucleotides encoding the proteins to be screened by the display methods of the invention may be packaged into phages that have a lytic stage, or alternatively into a lysis-defective phage. Both lytic and lysogenic phage genomes generally have a region that is dispensable for either lifecycle, and may be replaced with a cloned gene and associated regulatory regions. Dispensable regions may include regions containing genes for DNA recombination (for example, the lambda bacteriophage bet and exo genes and Nin5 region), or regions that provide host cell survival functions to a lysogen (for example, the lambda phage Ea47, Ea31, Ea59, Lom and bor genes; the P2 phage Old, and Fun genes). Alternatively, there may be a tolerance for packaging of genomes that are fractionally larger than normal (for example, Lambda bacteriophage will package up to 105% of the wild-type length of 48.5 kb) enabling cloning of short regions directly into the genome without replacement of nonessential regions, such as in the T7 Select Phage display system (Novagen). When the gene library is to be cloned into a lysis-defective bacteriophage vector, the lysis genes also represent a dispensable region.

Where possible, the polynucleotide encoding the polypeptide being screened for a desired activity should be cloned into a region of the phage genome such that it does not disrupt the transcription and translation of essential operons of the bacteriophage. Thus, the skilled person will understand the polypeptide may be expressed using its own transcriptional regulatory regions such as, for example, its own promoter and/or terminator.

Gene libraries of the polypeptides to be screened for a desired activity may also be constructed using elements that instruct a helper phage to package a plasmid as an infectious phage particle. For example, the cos regions of bacteriophages Lambda, P2, P4 and of other lambdoid phages are <500 bp elements that have the binding and cleavage sites for the terminase enzyme, which cuts and packages a plasmid containing these regions as a linear element within a phage capsid head. These cos regions can be cloned into a plasmid that is then referred to in the art as a cosmid. In general, the size of a cosmid must be close to the size of the wild-type genome, usually within 80 to 105% of the wild-type phage genome, to be packaged efficiently. Alternatively, it may be a unit fraction of the wild-type genome (½, ⅓, ¼) with multimers of the cosmid being packaged within a single phage head. The multimers may be formed within the cell by recombination between cosmids in a recA$^+$ cell, or may be formed during the replication cycle of bacteriophage (e.g. rolling circle replication by lambda bacteriophage).

The P2 phage, or the related 186 phage or hybrid of 186 and P2, and its satellite, P4, advantageously provide a cosmid of a manageable size for plasmid-based cloning techniques (~11 kb) and the P2 terminase protein has a preference for packaging plasmid substrates containing a single cos region, rather than linear multimers with adjacent cos regions, as the Lambda terminase prefers. Thus a cosmid library can be constructed with ease and packaged in vivo with high efficiency. Methods for the packaging of gene libraries using a P2 phage are described in Kahn et al. (1991).

Phage libraries made using lytic bacteriophage (for example, T7 Select) may be packaged in vivo following infection of a host cell. Where the phage is lysis-defective, the cell will remain intact until permeabilised and screened by the method of the invention. The infectious phage may then be recovered from selected cells by treatment with lysozyme to degrade the peptidoglycan and release the phage particles.

Phage libraries made using lysogenic bacteriophage or their cosmids are packaged in vivo by inducing activation of an integrated prophage or by infection of a helper phage to produce phages and to enter the lytic pathway. Prophage induction is commonly achieved using temperature sensitive mutants of the phage immunity repressor protein. Libraries may be established in the host cell at the low temperature, and then bacteriophage packaging induced by an upward temperature shift. For example, the cI857 allele of the repressor gene of the lambda phage supports establishment and maintenance of lysogeny at 30° C., but is inactive at temperatures higher than 37° C., forcing prophage excision and entry into the lytic pathway. However, the P2 phage, which is known as a non-inducible phage, can not be induced by standard methods such as UV or a temperature-sensitive repressor. Instead, P2 functions can be induced by a helper phage for cosmid packaging by using infection of the P4 satellite, in particular, vir mutants of P4 that prevent establishment of a P2/P4 co-lysogen, but instead activate P2. However, the P2-related phage, 186, does not have a temperature-sensitive repressor, cIts, that can induce phage replication and packaging upon inactivation (Woods and Egan (1974)). Furthermore, hybrid phage of P2 and 186 were obtained by coinfection that contain the temperature-inducible replication control of phage 186 with the structural genes of P2. One such phage is known as Hy5 (Younghusband et al., 1975).

Elements of P2 and P4 that regulate the P2 lytic pathway may also be cloned and induced to trigger lysis. Example 17 details the use of the transcription factors P4 δ, P2 cox and P2 ogr genes to induce lysis and cosmid packaging in an *E. coli* C strain P2/P4 co-lysogen. The lambda phage cI857 repressor was used with its endogenous promoter and the operator region of the cro gene to regulate the expression of the P2 and P4 transcription factors. The δ gene was the most rapid activator of lysis, followed by the ogr and cox genes, in that order. Cellular lysis was accompanied by the release of infectious P4 phage and cosmid particles.

Other P2 control genes that may induce P2 activation include the entire P4 sid-δ-psu operon and the P4ε anti-repressor, or combinations thereof.

A cosmid library transformed into cells containing a P2 helper phage with a co-lysogenic P4 helper phage, and/or the P4 control regions described above, may be packaged in vivo following induction of P2 activation. Where the phage is lysis-defective, the cell will remain intact until permeabilised and screened by the method of the invention. The infectious cosmid phage particles may then be recovered from selected cells by treatment with lysozyme to degrade the peptidoglycan and release the phage particles.

Kits

The necessary components for performing the methods of the invention may conveniently be provided in the form of a kit. As will be understood to a person skilled in the art, the various components in the kit may be supplied in individual containers or aliquots, or the solution components may be combined in different combinations and at different concentrations to achieve optimal performance of the methods of the invention. It is within the knowledge of the skilled addressee to determine which components of the kit may be combined such that the components are maintained in a stable form prior to use.

In one embodiment, the kits of the invention will typically at a minimum contain a vector which comprises a site for inserting into the vector a polynucleotide encoding a first polypeptide, and an open reading frame encoding a second polypeptide which associates with the first polypeptide to form a protein complex that is retained inside or attaches to the cell wall of a permeabilised bacterial cell. Preferably, the kit also contains an agent for permeabilising a bacterial cell. In one embodiment, the kit further comprises bacterial cells, preferably Gram-negative bacterial cells. Other additional components may be included with the kit, or other components supplied by the end user, if required.

The invention also provides kits suitable for use in methods of screening a protein for a desired activity which utilise a lysis-defective phage. Such kits will typically comprise at a minimum a Gram-negative bacterium comprising a lysis-defective phage together with a temperature-sensitive phage repressor protein and/or a polynucleotide encoding one or more phage activator proteins. In one embodiment, the kit comprises a lysis-defective phage selected from P2, 186, Hy5 and/or P4. In another embodiment, the kit comprises a lysis-defective lambda phage. The kit may optionally comprise an agent for permeabilising a Gram-negative bacterial cell.

EXAMPLES

Example 1

Screening for Detergents that Permeabilise *E. coli*

To identify detergents that would permeabilise *E. coli* cells, we screened a number of detergents, both ionic (n-dodecyl-β-iminodipropionic acid; decyltrimethylammonium chloride; sodium dodecanoyl sarcosine; anzergent 3-10) and non-ionic (dimethyloctylphosphine oxide [Apo8]; dimethyldecylphosphine oxide; n-octyl-β-D-thioglucopyranoside [8TGP]; sucrose monododecanoate; Mega10; Tween 80; Triton X100; Triton X114), both for the uptake of the membrane-impermeable dye, Gel Red (Biotium, cat. no. 41002) and for the release of GFP. The detergents tested for permeabilisation were purchased from Anatrace.

The *E. coli* host strain used in all reported experiments was the K12-derived Argentum (Alchemy Biosciences) cell line (ΔmcrA Δ(mrr-hsdRMS-mcrBC) ΔendA lacZΔM15). However, the method of the invention was also tested, with comparable results, with the B-strain-derived BL21 (F– dcm ompT hsdS($r_B$– $m_B$–) gal) and with the K12 cloning strain DH5α (F⁻ endA1 glnV44 thi-1 recA1 recA1 gyrA96 deoR nupG Φ80dlacZΔM15 Δ(lacZYA-argF)U169, hsdR17($r_K^-$ $m_K^+$), λ–).

GFP was cloned into an arabinose-inducible, high copy-number vector (pAra1::GFP5). Expression was from a culture heavily inoculated from a plate with freshly-streaked colonies. The culture was grown at 37° C. until an OD600 of ~0.3 when expression was induced by the addition of arabinose to a final concentration of 0.2%. The induced culture was shaken at 25° C. for 2 hours before harvesting.

Cells were pelleted from 1 mL of induced culture by centrifugation and permeabilised by suspension in 300 μL of 0.5% detergent in LB and incubated at 25° C. for 10 minutes. The permeabilised cells were pelleted and resuspended in 1× Gel Red in water for 2 minutes before being pelleted and washed once in 300 μL of TBS. They were suspended in 300 μL of TBS and processed for fluorescence microscopy by the addition of DABCO/glycerol (0.0325 g DABCO dissolved in 900 μl glycerol+100 μl PBS).

Samples were visualized on either an Olympus Provis AX70 Light Microscope with a Slider Camera (SPOT RT 2.3.0 Software v4.6), or a Leica TCS SP2 Confocal Scanning Laser Microscope/Leica DM IRE2 Inverted Microscope (Leica Confocal Software v2.0).

FIG. 1 shows the result of detergent permeabilisation with GFP-expressing *E. coli*. Whereas untreated cells are green (GFP), cells that have been permeabilised lose their internal GFP and take up the DNA-binding Gel Red dye to be stained red. While nonidet-40 shows some permeabilisation, Apo8 and Mega10 display a higher proportion of cells that have been permeabilised. A blend of these two detergents at 0.5% each, named Agent 86, demonstrated almost complete permeabilisation, as did another detergent, n-octyl-β-D-thioglucopyranoside (8TGP). Mega10, Apo8 and 8TGP are all non-ionic detergents, which are less disruptive than ionic detergents to protein folding and function.

As the cell wall remained intact following permeabilisation, soluble protein extracts of the supernatant from the detergent permeabilisation described above were analysed by SDS-PAGE. Hen egg-white lysozyme (Boehringer Mannheim; 837 059) was also added to a final concentration of 2 mg/mL to a sample of the cells being permeabilised to remove the cell wall and release the total cellular proteins. SDS-PAGE loading dye with β-mercaptoethanol was then added to the samples, which were denatured at 95° C. for 2 minutes. 20 µL of samples were loaded onto a 9% SDS-PAGE and stained/fixed with Coomassie Brilliant Blue/methanol/acetic acid.

FIG. 2 shows that the release of soluble protein directly correlates to the release of GFP and intake of Gel Red as observed by microscopy. Significantly, there were differences between the release of protein from cells with intact cell walls compared to those whose cell walls were removed using lysozyme, with the cell-wall encapsulated cells releasing soluble protein up to a size of ~120 kD. This is presumably the cut-off size above which globular proteins are unable to leave the cell through the pores of the peptidoglycan lattice that constitutes the cell wall of Gram-negative eubacteria.

Example 2

Screening for Permeabilisation Solutions that Retain Host DNA

If the method of the invention is to be used for screening gene libraries for protein variants with improved properties, there must remain a linkage between the expressed protein and its coding nucleic acid. As the membrane permeabilisation step removes the barrier that prevents DNA loss through the cell wall, conditions for permeabilisation were examined that might reduce or prevent host DNA loss.

Permeabilisation of cells using 0.5% 8TGP was conducted in different media and the loss of DNA was examined by fluorescence microscopy using the DNA-binding dye, Gel Red.

Compositions of permeabilisation media tested (all media with 0.5% 8TGP):
LB media (10 g tryptone, 5 g yeast extract, 10 g NaCl per Lt)
LB [−salt] media (10 g tryptone, 5 g yeast extract per Lt)
50 mM Tris, pH 7.5
50 mM Hepes, pH 7.0
170 mM NaCl
250 mM NaCl
25 mM Tris, pH 7.5+1.5% PEG 6000 (w/v)
50 mM Tris, pH 7.5+3% PEG 6000 (w/v)
50 mM Tris, pH 7.5+170 mM NaCl
50 mM Tris, pH 7.5+250 mM NaCl An optimal media for permeabilisation was identified as LB bacterial media.

Accordingly, permeabilisation was henceforth conducted using either 0.5% 8TGP in LB or Agent 86 in LB (0.5% Mega10 and 0.5% Apo8 in LB).

Example 3

Protein Fusions to a Tetramer Scaffold

As was observed by the experiments reported in Example 1, proteins larger than ~120 kD in size were retained within permeabilised E. coli cells by the cell wall. Therefore, it was reasoned that a protein of interest that was smaller than 120 kD would be retained within the cell wall capsule if, by fusion to a protein partner, the total size could be made to exceed 120 kD.

Accordingly, we cloned 6 different tetrameric proteins from E. coli for use as fusion partners. These were β-gal, BetB, GSK, GshB, RhnA, and YdcW, that had monomeric sizes of 116 kD, 52 kD, 39 kD, 35 kD, 47 kD and 50 kD respectively.

An arabinose-inducible high copy vector was built for tetrameric expression. The SNAP tag (NEB/Covalys), a 20 kD domain that covalently binds a fluorescent substrate, was cloned upstream of the tetramer genes and used as a expression reporter. A 6×His epitope was also included at the N-terminus of the fusion protein to facilitate purification or detection.

The sequence of the arabinose vector, pAra3::His6::SNAP, is provided as SEQ ID NO:1.

Fusion protein expression was induced with the addition of 0.2% arabinose, and the culture incubated at 25° C. for 2 hours.

To permeabilise the cells for protein display by the method of the invention, the protocol was as follows:
1. Pellet 1 ml of cells by centrifugation
2. Resuspend cells in 300 µL of 0.5% 8TGP/LB
3. Incubate at 25° C. for 10 minutes
4. Pellet cells by centrifugation
5. Resuspend cells in 200 µL of TBS or LB To label the SNAP expression reporter domain with the membrane-impermeable SNAP dyes (Covalys/New England Biolabs), the protocol was as follows:
1. Dissolve 20 nmol of BG-488 (green dye) or BG-547 (red dye) in 300 µL DMSO as a 200× stock
2. Add 1 µL of 200× stock to 200 µL of permeabilised cells suspended in TBS or LB
3. Incubate at 25° C. for 15 minutes
4. Wash cells twice by pelleting by centrifugation and resuspending in 300 µL TBS To view the tetrameric fusion proteins by fluorescence microscopy for retention within the permeabilised cellular capsule, the protocol was as follows:
1. Drop 20 uL of cell suspension onto a glass microscope slide, cover with coverslip and seal edges with nail polish (wet mount); alternatively, allow the cell droplet to almost dry, drop 20 µL of DABCO/glycerol on top, cover with coverslip and seal edges with nail polish (dry mount)
2. Visualise sample using either Olympus or Leica fluorescence microscope Expression of the full-length fusion protein was confirmed by Western blot of protein extracts run on SDS-PAGE gels and probed with α-His6 antibody. All tetrameric constructs expressed in E. coli at detectable levels (FIG. 3A).

Fluorescence microscopy of the tetrameric fusion proteins expressed in E. coli found that β-gal and G5K had significant inclusion bodies and low fluorescence, presumably due to difficulties in folding of the fusion protein. However, as shown by FIG. 4, expression of the fusion protein, as judged by SNAP fluorescence, was good for GshB, and excellent for RhnA, BetB and YdcW. It was noted that the distribution of the fusion protein in the permeabilised host cell was not homogeneous, with foci evident both by bright-field microscopy and fluorescence. However, as the fluorescent SNAP substrate would not be bound by a misfolded domain, and as the signal was very intense, it is thought that these bodies are likely to be aggregates of folded protein, and not inclusion bodies of unfolded protein which are frequently observed when over-expressing proteins in E. coli.

The SNAP::tetramer fusions also had a His6 N-terminal epitope. To test whether a large molecule such as an antibody would be able to penetrate through the lattice structure of the E. coli cell wall permeabilised cells were probed with αHis antibody to detect the SNAP::tetramer fusion.

1. Expression and permeabilisation of the His6::SNAP:: BetB scaffold fusion was performed as described above.
2. Labeling with the BG-547 SNAP ligand was performed as described above.
3. 200 µl of permeabilised, SNAP-labeled cells were washed three times in LB and allowed to settle onto a polyethyleneimine (PEI)-coated coverslip. Excess cell media was removed by aspiration and the slides allowed to air dry.
4. Cells were blocked for one hour in blocking buffer (1% BSA, 1% cold-water fish gelatin (Sigma, G7765), 0.02% Azide in PBS-Tween20).
5. Cells were incubated overnight at 25° C. in αHis primary antibody (Abcam, AB9136-100), diluted 1:10 in blocking buffer.
6. Cells were washed 3× in PBS-Tween20 (10 min each).
7. Cells incubated in secondary antibody diluted 1:2,000 (Molecular Probes, A11015) in blocking buffer for 1 hour at room temp.
8. Cells washed 3× in PBS-Tween20.
9. Mounted in DABCO/glycerol and viewed under the confocal/Olympus microscope.

FIG. 5 shows that the αHis antibody co-localised with the SNAP fluorescent ligand within the cell wall capsule, indicating that the pores of the cell wall are wide enough to allow diffusion of a relatively large protein into the inner capsule volume. Thus, even quite large protein ligands may be used as affinity substrates for affinity proteins expressed in the cytoplasm according to the method of the invention.

The SNAP fusion partner and expression reporter was compared with the HALO protein (Promega) in an attempt to see if the formation of the sub-cellular bodies was altered. The HALO protein covalently binds a membrane-impermeable fluorescent substrate (Alexa fluor 488; G1001, Promega) similarly to SNAP. The HALO reporter gene was cloned in frame directly into the place of the SNAP gene in the tetrameric expression constructs. Expression of the HALO::tetrameric scaffold proteins was compared to the SNAP variants. Labeling of the permeabilised HALO cells was conducted essentially as described for SNAP, and following the manufacturer's instructions. FIG. 6 shows that the expression patterns of the HALO::tetramers and the SNAP::tetramers was found to be similar, with the exception that the HALOS RhnA fusion protein was fractionally more soluble than the SNAP::RhnA fusion, with fewer cells containing fluorescent foci.

Therefore, expressing a protein as a fusion to a tetrameric scaffold (in this example, SNAP or HALO), and then permeabilising the E. coli host cell with a suitable detergent enables retention of the protein of interest inside the cell wall.

Example 4

DNA Binding Proteins as a Cellular Scaffold

To couple the phenotype to genotype, the host cell must retain at least some episomal DNA following permeabilisation and throughout the functional screen. Having identified permeabilisation conditions that retained the host genomic DNA, as well as plasmid DNA, we reasoned that DNA could be used as a retaining scaffold for the expressed protein of interest.

We therefore cloned a small (80 aa) high-affinity helix-hairpin-helix DNA binding protein (DBP) from the Neisseria gonorrhoeae ComE gene (Chen and Gotschlich, 2001) and fused it to the C-terminus of GFP in an arabinose-inducible construct (pAra3::GFP::DBP; seq 2).

Expression by arabinose induction was conducted as described for Example 1. Cells were permeabilised and prepared for fluorescence microscopy as described for Examples 1 and 3.

FIG. 7 shows that the GFP::DBP fusion (green) was retained in permeabilised cells and co-localised with the DNA-binding dye, Gel Red (red).

Therefore, expressing a protein as a fusion to a high-affinity, non-specific DNA-binding protein, and then permeabilising the E. coli host cell with a suitable detergent enables retention of the protein of interest within the cellular capsule.

Example 5

DNA Retention in Permeabilised Cells

To demonstrate the retention of DNA, both genomic and episomal plasmid, within the cellular capsule following permeabilisation, we prepared cells expressing GFP5::DBP and His6::eGFP for fluorescence microscopy and plasmid DNA extraction.

Following induction, cells were permeabilised then either frozen or left in TBS at 37° C. with shaking overnight. All samples were processed the following day for either fluorescence microscopy, to visualize GFP and the capsule DNA content by the DNA-binding dye Gel Red, or a plasmid DNA preparation was conducted.

Fluorescence microscopy was performed as described for Example 3. FIG. 8 shows that both the host cell DNA (red) and the GFP5::DBP (green) were retained in the cellular capsule immediately following permeabilisation and also with overnight incubation at 37° C., without any apparent loss. The His6::GFP protein was lost from cells following permeabilisation, but the host cell DNA (red) was still retained both following permeabilisation, and also overnight, again without apparent loss. To confirm that the plasmid DNA, and not just the host genome, was retained within the permeabilised cells, plasmid mini-preparations were conducted on identically prepared samples.

Plasmid DNA from 1 mL of detergent-treated or untreated cells was prepared by a plasmid mini-preparation alkaline lysis protocol. Plasmid DNA released into the supernatant from the detergent extraction was extracted using a Perfect-prep Gel Cleanup (Eppendorf; 955152051) column and solution, following the protocol of the manufacturer.

The entire amount from each sample was loaded onto a 1% agarose gel and imaged on a FujiFilm LAS-3000 Intelligent Darkbox using Image Reader LAS-3000 software and Multi Gauge v3.0 software.

FIG. 9 shows an ethidium-bromide stained 1% agarose gel with TAE buffer with samples of plasmid DNA from both cell lines.

Lane 1 of FIG. 9 is the total plasmid DNA in untreated cells. Lane 2 is the supernatant from the permeabilisation step and Lane 3 is the plasmid retained in the cell capsule following permeabilisation. It is observed that there is very little plasmid release into the supernatant with permeabilisation, despite the complete loss of soluble His6::GFP protein observed in FIG. 8. Therefore, plasmid DNA is almost completely retained by the cell wall and may be used in the method of the invention for the linkage of genotype to phenotype in screens for improved protein variants.

Confirming the microscopy data, the overnight incubation did not reveal any loss of plasmid DNA following overnight incubation at 37° C. of permeabilised cells suspended in TBS (lane 5).

Example 6

Peptidoglycan-Binding Scaffold

Another cellular structure that is retained following membrane permeabilisation is the cell wall, which is composed of a latticed polymer of peptidoglycan (PG).

To bind PG non-covalently, we cloned a 70 aa PG-binding domain from the *Pseudomonas* φKZ phage (KzPG) that was previously shown to be well expressed in *E. coli*, and to bind to the cell wall with high affinity (K=$3 \times 10^7$ M−1) (Briers et al., 2009). As a screen for affinity proteins would hopefully identify variants that have even higher affinities for their targets than the KzPG-binding domain for PG, we needed to increase the affinity of the scaffold-binding protein. To increase the affinity of the scaffold-binding moiety we linked both the ComE DNA binding domain (DBD) and the PG-binding domain in the same fusion protein. Therefore, the final dissociation constant of the fusion protein from both scaffolds (PG or DNA) should be the close to a multiple of each rate constant.

We therefore constructed an expression vector pAra3::His6::KzPG::SNAP::DBP (SEQ ID NO:2). Expression was induced as described in Example 1 and cells were prepared for fluorescence microscopy as described in Example 3. Expression and distribution of the fusion protein was monitored by SNAP labeling, as described in Example 3.

Fluorescence was observed at the periphery of the cell, in the area of the cell wall, and at a lower level in a diffuse area within the cell wall-bounded volume of the capsule.

Another embodiment of the invention would be to covalently attach the protein of interest to a cellular scaffold before permeabilisation. To achieve this, we used a protein fusion to LPP, an abundant *E. coli* protein that forms a trimeric coiled-coil in the periplasm. In its native form, one end is tethered to the outer membrane via lipidation and the other is covalently bound to the cell wall via a C-terminal lysine.

We constructed an expression construct that fused the OmpF periplasmic-targeting signal sequence to the SNAP expression reporter, followed by the 57 aa *E. coli* LPP sequence lacking the N-terminal signal sequence and cysteine required for outer membrane attachment. The expression vector, pAra3::OmpF::SNAP::LPP (SEQ ID NO:3) was induced with arabinose, as described by Example 1, and cells were prepared for fluorescence microscopy as described by Example 3. Expression and distribution of the fusion protein was monitored by SNAP labeling, as described in Example 3.

FIG. 10 shows the distribution of the LPP fusion protein was uneven across the surface of the cell wall, with areas of intense fluorescence and areas absent of any fluorescence. However, in almost all instances, the poles of the cells were labelled.

Example 7

Display of an αGFP Affinity Protein Using a Tetrameric Protein Scaffold

To demonstrate the method of the invention as applied to affinity proteins, a single-domain antibody generated from a Llama immunized against eGFP was cloned into the cellular scaffold vectors. It should be noted that, of the two sequences listed in the patent application for the αGFP antibody (WO 2007/068313), only the R35 variant was found to be functional (αGFP-R35; Protein Database ID 3K1K). Therefore, this sequence was used all experimental testing.

The αGFP-R35 gene was cloned as an N-terminal fusion to the pAra3::HALO::FLAG::RhnA tetrameric scaffold to create the pAra3::αGFP(R35)::HALO::FLAG::RhnA vector (SEQ ID NO:4).

A pAra3::His6::eGFP vector was also constructed to produce a His6::eGFP fusion protein as the target substrate of the antibody. The His6::eGFP protein was induced as described in Example 1. Soluble protein was released from cells using 0.5% 8TGP, was purified by IMAC using Ni-NTA agarose resin (Qiagen; 30230). His6::eGFP was eluted from the Ni-NTA resin in NTTW buffer+imidazole (500 mM NaCl, 50 mM Tris-HCl, pH 7.5, 0.1% Tween20+200 mM imidazole).

Expression of the antibody::tetrameric fusion protein and permeabilisation of host cells was conducted as described in Example 1 and 3.

For binding of αGFP to eGFP in permeabilised cellular capsules, the capsule pellet was suspended in 300 μL of eGFP and allowed to equilibrate for 20 minutes at 25° C., at which point the capsules were pelleted by centrifugation, washed once in 300 μL TBS, and then resuspended in TBS. Florescence microscopy on αGFP/eGFP capsules was conducted as described in Example 3.

FIG. 11 shows that the permeabilised capsules expressing αGFP::HALO::RhnA fusion protein bound eGFP throughout the cell, although there appeared to be foci of more intense staining that may correlate to the foci observed in FIG. 5 with HALO ligand labeling.

Therefore, the Llama αGFP antibody is functionally expressed in the cytoplasm and, furthermore, is retained within the capsule following detergent permeabilisation.

The αHis antibody labeling described in Example 3 and observed in FIG. 5 already demonstrated that a larger protein of ~150 kD is capable of diffusing through the permeabilised cell wall into the interior of the capsule. However, native antibodies are irregular-shaped proteins with 3 approximately equal-sized domains separated by a flexible hinge region. Thus, the effective radius that these proteins may present may be of a much smaller globular protein. However, GFP, which has a β-barrel structure and a molecular size of ~27 kD, is a symmetrical protein with a radius proportional to its size, was able to pass through the cell walls of the permeabilised capsule to be bound by the internal αGFP antibody.

Thus, the method of the invention may be used to express affinity proteins in the *E. coli* cytoplasm for the use in display of affinity libraries for binding symmetrical targets of at least 30 kD.

Example 8

Display of an αGFP Affinity Protein Using a PG- and DNA-Binding Protein Scaffold The method of the invention was further demonstrated using the αGFP camelid antibody fused to PG- and DNA-binding domains.

Expression of the antibody::KzPG::SNAP::DBP fusion protein, permeabilisation of host cells and labeling with His6::eGFP was conducted as described for Example 6.

Both wet and dry mounts were used to image the binding of eGFP by the αGFP fusion protein. FIG. 12 shows that there were significant differences with the GFP fluorescence between the two different imaging methods. Dry mounted (DABCO/glycerol) cells had mostly internal fluorescence, with a merge between the brightfield and eGFP labeling showing that the region around the cell wall was no more intense than the internal volume (FIG. 12B). Cells mounted directly in TBS, however, had a distinctive pattern of an outer border of strong fluorescence that appears to be the cell wall-bound eGFP with a weaker internal signal (FIG. 12A). Without being bound by theory, we speculate that the DABCO/glycerol solvent environment, being viscous and non-aqueous, prevented the interaction between the KzPG domain with the peptidoglycan cell wall, but did not prevent the binding of αGFP to eGFP, or the DBP to DNA.

However, as the screening procedures for affinity proteins or enzymes will almost always be conducted in aqueous environments, the distribution of the affinity fusion protein will approximate the observed cell wall-bound wet mount of FIG. 12A.

Example 9

Display of an αGFP Affinity Protein Through Covalent Attachment to the Cell Wall The method of the invention was further demonstrated by covalently linking the αGFP antibody to the cell wall.

The αGFP antibody was cloned as an arabinose-inducible fusion downstream from the OmpF signal sequence and upstream from the SNAP and LPP sequences.

Upon induction of expression by arabinose, the OmpF signal sequence will direct the nascent protein through the inner cell membrane into the periplasm and will be cleaved off as it passes through the membrane pore.

In the periplasm, the LPP domain is expected to form a trimeric coiled-coil with two other partners, either wild-type LPP or with other αGFP fusion proteins. The C-terminal residue of the LPP domain is a lysine that is covalently linked to the E. coli cell wall through the c amine group, most probably by the YbiS L,D-transpeptidase (Magnet et al., 2007).

Expression of the OmpF::αGFP::SNAP::LPP fusion protein, cellular permeabilisation and eGFP labeling was performed as described for Example 8.

FIG. 13 shows that eGFP was bound unevenly, but intensely, around the cell wall (FIG. 13B). eGFP was not bound by cells expressing the OmpF::SNAP::LPP fusion without the αGFP domain (FIG. 13A).

Covalent attachment of the OmpF::SNAP::LPP fusion to the cell wall was demonstrated by first labeling permeabilised cells expressing the fusion protein with a SNAP ligand before heating a sample of the labelled cell capsules to 95° C. for 5 minutes. FIG. 14 demonstrates that the fluorescence from the SNAP ligand labeling the cell wall was unchanged between the heat-treated sample, and a control that was not heated. Gel Red staining also demonstrated that the genomic DNA was still retained in the cell, even in the heat-treated sample.

Example 10

Outer Membrane Permeabilisation Experiments

In a further embodiment of the invention, the outer membrane may be selectively permeabilised for ligand targets, such as for example enzyme substrates or polypeptides, while retaining the polypeptide that is being screened either within, or attached to, the cell wall.

To identify conditions that would selectively permeabilise the outer membrane, a range of detergents and buffers were screened. Both large (eGFP) and small (Gel Red) ligands were used to determine if the permeabilisation of the outer/inner membranes generated either large or small membrane pores.

E. coli strains expressing arabinose-inducible OmpF:: αGFP::SNAP::LPP (cell wall attached) or αGFP::HALO:: FLAG::RhnA (cytoplasmic) were grown and induced as described for Example 1.

1 mL of induced culture was washed once in 50 mM Tris (pH 8) before being suspended in permeabilisation buffer variants containing 0.2-0.4% detergent in either 25 mM Tris+1 mM EDTA (pH 8) or 25 mM Tris+2 mM $Ca^{2+}$ (pH 8) and incubated at 25° C. for 10 minutes.

Permeabilised cells were washed once in appropriate buffer and then stained with Gel Red (1× in water) and washed with TBS. They were then incubated with purified His6::eGFP for 1 hour at 25° C. before being pelleted by centrifugation and resuspended in TBS and viewed by fluorescence microscopy as a wet mount.

FIGS. 15 and 16 demonstrate that 0.2% Apo8 (A) or Tween20 (B) in either a Tris/$Ca^{2+}$ or Tris/EDTA buffer selectively permeabilised the outer membrane allowing the permeation of a large ligand (eGFP) through the outer membrane but not through the inner membrane. The smaller, membrane impermeable, DNA-binding ligand Gel Red was partially permeable to the cytoplasm in most samples, indicating that some degree of poration of the inner membrane was occurring in some cells. However, the degree of Gel Red binding was much reduced compared to samples that had been treated with the detergents 0.5% 8TGP or Agent86 where both the outer and inner membranes were fully permeable to eGFP.

Example 11

Fluorescence Sorting and Analysis of Encapsulated Display

As a cellular display platform, the method of the invention is ideally suited for fluorescence-activated cell sorting (FACS) to identify ligand-binding clones. To test the stability of permeabilised E. coli cells for sorting by FACS, three populations were induced for expression: i) eGFP; ii) αGFP::KzPG::SNAP::DBP; and iii) His6::SNAP::BetB.

The eGFP-expressing cells were not permeabilised, and were a positive control for fluorescence in intact E. coli cells. The αGFP::KzPG::SNAP::DBP expressing cells were permeabilised according to the method of the invention, and were labeled with the SNAP BG-488 ligand (green). The His6::SNAP::BetB expressing cells were permeabilised according to the method of the invention, and were labeled with the SNAP BG-547 ligand (red).

Cells were suspended in PBS and mixed in approximately equal numbers for sorting of mixed populations or sorted separately for signal calibration. Cell sorting was performed on a Becton Dickson Influx FACS. Data analysis was performed on FlowJo software. Parameters for E. coli sorting were determined by the operator.

FIG. 17 demonstrates that the three populations were identifiable by fluorescence. Reanalysis of the sorted populations showed that the sorting provided relatively pure populations of each. The signals present in the low-fluorescence region of the graph were later shown to be inherent noise in the signal and later removed by the operator by instrument corrections.

Example 12

Spacer Region Selection for Solid Support Binding

Cells expressing the αGFP::KzPG::SNAP::DBP fusion protein were permeabilised using 8TGP media, and cells bound to HisPur Co$^{2+}$ sepharose beads (Thermo Scientific) via an intermediate, His6-tagged eGFP. Either cells or beads were first incubated with an excess of His6-eGFP before being washed in TBS and then incubated together for 30 minutes at 25° C. Unbound cells were then washed away from the beads before the extent of bead binding was assessed by fluorescence microscopy.

Initially no binding of the αGFP::KzPG::SNAP::DBP fusion protein to sepharose beads was detected. It was theorized that the αGFP binding domain may be in too close proximity to the cell wall to reach the cobalt-complexed eGFP on the sepharose resin. Accordingly, a 12-residue peptide spacer domain with randomized codons was cloned between the αGFP binding domain and the kzPG peptidoglycan binding domain (GGT ACC gcy gcy gkk wtb gck wtb gkk gkk gck gkk gcy gcy GGT CTG (SEQ ID NO:5))

A small library (~2,000 members) of the spacer variants was expressed and then bound to Co2+ sepharose, as described above. A proportion of the library was observed to bind to the beads. These clones were then PCR amplified, re-cloned and a dozen clones were tested individually for binding and sequenced. A variety of peptide spacers were found to be both resistant to proteolytic cleavage (maintaining high levels of αGFP in the fusion protein) as well as enabling binding of the detergent-treated cells to the sepharose beads as demonstrated by FIG. 18. Spacer sequences that were found to be functional for support binding are listed in Table 1.

TABLE 1

Random linker (RL) spacers for solid support binding

| Linker | Amino acid sequence |
|---|---|
| RL1 | GSNSNNQSKPSS (SEQ ID NO: 6) |
| RL2 | GGPRNPQRHTGS (SEQ ID NO: 7) |
| RL6 | SGTRHHNSHNSS (SEQ ID NO: 8) |
| RL9 | SSNRTHKSNNSS (SEQ ID NO: 9) |
| RL10 | SGHRTTERKHSS (SEQ ID NO: 10) |
| RL13 | GGHRHTQRHNGG (SEQ ID NO: 11) |
| RL14 | GGPRTPQSQPSG (SEQ ID NO: 12) |

One spacer sequence, RL6, was chosen for further binding studies. Other factors contributing to strong binding to solid support matrixes were examined. The length of time for incubation of the cells with the matrix and the salt (NaCl) concentration of the binding solution were both found to have positive effects on binding. Incubation lengths of 30 minutes and a range of NaCl concentrations from ~200 mM to 500 mM were found to be effective although 300 mM was considered optimal. Binding was effective in a range of buffers, including Tris, phosphate and MOPS buffered solutions with 300 mM salt.

Conditions of binding for cells expressing the αGFP::RL6::KzPG::SNAP::DBP fusion protein to streptavadin magnetic nanoparticles (MagneSphere; Roche diagnostics) via biotinylated eGFP were also confirmed as being within the ranges identified for sepharose bead binding and demonstrated by FIG. 19.

In addition to the 12-residue spacers, protein domains were also considered for use as spacer domains. The small, stable and highly-expressed 27th immunoglobulin domain from the human titin gene (I27) was cloned upstream from the RL6 spacer. This domain was also found to enable high and stable expression of the N-terminal αGFP domain as well as excellent solid matrix binding (FIG. 19).

Example 13

Construction of a Mouse scFv Library for Encapsulated Display

The final domain structure for the intracellular display of a single-chain antibody (scFv) library was: scFv::I27::RL6::KzPG::SNAP::DBP. The protein and DNA sequences of the fusion protein without the scFv domain are provided as SEQ ID NO:13 and SEQ ID NO:14. This protein fusion has the scFv at the N-terminus, followed by the two spacer domains, I27 and RL6, then the peptidoglycan binding domain, KzPG, the SNAP reporter domain and, finally, the DNA binding domain (DBP).

Random-primed cDNA was produced from mouse spleen total RNA using the Superscript III (Invitrogen) enzyme. From this cDNA, the scFv light ($V_L$) and heavy ($V_H$) chain variable domains were amplified using Vent DNA polymerase (New England Biolabs) and degenerate oligonucleotide primers for the mouse antibody family sequences, as described by Schaefer et al. (2010). The oligonucleotide primers used for library cloning differed from those described by Schaefer et al. in that they had appropriate ends for cloning via Bsm BI into our library scaffold vector (SEQ ID NO:15). The VL and VH domains were joined using overlapping extension PCR. The final scFv band had been subjected to a total of 60 PCR amplification cycles (30 first round, 30 second round).

For library cloning, 900 ng of the display construct was cut with BsmBI, precipitated using Sureclean (Bioline) according to the manufacturer's instructions, and ligated using T4 DNA ligase to 400 ng of similarly-treated scFv product. The ligase was inactivated by incubation at 65° C. for 10 minutes and the ligation electroporated into the E. coli Argentum strain (Alchemy Biosciences). The electroporated cells were recovered in SOC media and incubated for 1 hour at 37° C. before pooling and then spread across 20×150 mm LB agar plates with 75 ug/mL ampicillin. The plates were incubated overnight at 30° C. The library size was estimated at $4 \times 10^5$ independent clones. 20 out of 20 colonies were found to contain an insert of the expected size.

Example 14

Screening of an Encapsulated Display Mouse scFv Library

Single chain antibodies isolated from phage display libraries are often difficult to express in E. coli, with either low levels of expression in the periplasm, or are completely insoluble in the cytoplasm due to the lack of disulphide bond formation between the B-sheets of the Ig fold. To determine whether encapsulated display could be used to select for a mouse scFv scaffold that would be soluble in the *E. coli* cytoplasm, it was necessary to determine whether scFv solubility was correlated with the behavior of the fusion protein.

It was predicted that a useful soluble scFv would have low levels of aggregation and at least a moderate level of expression. This could be judged visually as a clone that allowed binding of the KzPG domain in a permeabilised cell to the cell wall (and not therefore, localized to an inclusion body within the cell) and that showed at least moderate expression of the SNAP reporter domain.

To screen for these parameters, single colonies were picked and induced for fusion protein expression using arabinose as described previously for Example 1. Following permeabilisation they were labelled with SNAP ligand and viewed using fluorescence microscopy. We characterised the library clones into four categories based on their expression and cellular distribution of SNAP reporter, examples of which can be seen in FIG. 20.
1) no expression of SNAP
2) moderate/high expression of SNAP in aggregated inclusion bodies (FIG. 20, left panel)
3) weak expression of SNAP with cell wall localization (FIG. 20, mid panel)
4) high expression of SNAP with cell wall localization (FIG. 20, right panel)

Only clones with both high expression and solubility were analysed further. However, as the weak expression of the SNAP reporter could be due to inefficient expression of a protein not optimized for *E. coli* expression it is expected that a proportion of these clones would prove to be excellent for soluble cytoplasmic library display if their codon usage were optimised.

Clones with high expression of the SNAP reporter and an even distribution around the cell wall of permeabilised cells were sequenced to confirm the presence of a scFv insert that was in the correct translation frame with the remainder of the fusion protein. In all 21 clones analysed, the scFv insert was found to be full length, with the correct length of the glycine/serine linker region, and in the correct reading frame for translation of the entire fusion protein. This suggested that the method of screening of the invention was correctly identifying mouse scFv genes that were expressed in a soluble form in the cytoplasm of *E. coli* cells. To confirm that the scFv proteins isolated from the library were soluble in the *E. coli* cytoplasm they were shuttled from the library construct to an arabinose-inducible expression vector with a C-terminal FLAG epitope with an intervening spacer region of either I27-RL6 or RL6.

Following induction of protein expression by arabinose, the soluble scFv::I27::RL6::FLAG or scFv::RL6::FLAG fusion proteins were extracted with 0.5% 8TGP. The insoluble cellular material was pelleted and resuspended in SDS-PAGE loading buffer with β-mercaptoethanol by sonication of the sample and heated to 95° C. for 5 minutes. Equal volumes of each fraction were loaded onto 10% SDS-PAGE gels and electrophoresed. Separated proteins were transferred to nitrocellulose membranes, which were then blocked with 5% skim milk powder. Recombinant protein expression was probed using a 1:1000 dilution of a sheep αFLAG antibody (Sigma) followed by an anti-mouse-HRP conjugated secondary antibody. Detection was using chemiluminesence.

FIG. 21 demonstrates that the method of the invention is capable of identifying scFv genes that are expressed in a mostly soluble form within the bacterial cytoplasm. The Western blot of the expression profiles is matched in each sample with the fluorescence microscopy detected by SNAP ligand for the scFv::I27::RL6::FLAG construct.

Example 15

P2 Lysogen Generation in Argentum Strain *E. Coli*

A P2 lysogen of Argentum (K12; ΔmcrA Δ(mrr-hsdRMS-mcrBC) ΔendA lacZΔM15) was created by outgrowth from a single plaque of P2 on a lawn of Argentum cells. Phage infection was conducted as described by Kahn et al. (1991).

Example 16

P2 ΔYK Knockout a. Generation by Homologous Recombination

P2 bacteriophage has genes for a putative holin and lysin system, similar to the lysis system characterized for many lytic and lysogenic bacteriophages. The holin provides access through the inner membrane to the periplasmic space for the lysin enzyme to degrade the murein cell wall.

The P2 K gene (SEQ ID NO:17) and Y gene (SEQ ID NO:18) encode putative lysozyme and holin, respectively. These genes were deleted using homologous recombination similarly as described by Hamilton et al. (1989). Regions of flanking homology were chosen from the P2 genome (Genbank sequence NC_001895.1) and cloned between a FRT-flanked kanamycin selection cassette The region of replacement of the P2 genome was 6,721 to 7,487 bp.

Following replacement of the targeted YK genes, the kanamycin cassette was removed by FLP recombinase expressed from the pCP20 plasmid, as described by Cherepanov and Wackernagel (1995). The resultant strain had a deletion of the YK genes with a short 20-mer peptide remaining as the only ORF.

The K12 P2 ΔYK strain was functionally tested by infection with P4 bacteriophage. Argentum (P2) and Argentum (P2 ΔYK) cultures were infected with $10^3$ pfu of P4 bacteriophage and poured into top agar plates. Plaques were observed to form on lawns of Argentum (P2) but not Argentum (P2 ΔYK).

b. Testing Using P4 Vir1 and Ready-Lyse

To test the functionality of the P2 bacteriophage YK deletion (P2 ΔYK) to replicate and package an infecting P4 bacteriophage, the P2 ΔYK strain was infected with the P4 mutant, P4 vir1, that has a mutation that increases transcription of the P4 control region and has a clear-plaque phenotype.

P2 ΔYK cells were grown to early-log phase and supplemented with 1 mM $CaCl_2$. 1 μL of a lysate supernatant containing $10^9$ pfu/mL of P4 vir1 bacteriophage was added to 1 mL of P2 ΔYK culture and incubated for 80 minutes at 37° C. The suspension was centrifuged to pellet the cells, the supernatant discarded and the pellet washed three times in LB media containing 0.08 mM EGTA and 2.5 mM $MgCl_2$ to remove unbound P4 vir1. The cells were resuspended in 1 mL LB media and then divided into three samples. One sample was retained without further treatment (Sample 1; unpermeabilised). Samples 2 and 3 were treated further by pelleting and resuspension in LB supplemented with 0.5% of the detergent 8TGP to permeabilise both inner and outer membranes. The cells were then pelleted and washed twice in unsupplemented LB media. The permeabilised, washed cell pellets were resuspended in LB media. Sample 2 (permeabilised) was retained without further treatment. Sample 3 (permeabilised; lysozyme) was further treated with 0.5 μL Ready-Lyse (Epicentre, USA), which is a recombinant lysozyme. The rapid decrease in turbidity indicated that the peptidoglycan cell wall was degraded by Ready-Lyse and that any packaged P4 vir1 particles would now be released into the lysate.

10 μL of each of Samples 1 and 2 and 0.1 μL of Sample 3 (a dilution of the raw lysate) were then added to 200 μL of fresh K12 (P2) cells supplemented with 1 mM $CaCl_2$. The cells were incubated at 37° C. for 20 minutes, then 7 mL of top agar (LB media, % agar) was added and poured over pre-warmed LB plates. The plates were incubated overnight at 37° C. and the presence of P4 vir1 plaques in the K12 lawn determined the next morning.

Sample 1, which represented P4-infected cells that had not been permeabilised, produced 83 plaques in the top-agar plate. Sample 2, which represented P4-infected cells that had been permeabilised by detergent, produced 34 plaques. Sample 3, which represented P4-infected cells that had been both permeabilised by detergent and then the cell wall degraded by lysozyme, produced 168 plaques.

Adjusting for sample dilution, the permeabilised, lysozyme-treated P2 ΔYK cells (Sample 3) had 200-fold more P4 vir1 bacteriophage than Sample 1 and 500-fold more P4 vir 1 bacteriophage than Sample 2.

The presence of replication-competent P4 vir1 bacteriophage in infected K12 P2 ΔYK cells demonstrates that the deletion of the YK lysis genes did not prevent replication of the P4 vir 1 genome, or assembly of functional bacteriophage particles. Deletion of the YK lysis genes did, however, prevent release of the assembled bacteriophage particles from infected cells. Permeabilisation of the inner and outer cellular membranes, achieved by detergent treatment, did not result in release of bacteriophage particles into solution. However, treatment of the permeabilised cells with a lysozyme released infectious bacteriophage into solution.

Example 17

P2 ΔYK/P4 Co-Lysogen with Inducible Activator a. Generation of a P2/P4 Co-Lysogen in C1a Cells Historically, the strain used for experimenting with the P2 bacteriophage and its satellite, P4, is the C strain of *E. coli* (Wiman et al., 1970). Using a derivative of C strain, C1a (Sasaki and Bertani, 1965), we established a P2 lysogen through subcloning of lysogenised cells from P2 plaques, as described above. Similarly, we established P4 co-lysogens of the C1a P2 strain.

A P2/P4 colysogen strain has both prophages under transcriptional repression. To use this strain to inducibly package a cosmid library plasmid both phages need to be activated. For the other well-characterised temperate phage, lambda, release of repression occurs with inactivation of the repressor protein, cI, either through RecA/LexA-mediated cleavage or using a thermolabile mutant repressor, cI857. However, P2 is known as an uninducible phage in that it is unresponsive to depression by inactivation of its repressor, presumably because it is unable to coordinate excision from the genome with replication and structural gene transcription (Bertani, 1968). However, the infecting P4 satellite phage has mechanisms of activating repressed P2 prophage upon entry. The P4 e (epsilon) protein acts as an anti-repressor through binding to the P2 repressor protein. In addition, the P4 δ (delta) protein is a potent activator of P2 structural operons, being a fused tandem duplication of the P2 ogr transcription activator. However, a P4 prophage has a complex and stringent control of both its own and P2's activation.

The P4 prophage uses the interplay between a transcriptional repressor, the V is protein, on its own promoter and the downstream Eta and cI genes that rely on transcription and translation coupling to produce an inhibitory complex based on the cI RNA. Ultimately this complex acts to block expression of the P4ε protein, which is a binding antagonist of the P2 repressor protein.

Derepression of P4 and P2 prophages requires inhibition of the P2 repressor by the P4 e protein. Activated P2 in turn produces the Cox and Ogr transcription activators that act in trans to promote transcription of the P4 δ gene, which further activates P4 via the V is promoter and also acts in trans on P2 structural gene operons.

In such a complex system, with many elements interacting to reinforce their combined effects a cell containing both repressed prophages, P2 and P4, must tightly control expression of all the activator genes to prevent a positive feedback effect occurring. Potential activators of the prophages include the P2 cox, P2 ogr and P4 δ transcription activators, as well as the P4ε anti-repressor.

The three transcription activators were cloned under the tight transcriptional control provided by the temperature-sensitive allele of the λ phage repressor, cI857. The low-copy pACYC184 plasmid origin of replication compatible with the pUC origin enables maintenance of the inducible activator alongside a pUC-based library plasmid.

The C1a P2/P4 co-lysogen was transformed with the inducible expression constructs and grown at 30° C. The cultures were grown to early log phase before induction through temperature shift to 42° C. for 20 minutes, before growth at 37° C. until lysis occurred.

All three activators were capable of inducing lysis in a colysogen, although the P4 δ gene demonstrated the earliest lysis, followed by ogr, and then cox. The polynucleotide sequence of the temperature-inducible P4 δ is provided in SEQ ID NO:19.

Production of infectious bacteriophage P4 particles was confirmed by titration of the lysate against cultures of C1a P2 lysogen. The P4 titre was determined to be >$10^9$ pfu/mL.

Example 18

P2 ΔYK with Cosmid Transmission

To utilise the P2/P4 system for gene library screening and transmission, a vector was constructed that contained the P4 cos region. A 389 bp region from P4 starting from the psu gene, spanning over the cos cleavage site, and to the gop gene (11461 bp to 225 bp of the P4 genome; NCBI accession number NC_001609) was amplified by PCR and cloned into a high-copy pUC-origin plasmid vector. The identity of the P4 cos region was verified by sequencing. The vector also contained the araC gene and arabinose-inducible promoter controlling expression of a library intracellular display screening system as described by patent application PCT/AU2010/001702.

As with all cosmid vectors, whether for P2, P4 or λ bacteriophages, there is a minimum size for the packaging into the capsid head for producing a viable transmissive unit. For P4, this has been determined to be approximately 9.2 kb (Kim and Song, 2006). To achieve this minimum size for packaging in a P4 capsid head the total size of the cosmid vector was increased to 10.7 kb, closer to the wild-type P4 genome size of 11.6 kb, by cloning in a 4.3 kb 'stuffer' fragment of E. coli genomic DNA.

To demonstrate co-packaging of the cosmid vector resident in a C1a P2 ΔYK/P4 co-lysogen the strain was transformed with the pUC-backbone, ampicillin-resistant cosmid vector as well as the pACYC184-backbone, chloramphenicol-resistant vector with the temperature-inducible P4 δ gene.

The strain with both colysogens and both plasmids was grown at 30° C. to early-log phase before the P4 δ protein was induced by temperature shift to 42° C. for 20 minutes, followed by growth at 37° C. for 1 hour. As a control, a strain containing a library plasmid without the P4 cos region and the stuffer fragment was also induced for P4 capsid packaging.

To release the packaged cosmids and P4 bacteriophage, the induced cells were pelleted and resuspended in permeabilisation media (LB media+0.5% 8TGP) for 10 minutes at room temperature (~25° C.). Following permeabilisation, they were pelleted and resuspended in LB and 0.5 µL of Ready-Lyse lysozyme added to digest the cell wall. Lysis was confirmed by the drop in turbidity. It was also confirmed that chloroform was also effective in permeabilising the cell for the action of Ready-Lyse on the cell wall. Packaged cosmids and P4 bacteriophage were titred by infection of C1a and C1a P2 lysogens, respectively.

It was confirmed that the library cosmid was packaged at approximately equal levels as the resident P4 prophage in induced P2 ΔYK cells as approximately equal numbers of antibiotic resistant colonies from the cosmid recovery were obtained compared to P4 plaques. No colonies were obtained from infection with a lysate prepared from the strain carrying the library plasmid that lacked a P4 cos region and stuffer fragment.

It was also noted that, unlike the poor stability of P4 bacteriophage or packaged cosmids in raw lysates from lysed C1a P2 cells (stored at 4° C. in LB media with Mg/EGTA), presumably due to the action of cellular proteases also in the lysate, the P4 bacteriophage and packaged cosmids released from P2 ΔYK cells that were first permeabilised and washed, before lysed by the action of exogenously added lysozyme (Ready-Lyse) were stable at room temperature with only a minor drop in titre over 2 days. This is presumably due to the release of the aforementioned proteases from the permeabilised cells which are then washed away from the infectious particles that are retained by the cell wall during the pelleting and media change steps. Thus, a high-titre of cosmid particles could be easily produced by temperature induction, permeabilisation and media change, and kept at a stable titre without requiring long ultra-centrifugation purification steps as per standard bacteriophage protocols.

Example 19

Permeabilisation of E. coli Using Organic Solvents

In addition to the permeabilisation of Gram-negative cells using detergents, another chemical agent for disrupting membrane integrity might be the lipophilic organic solvents. Organic solvents have been used substantially in the prior art in cell permeabilisation and fixation for immunolabelling for microscopy (Harlow and Lane, Antibodies: A Laboratory Manual, Cold Spring Harbour Laboratory, 1988). In the method of the invention, the cell membrane is permeabilised for the entry of large immunoglobulin complexes which bind to intracellular targets.

In particular, the organic solvent chloroform has also been used to selectively kill bacterial cells in a cell/bacteriophage suspension, presumably through permeabilisation of the cellular membranes (Sambrook et al. 2001). Chloroform has also been used in lytic bacteriophage genetics to enable rescue of holin mutants that were unable to permeabilise the inner membrane to release lysozyme from the cell cytoplasm for bacteriophage release (Ziermann et al., 1994). Similarly, it was used to rescue lysozyme mutants that were unable to hydrolyse the peptidoglycan cell wall by permeabilising the outer membrane to enable active exogenous lysozyme entry to the periplasm (Ziermann et al., 1994). Therefore, chloroform was demonstrably able to allow at least small (~15 kD) lysozymes passage through both the inner and outer membranes of the Gram-negative E. coli cell.

To test organic solvents for permeabilisation of the cellular membranes for use in intracellular display described by the method of the invention, E. coli cells expressing the αGFP::RL6::KzPG::SNAP::DBP fusion protein (expression induced as described for Example 8) were suspended in aqueous mixtures of organic solvents. Membrane permeabilisation was indicated by the binding of a small molecular weight DNA-binding fluorescent ligand, Gel Red, and of a 30 kD protein, eGFP.

Although some organic solvents remain miscible in water (e.g. the shorter-chain alcohols) others are largely immiscible and the mixture partitions into aqueous and non-aqueous phases (for example, chloroform and butanol). The phase portioning represents the saturation of the low solubility of the organic solvent in the aqueous phase.

Cells expressing the αGFP::RL6::KzPG::SNAP::DBP fusion protein were collected by centrifugation and permeabilised with one of the following solvent compositions for 10 min at 25° C. LB growth media was used for the aqueous component of the mixture. Tris-buffered controls were also performed.

10% ethanol; 20% ethanol; 30% ethanol
10% methanol; 20% methanol; 30% methanol
10% isopropanol; 20% isopropanol; 30% isopropanol
10% DMSO; 20% DMSO; 30% DMSO
10% acetone; 20% acetone; 30% acetone
Butanol (1:5)
Chloroform (1:5)
50 mM Tris/LB (pH 7.0); 1 M Tris/LB (pH 7.0)

Following solvent treatment, cells were pelleted by centrifugation, washed once with LB media by suspension, pelleted by centrifugation and then suspended in LB media containing either the small-molecular weight DNA-binding fluorophore, Gel Red (1:10,000 dilution in water), or eGFP. Following a 20 minute incubation at 25° C. in labeling media, cells were pelleted by centrifugation, washed in LB by resuspension, then viewed by fluorescence microscopy. FIG. 22 demonstrates that, of the organic solvents tested, chloroform and butanol permeabilised the E. coli cellular membranes to allow a small molecular weight ligand entry into the cytoplasm (A), but only chloroform permitted entry of a large molecular weight protein (~30 kD).

Example 20

Capsid Display Using the P2 gpL Decoration Protein

The P2 bacteriophage gpL protein was detected as a structural component of mature virions by mass spectrometry (Chang et al., 2008) and is presumed to be the functional equivalent of the gpD capsid protein of lambda bacteriophage, even though the two proteins do not demonstrate any regions of significant homology by a pairwise BLAST alignment (NCBI). The lambda gpD protein is 110 residues in length, whereas the P2 gpL protein is 169 residues in length.

To test whether the P2 gpL protein would function for capsid display the αGFP:I27 sequence was fused to the N- and C-terminal ends of P2 gpL to create the fusion proteins listed as SEQ ID NO:20 and SEQ ID NO:21. The fusion protein also included a FLAG epitope tag interspacing the gpL and αGFP:I27 domains. Expression of the fusion protein was made arabinose-inducible by cloning the gene sequence downstream from the araBAD promoter, with an upstream araC transcriptional regulator. The DNA sequence of the αGFP:I27:gpL expression vector is listed as SEQ ID NO:22.

The plasmid encoding the αGFP:I27:gpL fusion protein was transformed into an E. coli K12 host containing a Hy5 prophage. The Hy5 phage is a hybrid of the related phages P2 and 186 containing the P2 structural genes under 186 transcriptional control (Bradley et al., 1975; Younghusband et al., 1975). Furthermore, the Hy5 (186) a repressor is temperature sensitive, allowing temperature induction of phage growth.

Expression of the αGFP:I27:gpL fusion protein by arabinose and analysis by SDS-PAGE produced an upper band of approximately 55 kD, which was higher than the expected size of 44 kD that was in both the soluble and insoluble fractions, and a lower band that was solely in the soluble fraction (FIG. 23).

To demonstrate that the αGFP:I27:gpL fusion protein was bound to the phage capsid and was functional for binding by phage display, the prophage strain with the expression construct was heated to 45° C. for 15 minutes to trigger Hy5 replication. Following heat-shock the samples were shifted downwards in temperature for growth at 32° C. Fusion protein expression was induced 30 minutes after the temperature downshift with the addition of arabinose to a concentration of 0.2%. Cultures were incubated for a total time of 70 minutes at 32° C. for maximal phage release.

For capture of Hy5 phage displaying the αGFP:I27:gpL fusion protein streptavidin-coated Dynal beads (M-270, cat. no. 653-05; Life Technologies) were first labelled with biotinylated His6-GFP and thoroughly washed with TBS. Labelling of the Dynal beads with eGFP was confirmed by fluorescence microscopy.

Table 2 lists the results of the gpL fusion protein expression on Hy5 phage capture by Dynal beads. These data demonstrate that fusion of the αGFP antibody to the P2 gpL capsid protein results in 82-fold enrichment by the Dynal beads over phage that are packaged using the wild-type gpL protein. Furthermore, even the uninduced sample with an undetectable level of fusion protein expression (FIG. 23, sample 1) was still affinity-purified at a significant level above the control, suggesting that even a very low level of display was resulting in phage capture.

TABLE 2

Enrichment of Hy5 phage displaying the gpL capsid fusion protein over Hy5 control.

| | Stock titre (PFU/mL) | Panned output (PFU) | Enrichment (fold over Hy5) |
|---|---|---|---|
| Hy5 | $3.5 \times 10^9$ | 93 | (reference sample) |
| Hy5 + αGFP:I27:gpL (not induced) | $1.2 \times 10^9$ | 202 | 6.5× |

TABLE 2-continued

Enrichment of Hy5 phage displaying the gpL capsid fusion protein over Hy5 control.

| | Stock titre (PFU/mL) | Panned output (PFU) | Enrichment (fold over Hy5) |
|---|---|---|---|
| Hy5 + αGFP:I27:gpL (induced) | $1.1 \times 10^9$ | 2,550 | 82× |

Example 21

Deletion of the Lambda Phage SR Lysis Genes

The lambda phage lysis genes are located on the right arm of the genome in a cluster containing the S'/S (holin (SEQ ID NO:23)/anti-holin), R (endolysin (SEQ ID NO:24)), Rz/Rz1 (required for lysis in certain media) genes. The lysis cluster is within a larger transcriptional unit transcribed from the pR promoter that is responsible for transcription of all lambda structural and lytic genes. The pR' mRNA is a single transcript that therefore covers approximately half of the lambda genome. To inactivate the lysis genes it was decided to delete the genes using homologous recombination. To enable facile selection for the lambda mutants the lysis genes were replaced with a kanamycin resistance gene (KanR). However, to ensure that neither promoter or transcription terminator sequences were inserted that would result in prophage structural gene expression that might be detrimental to cellular viability, the neighbouring non-essential bor gene was also deleted. The bor gene, which confers serum resistance to the host E. coli cell, is constitutively expressed in the prophage in the opposite direction to the pR' under its own promoter (Barondess and Beckwith, 1995). Using synthetic gBlocks fragments (IDT) we designed a truncation of the lysis cluster with a fusion of the start codon of the KanR gene to the start codon of the bor gene. The only sequence remaining of the lambda lysis cluster from this deletion was a truncated peptide of sequence MKMPEKQLEGTQKYINEQCR (SEQ ID NO:25). The DNA sequence of the lysis deletion construct with synthetic arms and KanR cassette is listed as SEQ ID NO:27.

The synthetic homology arms and the KanR cassette were cloned into the pUC-based PCR cloning vector, pAcquire (Alchemy Biosciences, Melbourne, Australia), and were verified by sequencing.

To effect the deletion of the lambda lysis cluster, the construct was transformed into a lambda cI857sam7 lysogen of E. coli strain ED8739 (F−, metB, hsdS, supE, supF) and phage lysis was induced by temperature induction (42° C., 10 mins) followed by growth at 37° C. for 1 hour. 1 mL of supernatant containing phage was clarified by centrifugation and 1 drop of chloroform added. A culture of ED8739 with supplemented magnesium (10 mM) and maltose (0.1%) was then infected with dilutions of the phage lysate and lysogens were recovered by outgrowth at 30° C. for 2 hours before plating on LB+kanamycin (15 μg/mL) agar plates which were grown for 16 hours at 30° C.

As the targeting plasmid was small enough for lambda::plasmid recombinants to be packaged as viable phage the kanamycin-resistant prophage colonies were therefore screened for the loss of the ampicillin resistance gene (i.e. $Kan^R/Amp^S$), which would indicate a homologous recombination event between both homology arms of the targeting construct, excising the lysis cluster and replacing it with the kanamycin cassette as desired. Kan$^R$/Amp$^S$ prophage were identified and to confirm that the deletion was effected without undesired mutations, the region was amplified by PCR and sequenced. All clones were found to be correct as designed.

Example 22

Packaging of the Lambda ΔSR Genome

To demonstrate that deletion of the lysis cluster still produced the same number of viable packaged phage per cell (i.e. that the modified pR' transcript didn't effect production of the phage structural proteins), the lambda cI857sam7ΔSR prophage was grown alongside the lambda cI857sam7 prophage at 30° C. to an identical cellular density and phage production was induced by temperature induction (42° C., 10 mins) followed by growth at 37° C. for 1 hour. As expected the lambda cI857sam7 culture lysed to completion whereas the lambda cI857sam7ΔSR failed to lyse. The lambda cI857sam7ΔSR culture was collected by centrifugation and resuspended in LB+0.5% 8TGP and incubated at 25° C. for 10 minutes. The permeabilised cells were then collected by centrifugation, washed once with LB+10 mM MgSO4 and resuspended in the original 1 mL volume of LB+10 mM MgSO4 and lysed using 0.5 μL of ReadyLyse (Epicentre). A droplet of chloroform was added to each lysate to kill any remaining viable cells and the phage were titred using serial dilutions infected into ED8739 cultures and plated on LB top agar supplemented with 10 mM MgSO4 and 0.1% maltose. The plates were grown for 16 hours at 37° C. before the plaques were counted. Both the lambda cI857sam7 and lambda cI857sam7ΔSR prophage gave phage titres of ~1×10$^9$ pfu/mL demonstrating that the deletion of the lambda ΔSR lysis cluster, and the corresponding insertion of a kanamycin gene in the opposite transcriptional direction, did not perturb the structural genes' transcription or translation.

Example 23

Capsid Display on Lambda ΔSR Phage

Capsid display using the lambda gpD gene has been well documented in the literature, as have methods of phage panning for target binding using gpD display. However, the combination of use of capsid display with lysis-defective phage has not been proposed prior to this application. Furthermore, the combination of capsid display with lysis-defective phage in permeabilised cells according to the method of the invention enables screening for target binding to the phage capsid by FACS detection, which is a high-throughput method of clonal characterization.

To demonstrate the binding of target to lysis-defective phage retained within permeabilised cells we fused a sequence encoding a single-chain antibody (scFv) that binds to a GFP-related fluorescent protein, mAG1 (Karasawa et al., 2003), to the 3'-terminus of the lambda gpD gene. The α-mAG1 scFv is a rare class of antibody that is soluble and stable when expressed in the bacterial cytoplasm in a reduced state. A FLAG epitope was fused to the C-terminus of the gpD::α-mAG1 fusion protein and full-length soluble protein was demonstrated to be expressed in the cytoplasm of E. coli cells using an αFLAG monoclonal antibody.

A lambda cosmid was constructed that expressed the gpD::α-mAG1 fusion protein from the araBAD promoter, under repression by the araC protein and inducible by arabinose. The cosmid also contained features common to other cosmid vectors available commercially, and privately, of the lambda cos region (SEQ ID NO:26), bacterial plasmid origin of replication and antibiotic resistance genes (AmpR and Ch1R). It also contained a stuffer fragment to enable in vivo packaging of phage. An example of a commercially-available cosmid vector is pFOS1 (New England BioLabs (NEB)).

The gpD::α-mAG1 cosmid was transformed into an E. coli ED8739 strain containing the λ cI857ΔSR prophage and grown at 30° C. for vegetative growth. To induce the phage functions the strain was cultured in LB media to a low density, then heated to 42° C. for 15 minutes, before growth at 31° C. for 75 minutes. Induction of the gpD::α-mAG1 fusion protein was initiated immediately following the 42° C. incubation by addition of arabinose to 0.2% w/v. At the completion of phage growth and packaging, the cells were permeabilised by the method of the invention by centrifugation and resuspension in 0.3× volumes of LB+0.5% 8TGP for 10 minutes at 25° C. The cells were then re-centrifuged and washed in 1× volume of TBS+10 mM MgSO$_4$ (TBS/Mg), before being pelleted and suspended in TBS/Mg with excess mAG1 protein for 20 minutes. Following mAG1 binding, cells were washed clean of unbound mAG1 with TBS/Mg before being suspended for viewing by microscopy or for FACS analysis.

FIG. 24 demonstrates that the polyvalent lambda display, when encapsulated in permeabilised cells and probed with fluorescent target, generated a sufficiently strong signal for visual detection by fluorescent microscopy. Each bacterial cell demonstrated a punctate labeling of between 10 and 30 foci. These foci were only observed in cells expressing the gpD::α-mAG1 fusion protein and induced for phage. Foci were not observed within cells not expressing the fusion protein, or not induced for phage when probed with mAG1 protein. Similarly, the gpD::α-mAG1-labeled phage did not bind the related fluorescent protein, GFP. Given that a wild-type lambda phage burst size is 100-200 copies per cell, and assuming that the phage are concentrated within just a few regions of the cell, then each foci may contain between 3 and 20 phage. This estimate may be conservative as the burst size from lysis-defective phage may be larger given that the replication is allowed to persist beyond the normal timing of lysis. Therefore, the polyvalent display of the encapsulated, lysis-defective phage, as described by the method of the invention, allows the direct detection of fluorophore-labelled protein binding by light microscopy.

As the sensitivity of FACS instrumentation is superior to conventional microscopy imaging then it was to be expected that detection and collection of cells containing labeled phage, from those which were unlabeled, would be easily performed given the strength of the signal already observed by light microscopy. FIG. 25 demonstrates the fluorescence graph for 100 K events on an Influx FACS (BD Biosciences) with an input of ~1% of α-mAG1-positive cells. The cell population has been co-stained with the DNA binding dye, Gel Red, and the fluorescent mAG1 protein. The P2 gated population is α-mAG1-positive and the P3 gated population is α-mAG1-negative.

The post-FACS output was recovered by the addition of ReadyLyse enzyme followed by infection into ED8739λ cI857ΔSR cells. Recovery was recorded at about 10 phage particles per positive event.

Therefore, high-throughput FACS screening of encapsulated capsid-display phage is made possible using the method of the invention.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Aharoni et al. (2005) Chem Biol, 12:1281-1289
Barondess and Beckwith (1995) J Bact, 177:1247-1253
Becker et al. (2004) Curr Opin Biot, 15:323-329
Bertani (1968) Virology, 36:87-103
Bradley et al. (1975) Mol Gen Genet, 140:123-135
Briani et al. (2001) Plasmid, 45:1-17
Briers et al. (2009) Biochem Biophys Res Comm, 383:187-191
Chang et al. (2008) Virology, 370:352-361
Chen and Gotschlich (2001) J Bact, 183: 3160-3168
Cherepanov and Wackernagel (1995) Gene, 158:9-14
Dai et al. (2008) Prot Eng Design Sel, 23:413-424
Daugherty et al. (2000) J Immunol Methods, 243:211-227
Farinas (2006) Comb Chem High Thro Screen, 9:321-328
George, et al. (2003) Protein Engineering, 15:871-879
Gupta et al. (2003) J Mol Biol, 334:241-254
Hamilton et al. (1989) J Bact, 171:4617-4622
Kahn et al. (1991) Meth Enzy, 204:264-280
Karasawa et al. (2003) J Biol Chem, 36:34167-34171
Kenrick et al. (2007) Curr Prot Cyt, 4.6.1-4.6.27
Kim and Song (2006) J Micro, 44:530-536
King et al. (1982) Mol Gen Genet, 186:548-557
Levy et al. (2007) J Imm Meth, 321:164-173
Lindqvist et al. (1993) Microbiol Rev, 57:683-702
Lindqvist and Naderi (1995) FEMS Micro Rev, 17:33-39
Liu et al. (1997) J Virol, 71:4502-4508
Lutz and Patrick (2004) Curr Opin Biot, 15:291-297
Magnet et al. (2007) J Bact, 189:3927-3931
Maruyama et al. (1994) Proc Natl Acad Sci USA 91:8273-8277
Mikawa et al. (1996) J Mol Bio, 262:21-30
Miller et al. (2006) Nat Meth, 3:561-570
Montigiani et al. (1996) J Mol Biol, 258:6-13
Parsons et al. (2006) Biochem, 45:2122-2128
Rao et al. (2007) J Mol Biol, 370:1006-1019
Santini et al. (1998) J Mol Biol. 282:125-135
Sasaki and Bertani (1965) J Gen Micro, 40:365-376
Sauer et al. (1982) Vir, 116:523-534
Schaefer et al. (2010) Antibody Eng, 1:21-44
Smith (1985) Science, 228:1315-1317
Sternberg and Hoess (1995) Poc Natl Acad Sci USA, 92:1609-1613
Vaccaro et al. (2006) J Imm Meth, 310:149-158
Wiman et al. (1970) Mol Gen Genetics, 107:1-31
Woods and Egan (1974) J Vir, 14:1349-1356
Yankovsky et al. (1989) Gene, 81:203-210
Younghusband et al. (1975) Mol Gen Genetics, 140:101-110
Zierman et al. (1994) J Bacteriol, 176:4974-4984

The invention claimed is:

1. A method of screening a polypeptide for a desired activity against a target molecule, the method comprising:
   a) culturing a Gram-negative bacterial cell comprising an exogenous polynucleotide encoding the polypeptide such that the polypeptide is produced in the cell,
   b) allowing a lysis-defective phage to package the polynucleotide encoding the polypeptide, wherein the lysis-defective phage is retained within the bacterial cell,
   c) permeabilising:
      i) the outer membrane of the bacterial cell, or
      ii) the inner and outer membranes of the bacterial cell,
   d) contacting the bacterial cell with the target molecule, and
   e) screening the polypeptide for the desired activity, wherein the polypeptide is retained within the bacterial cell by the bacterial cell wall or inner membrane and/or the polypeptide is attached to the bacterial cell wall or inner membrane.

2. The method of claim 1, wherein the polypeptide is associated with at least a second polypeptide to form a protein complex that is retained within the permeabilised bacterial cell and/or is attached to the bacterial cell wall.

3. The method of claim 2, wherein the polypeptide is fused to the second polypeptide or a subunit thereof.

4. The method of claim 1, wherein the inner and outer bacterial membranes are permeabilised with one or more detergents or an organic solvent.

5. The method of claim 4, wherein the detergent is a non-ionic detergent.

6. The method of claim 4, wherein the organic solvent is chloroform.

7. The method of claim 1, wherein:
   i) the bacterial outer membrane is permeabilised;
   ii) the bacterial cell wall is at least partially hydrolysed; and
   iii) the polypeptide is attached to the inner membrane.

8. The method of claim 1, wherein the polynucleotide encoding the polypeptide is a plasmid, cosmid, phagemid or phage DNA.

9. The method of claim 1, wherein the lysis-defective phage is a temperate phage selected from lambda phage, 186, P2, a hybrid of 186 and P2, and P4 and/or wherein the lysis-defective phage is a prophage.

10. The method of claim 9, wherein allowing the lysis-defective phage to package the polynucleotide comprises inducing activation of the prophage in the bacterial cell to produce phage, wherein the phage package the polynucleotide and/or wherein inducing activation of the prophage comprises producing one or more phage activator proteins in the bacterial cell.

11. The method of claim 10, wherein inducing activation of the prophage comprises inactivating one or more phage repressor proteins in the bacterial cell.

12. The method of claim 11, wherein the phage is lysis-defective due to deletion or mutation to an inactive form of the lysozyme gene, or deletion or mutation to an inactive form of the holin and lysozyme genes.

13. The method of claim 11, wherein the bacterial cell comprises lambda prophage and inducing activation of the prophage comprises inactivating a temperature-sensitive repressor allele of protein cI in the bacterial cell.

14. The method of claim 1, wherein the method further comprises an additional screening of the polypeptide for a desired activity against a target molecule in a Gram-negative bacterial cell, wherein
   i) the polynucleotide encoding the polypeptide is not packaged into a lysis-defective phage, and/or
   ii) the polypeptide is not retained within the bacterial cell by the bacterial cell wall and/or attached to the bacterial cell wall.

15. The method of claim 14, wherein the additional screening is performed using a lytic or temperate phage to package the polynucleotide encoding the polypeptide.

16. The method of claim 15, wherein the bacterial cell in the additional screening is lysed to release the phage.

17. The method of claim 16, wherein the phage in the additional screening is a lytic phage which lyses the bacterial cell.

18. The method of claim 17, wherein
   i) the lytic phage comprises a first binding partner on the phage coat, and
   ii) the polypeptide being screened for a desired activity is a fusion protein comprising a second binding partner, wherein the fusion protein comprising the second binding partner binds to the first binding partner on the lytic phage coat.

19. The method of claim 18, wherein the lytic phage is lambda phage.

20. The method of claim 18, wherein the first binding partner is calmodulin and the second binding partner is calmodulin binding peptide.

* * * * *

SEQUENCE LISTING

```
<160> NUMBER OF SEQ ID NOS: 27

<210> SEQ ID NO 1
<211> LENGTH: 4641
<212> TYPE: DNA
<213> ORGANISM: Artificial Sequence
<220> FEATURE:
<223> OTHER INFORMATION: Vector

<400> SEQUENCE: 1 ggttttcgc cctttgacgt tggagtccac gttctttaat agtggactct tgttccaaac      60
tggaacaaca ctcaacccta tctcggtcta ttcttttgat ttataaggga ttttgccgat    120
ttcggcctat tggttaaaaa atgagctgat ttaacaaaaa tttaacgcga attttaacaa    180
aatattaacg cttacaattt aggtggcact tttcggggaa atgtgcgcgg aacccctatt    240
tgtttatttt tctaaataca ttcaaatatg tatccgctca tgagacaata accctgataa    300
atgcttcaat aatattgaaa aaggaagagt atgagtattc aacatttccg tgtcgccctt    360 attcccttttt ttgcggcatt ttgccttcct gttttgctc acccagaaac gctggtgaaa    420
gtaaaagatg ctgaagatca gttgggtgca cgagtgggtt acatcgaact ggatctcaac    480
agcggtaaga tccttgagag ttttcgcccc gaagaacgtt ttccaatgat gagcactttt    540
aaagttctgc tatgtggcgc ggtattatcc cgtattgacg ccgggcaaga gcaactcggt    600
cgccgcatac actattctca gaatgacttg gttgagtact caccagtcac agaaaagcat    660
cttacggatg gcatgacagt aagagaatta tgcagtgctg ccataaccat gagtgataac    720
```

```
actgcggcca acttacttct gacaacgatc ggaggaccga aggagctaac cgctttttg    780
cacaacatgg gggatcatgt aactcgcctt gatcgttggg aaccggagct gaatgaagcc    840
ataccaaacg acgagcgtga caccacgatg cctgtagcaa tggcaacaac gttgcgcaaa    900
ctattaactg gcgaactact tactctagct tcccggcaac aattaataga ctggatggag    960
gcggataaag ttgcaggacc acttctgcgc tcggcccttc cggctggctg gtttattgct   1020
gataaatctg gagccggtga gcgtgggtct cgcggtatca ttgcagcact ggggccagat   1080
ggtaagccct cccgtatcgt agttatctac acgacgggga gtcaggcaac tatggatgaa   1140
cgaaatagac agatcgctga gataggtgcc tcactgatta gcattggta actgtcagac    1200
caagtttact catatatact ttagattgat ttaaaacttc attttaatt taaaaggatc   1260
taggtgaaga tccttttga taatctcatg accaaaatcc cttaacgtga gttttcgttc   1320
cactgagcgt cagaccccgt agaaaagatc aaaggatctt cttgagatcc ttttttctg    1380
cgcgtaatct gctgcttgca acaaaaaaaa ccaccgctac cagcggtggt ttgtttgccg   1440
gatcaagagc taccaactct ttttccgaag gtaactggct tcagcagagc gcagatacca   1500
aatactgtcc ttctagtgta gccgtagtta ggccaccact tcaagaactc tgtagcaccg   1560
cctacatacc ccgctctgct aatcctgtta ccagtggctg ctgccagtgg cgataagtcg   1620
tgtcttaccg ggttggactc aagacgatag ttaccggata aggcgcagcg gtcgggctga   1680
acggggggtt cgtgcacaca gcccagcttg gagcgaacga cctacaccga actgagatac   1740
ctacagcgtg agctatgcga aagcgccacg cttcccgaag ggagaaaggc ggacaggtat   1800
ccggtaagcg gcagggtcgg agcaggagag cgcacgaggg agcttccagg gggaaacgcc   1860
tggtatcttt atagtcctgt cgggtttcgc cacctctgac ttgagcgtcg attttgtga    1920
tgctcgtcag gggggcggag cctatggaaa aacgccagca acgcggcctt tttacggttc   1980
ctggcctttt gctggccttt tgctcacatg ttctttcctg cgttatcccc tgattctgtg   2040
gataaccgta ttaccgcctt tgagtgagct gataccgctc gccgcagccg aacgaccgag   2100
cgcagcgagt cagtgagcga ggaagcggaa gagcgcccaa tacgcaaacc gcctctcccc   2160
gcgcgtggcc gttcattaat gcagctggca cgacaggttt cccgactgcg gccgcgacac   2220
ggaaatgttg aatactcata ctcttccttt ttcaatatta ttgaagcatt tatcagggtt   2280
attgtctcat gagcggatac atatttgaat gtatttagaa aaataaacaa ataggggttc   2340
cgcgcacatt tccccgaaaa gtgccacctg catcgattta ttatgacaac ttgacggcta   2400
catcattcac tttttcttca aaccggcac ggaactcgct cgggctggcc ccggtgcatt   2460
ttttaaatac ccgcgagaaa tagagttgat cgtcaaaacc aacattgcga ccgacggtgg   2520
cgataggcat ccgggtggtg ctcaaaagca gcttcgcctg gctgatacgt tggtcctcgc   2580
gccagcttaa gacgctaatc cctaactgct ggcggaaaag atgtgacaga cgcgacggcg   2640
acaagcaaac atgctgtgcg acgctggcga tatcaaaatt gctgtctgcc aggtgatcgc   2700
tgatgtactg acaagcctcg cgtacccgat tatccatcgg tggatggagc gactcgttaa   2760
tcgcttccat cgccgcagt aacaattgct caagcagatt tatcggcagc agctccgaat   2820
agcgcccttc cccttgcccg gcgttaatga tttgcccaaa caggtcgctg aaatgcggct   2880
ggtgcgtttc atccgggcga aagaacccg tattggcaaa tattgacggc cagttaagcc   2940
attcatgcca gtaggcgcgc ggacgaaagt aaacccactg gtgataccat tcgcgagcct   3000
ccggatgacg accgtagtga tgaatctctc ctggcgggaa cagcaaaata tcacccggtc   3060
ggcaaacaaa ttctcgtccc tgatttttca ccacccctg accgcgaatg gtgagattga   3120
```

```
gaatataacc tttcattccc agcggtcggt cgataaaaaa atcgagataa ccgttggcct    3180
caatcggcgt taaacccgcc accagatggg cattaaacga gtatcccggc agcagggat    3240 cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
aatgcaccat caccatcacc acggcgcgcc taacctcgag ggtacctcca tggacaaaga    3660
ttgcgaaatg aaacgtacca ccctggatag cccgctgggc aaactggaac tgagcggctg    3720
cgaacagggc ctgcatgaaa ttaaactgct gggtaaaggc accagcgcgg ccgatgcggt    3780
tgaagttccg gcccccggccg ccgtgctggg tggtccggaa ccgctgatgc aggcgaccgc    3840
gtggctgaac gcgtattttc atcagccgga agcgattgaa gaatttccgg ttccggcgct    3900
gcatcatccg gtgtttcagc aggagagctt tacccgtcag gtgctgtgga actgctgaa    3960 agtggttaaa tttggcgaag tgattagcta tcagcagctg gcggcccctgg cgggtaatcc    4020 ggcggccacc gccgccgtta aaaccgcgct gagcggtaac ccggtgccga ttctgattcc    4080
gtgccatcgt gtggttagct ctagcggtgc ggttggcggt tatgaaggtg gtctggcggt    4140
gaaagagtgg ctgctggccc atgaaggtca tcgtctgggt aaaccgggtc tgggacctgc    4200
agggtaaaag cttgaattcg cgcgctcact ggccgtcgtt ttacaacgtc gtgactggga    4260
aaaccctggc gttacccaac ttaatcgcct tgcagcacat ccccctttcg ccagctggcg    4320
taatagcgaa gaggcccgca ccgatcgccc ttcccaacag ttgcgcagcc tgaatggcga    4380
atgggacgcg ccctgtagcg gcgcattaag cgcggcgggt gtggtggtta cgcgcagcgt    4440
gaccgctaca cttgccagcg ccctagcgcc cgctcctttc gctttcttcc cttcctttct    4500
cgccacgttc gccggctttc cccgtcaagc tctaaatcgg gggctccctt tagggttccg    4560
atttagtgct ttacggcacc tcgaccccaa aaaacttgat tagggtgatg gttcacgtag    4620
tgggccatcg ccctgataga c                                              4641
```

<210> SEQ ID NO 2
<211> LENGTH: 5082
<212> TYPE: DNA
<213> ORGANISM: Artificial Sequence
<220> FEATURE:
<223> OTHER INFORMATION: Vector

<400> SEQUENCE: 2

```
ggtttttcgc cctttgacgt tggagtccac gttctttaat agtggactct tgttccaaac      60
tggaacaaca ctcaaccccta tctcggtcta ttcttttgat ttataaggga ttttgccgat    120
ttcggcctat tggttaaaaa atgagctgat ttaacaaaaa tttaacgcga atttaacaa     180 aatattaacg cttacaattt aggtggcact tttcgggaa atgtgcgcgg aaccccctatt    240 tgtttatttt tctaaataca ttcaaatatg tatccgctca tgagacaata accctgataa    300
atgcttcaat aatattgaaa aaggaagagt atgagtattc aacatttccg tgtcgccctt    360 attcccttt ttgcggcatt ttgccttcct gtttttgctc acccagaaac gctggtgaaa      420
gtaaaagatg ctgaagatca gttgggtgca cgagtgggtt acatcgaact ggatctcaac    480
agcggtaaga tccttgagag ttttcgcccc gaagaacgtt ttccaatgat gagcactttt    540
```

```
aaagttctgc tatgtggcgc ggtattatcc cgtattgacg ccgggcaaga gcaactcggt      600
cgccgcatac actattctca gaatgacttg gttgagtact caccagtcac agaaaagcat      660
cttacggatg gcatgacagt aagagaatta tgcagtgctg ccataaccat gagtgataac      720
actgcggcca acttacttct gacaacgatc ggaggaccga aggagctaac cgcttttttg      780
cacaacatgg gggatcatgt aactcgcctt gatcgttggg aaccggagct gaatgaagcc      840
ataccaaacg acgagcgtga caccacgatg cctgtagcaa tggcaacaac gttgcgcaaa      900
ctattaactg gcgaactact tactctagct tcccggcaac aattaataga ctggatggag      960
gcggataaag ttgcaggacc acttctgcgc tcggcccttc cggctggctg gtttattgct     1020
gataaatctg gagccggtga gcgtgggtct cgcggtatca ttgcagcact ggggccagat     1080
ggtaagccct cccgtatcgt agttatctac acgacgggga gtcaggcaac tatggatgaa     1140
cgaaatagac agatcgctga gataggtgcc tcactgatta gcattggta actgtcagac      1200 caagtttact catatatact ttagattgat ttaaaacttc attttttaatt taaaaggatc     1260 taggtgaaga tccttttttga taatctcatg accaaaatcc cttaacgtga gttttcgttc     1320
cactgagcgt cagaccccgt agaaaagatc aaaggatctt cttgagatcc ttttttttctg     1380 cgcgtaatct gctgcttgca acaaaaaaaa ccaccgctac cagcggtggt ttgtttgccg     1440
gatcaagagc taccaactct ttttccgaag gtaactggct tcagcagagc gcagatacca     1500
aatactgtcc ttctagtgta gccgtagtta ggccaccact tcaagaactc tgtagcaccg     1560
cctacatacc cgctctgct aatcctgtta ccagtggctg ctgccagtgg cgataagtcg     1620
tgtcttaccg ggttggactc aagacgatag ttaccggata aggcgcagcg gtcgggctga     1680
acggggggtt cgtgcacaca gcccagcttg gagcgaacga cctacaccga actgagatac     1740
ctacagcgtg agctatgcga aagcgccacg cttcccgaag ggagaaaggc ggacaggtat     1800
ccggtaagcg gcagggtcgg agcaggagag cgcacgaggg agcttccagg gggaaacgcc     1860
tggtatcttt atagtcctgt cgggtttcgc cacctctgac ttgagcgtcg attttttgtga     1920 tgctcgtcag gggggcggag cctatggaaa aacgccagca acgcggcctt tttacggttc     1980
ctggcctttt gctggccttt tgctcacatg ttctttcctg cgttatcccc tgattctgtg     2040
gataaccgta ttaccgcctt tgagtgagct gataccgctc gccgcagccg aacgaccgag     2100
cgcagcgagt cagtgagcga ggaagcggaa gagcgcccaa tacgcaaacc gcctctcccc     2160
gcgcgtggcc gttcattaat gcagctggca cgacaggttt cccgactgcg ccgcgacac     2220 ggaaatgttg aatactcata ctcttccttt ttcaatatta ttgaagcatt tatcagggtt     2280
attgtctcat gagcggatac atatttgaat gtatttagaa aaataaacaa ataggggttc     2340
cgcgcacatt tccccgaaaa gtgccacctg catcgattta ttatgacaac ttgacggcta     2400
catcattcac ttttttcttca caaccggcac ggaactcgct cgggctggcc ccggtgcatt     2460
ttttaaatac ccgcgagaaa tagagttgat cgtcaaaacc aacattgcga ccgacggtgg     2520
cgataggcat ccgggtggtg ctcaaaagca gcttcgcctg gctgatacgt tggtcctcgc     2580
gccagcttaa gacgctaatc cctaactgct ggcggaaaag atgtgacaga cgcgacggcg     2640
acaagcaaac atgctgtgcg acgctggcga tatcaaaatt gctgtctgcc aggtgatcgc     2700
tgatgtactg acaagcctcg cgtacccgat tatccatcgg tggatggagc gactcgttaa     2760
tcgcttccat gcgccgcagt aacaattgct caagcagatt tatcggcagc agctccgaat     2820
agcgcccttc cccttgcccg gcgttaatga tttgcccaaa caggtcgctg aaatgcggct     2880
ggtgcgtttc atccgggcga aagaaccccg tattggcaaa tattgacggc cagttaagcc     2940
```

-continued

```
attcatgcca gtaggcgcgc ggacgaaagt aaacccactg gtgataccat tcgcgagcct    3000
ccggatgacg accgtagtga tgaatctctc ctggcgggaa cagcaaaata tcacccggtc    3060
ggcaaacaaa ttctcgtccc tgattttttca ccaccccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgcaaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt tggtaagga ggttatctag    3600
aggtaccaac agcccaccga aagtgttacg caagggtgat cgtggcgatg aagtgtgcca    3660
gctgcaaacg ttactgaatc tctgcggtta tgacgttggc aaacctgatg gcattttcgg    3720
caataacacc ttcaaccagg ttgtgaaatt ccagaaggac aactgtttag acagcgatgg    3780
tattgtgggt aaaacacgt gggcagaact gttcagcaaa tactcgccac cgtccatgga    3840
caaagattgc gaaatgaaac gtaccaccct ggatagcccg ctgggcaaac tggaactgag    3900
cggctgcgaa cagggcctgc atgaaattaa actgctgggt aaaggcacca gcgcggccga    3960
tgcggttgaa gttccggccc cggccgccgt gctgggtggt ccggaaccgc tgatgcaggc    4020
gaccgcgtgg ctgaacgcgt attttcatca gccggaagcg attgaagaat tccggttcc    4080
ggcgctgcat catccggtgt ttcagcagga gagctttacc cgtcaggtgc tgtggaaact    4140
gctgaaagtg gttaaatttg gcgaagtgat tagctatcag cagctggcgg ccctggcggg    4200
taatccggcg gccaccgccg ccgttaaaac cgcgctgagc ggtaacccgg tgccgattct    4260
gattccgtgc catcgtgtgg ttagctctag cggtgcggtt ggcggttatg aaggtggtct    4320
ggcggtgaaa gagtggctgc tgcccatga aggtcatcgt ctgggtaaac cgggtctggg    4380
acctgcaggg aactcaggta aaggcgcagt gaacattaac gccgcatcac agcaagaact    4440
ggaggcgtta ccgggtattg gccctgcaaa ggccaaagcg atcgctgaat atcgcgcaca    4500
aaatggcgca ttcaagagcg tcgacgatct gatcaaagtc aagggcatcg gtccggcagt    4560
gctagccaag ctgaaagacc aggcatcagt tggtgcaccg gctcctaaag gtccggccaa    4620
accggtcctg cccgctgtaa agaaattaaa gcttgaattc gcgcgctcac tggccgtcgt    4680
tttacaacgt cgtgactggg aaaaccctgg cgttacccaa cttaatcgcc ttgcagcaca    4740
tccccctttc gccagctggc gtaatagcga agaggcccgc accgatcgcc ctttcccaaca    4800
gttgcgcagc ctgaatggcg aatgggacgc gccctgtagc ggcgcattaa gcgcggcggg    4860
tgtggtggtt acgcgcagcg tgaccgctac acttgccagc gccctagcgc ccgctccttt    4920
cgctttcttc ccttccttc tcgccacgtt cgccggcttt cccgtcaag ctctaaatcg    4980
ggggctccct ttagggttcc gatttagtgc tttacggcac ctcgacccca aaaaacttga    5040
ttagggtgat ggttcacgta gtgggccatc gccctgatag ac                      5082
```

<210> SEQ ID NO 3
<211> LENGTH: 4855
<212> TYPE: DNA
<213> ORGANISM: Artificial Sequence
<220> FEATURE:
<223> OTHER INFORMATION: Vector -continued

```
<400> SEQUENCE: 3 ggttttttcgc cctttgacgt tggagtccac gttctttaat agtggactct tgttccaaac      60
tggaacaaca ctcaaccctc tctcggtcta ttcttttgat ttataaggga ttttgccgat     120
ttcggcctat tggttaaaaa atgagctgat ttaacaaaaa tttaacgcga attttaacaa     180
aatattaacg cttacaattt aggtggcact tttcggggaa atgtgcgcgg aaccccctatt     240 tgtttatttt tctaaataca ttcaaatatg tatccgctca tgagacaata accctgataa     300
atgcttcaat aatattgaaa aggaagagt atgagtattc aacatttccg tgtcgccctt     360
attccctttt ttgcggcatt ttgccttcct gtttttgctc acccagaaac gctggtgaaa     420
gtaaaagatg ctgaagatca gttgggtgca cgagtgggtt acatcgaact ggatctcaac     480
agcggtaaga tccttgagag ttttcgcccc gaagaacgtt ttccaatgat gagcactttt     540
aaagttctgc tatgtggcgc ggtattatcc cgtattgacg ccgggcaaga gcaactcggt     600
cgccgcatac actattctca gaatgacttg gttgagtact caccagtcac agaaaagcat     660
cttacggatg gcatgacagt aagagaatta tgcagtgctg ccataaccat gagtgataac     720
actgcggcca acttacttct gacaacgatc ggaggaccga aggagctaac cgcttttttg     780
cacaacatgg gggatcatgt aactcgcctt gatcgttggg aaccggagct gaatgaagcc     840
ataccaaacg acgagcgtga caccacgatg cctgtagcaa tggcaacaac gttgcgcaaa     900
ctattaactg gcgaactact tactctagct tcccggcaac aattaataga ctggatggag     960
gcggataaag ttgcaggacc acttctgcgc tcggcccttc cggctggctg gtttattgct    1020
gataaatctg gagccggtga gcgtgggtct cgcggtatca ttgcagcact ggggccagat    1080
ggtaagccct cccgtatcgt agttatctac acgacgggga gtcaggcaac tatggatgaa    1140
cgaaatagac agatcgctga gataggtgcc tcactgatta gcattggta actgtcagac    1200 caagtttact catatatact ttagattgat ttaaaacttc attttttaatt taaaaggatc    1260 taggtgaaga tcctttttga taatctcatg accaaaatcc cttaacgtga gttttcgttc    1320
cactgagcgt cagaccccgt agaaaagatc aaaggatctt cttgagatcc ttttttttctg    1380 cgcgtaatct gctgcttgca acaaaaaaa ccaccgctac cagcggtggt ttgtttgccg    1440
gatcaagagc taccaactct ttttccgaag gtaactggct tcagcagagc gcagatacca    1500
aatactgtcc ttctagtgta gccgtagtta ggccaccact tcaagaactc tgtagcaccg    1560
cctacatacc cgctctgct aatcctgtta ccagtggctg ctgccagtgg cgataagtcg    1620
tgtcttaccg ggttggactc aagacgatag ttaccggata aggcgcagcg gtcgggctga    1680 acgggggggtt cgtgcacaca gcccagcttg gagcgaacga cctacaccga actgagatac    1740
ctacagcgtg agctatgcga aagcgccacg cttcccgaag ggagaaaggc ggacaggtat    1800
ccggtaagcg gcagggtcgg agcaggagag cgcacgaggg agcttccagg gggaaacgcc    1860
tggtatcttt atagtcctgt cgggtttcgc cacctctgac ttgagcgtcg atttttgtga    1920
tgctcgtcag ggggggcggag cctatggaaa aacgccagca acgcggcctt tttacggttc    1980
ctggcctttt gctggccttt tgctcacatg ttctttcctg cgttatcccc tgattctgtg    2040
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160
gcgcgtggcc gttcattaat gcagctggca cgacaggttt cccgactgcg gccgcgacac    2220
ggaaatgttg aatactcata ctcttccttt ttcaatatta ttgaagcatt tatcagggtt    2280
attgtctcat gagcggatac atatttgaat gtatttagaa aaataaacaa ataggggttc    2340
```

```
cgcgcacatt tccccgaaaa gtgccacctg catcgattta ttatgacaac ttgacggcta    2400
catcattcac ttttttcttca caaccggcac ggaactcgct cgggctggcc ccggtgcatt   2460
ttttaaatac ccgcgagaaa tagagttgat cgtcaaaacc aacattgcga ccgacggtgg    2520
cgataggcat ccgggtggtg ctcaaaagca gcttcgcctg gctgatacgt tggtcctcgc    2580
gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat gcgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga aagaaccccg tattggcaaa tattgacggc cagttaagcc    2940
attcatgcca gtaggcgcgc ggacgaaagt aaacccactg gtgataccat tcgcgagcct    3000
ccggatgacg accgtagtga tgaatctctc ctggcgggaa cagcaaaata tcacccggtc    3060
ggcaaacaaa ttctcgtccc tgattttttca ccacccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcagggggat   3240 cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
catgatgaag cgcaatattc tggcagtgat cgtccctgct ctgttagtag caggtactgc    3660
aaacgctgcc gaatctagac tcgagggtac ctccatggac aaagattgcg aaatgaaacg    3720
taccacctcg gatagcccgc tgggcaaact ggaactgagc ggctgcgaac agggcctgca    3780
tgaaattaaa ctgctgggta aaggcaccag cgccggccgat gcggttgaag ttccggcccc    3840
ggccgccgtg ctgggtggtc cggaaccgct gatgcaggcg accgcgtggc tgaacgcgta    3900
ttttcatcag ccggaagcga ttgaagaatt tccggttccg cgcgctgcatc atccggtgtt    3960 tcagcaggag agctttaccc gtcaggtgct gtggaaactg ctgaaagtgg ttaaatttgg    4020
cgaagtgatt agctatcagc agctggcggc cctggcgggt aatccggcgg ccaccgccgc    4080
cgttaaaacc gcgctgagcg gtaacccggt gccgattctg attccgtgcc atcgtgtggt    4140
tagctctagc ggtgcggttg gcggttatga aggtggtctg gcggtgaaag agtggctgct    4200
ggcccatgaa ggtcatcgtc tgggtaaacc gggtctggga cctgcagggt ccagcaacgc    4260
taaaatcgat cagctgtctt ctgacgttca gactctgaac gctaaagttg accagctgag    4320
caacgacgtg aacgcaatgc gttccgacgt tcaggctgct aaagatgacg cagctcgtgc    4380
taaccagcgt ctggacaaca tggctactaa ataccgcaag taagcttgaa ttcgcgcgct    4440
cactggccgt cgttttacaa cgtcgtgact gggaaaaccc tggcgttacc caacttaatc    4500
gccttgcagc acatccccct ttcgccagct ggcgtaatag cgaagaggcc cgcaccgatc    4560
gcccttccca acagttgcgc agcctgaatg gcgaatggga cgcgccctgt agcggcgcat    4620
taagcgcggc gggtgtggtg gttacgcgca gcgtgaccgc tacacttgcc agcgccctag    4680
cgcccgctcc tttcgctttc ttcccttcct ttctcgccac gttcgccggc tttccccgtc    4740
```

| | |
|---|---|
| aagctctaaa tcgggggctc cctttagggt tccgatttag tgctttacgg cacctcgacc | 4800 |
| ccaaaaaact tgattagggt gatggttcac gtagtgggcc atcgccctga tagac | 4855 |

<210> SEQ ID NO 4
<211> LENGTH: 5931
<212> TYPE: DNA
<213> ORGANISM: Artificial Sequence
<220> FEATURE:
<223> OTHER INFORMATION: Vector

<400> SEQUENCE: 4

| | |
|---|---|
| ggtttttcgc cctttgacgt tggagtccac gttctttaat agtggactct tgttccaaac | 60 |
| tggaacaaca ctcaacccta tctcggtcta ttcttttgat ttataaggga ttttgccgat | 120 |
| ttcggcctat tggttaaaaa atgagctgat ttaacaaaaa tttaacgcga attttaacaa | 180 |
| aatattaacg cttacaattt aggtggcact tttcggggaa atgtgcgcgg aaccccctatt | 240 |
| tgtttatttt tctaaataca ttcaaatatg tatccgctca tgagacaata accctgataa | 300 |
| atgcttcaat aatattgaaa aaggaagagt atgagtattc aacatttccg tgtcgccctt | 360 |
| attccctttt ttgcggcatt ttgccttcct gtttttgctc acccagaaac gctggtgaaa | 420 |
| gtaaaagatg ctgaagatca gttgggtgca cgagtgggtt acatcgaact ggatctcaac | 480 |
| agcggtaaga tccttgagag ttttcgcccc gaagaacgtt ttccaatgat gagcactttt | 540 |
| aaagttctgc tatgtggcgc ggtattatcc cgtattgacg ccgggcaaga gcaactcggt | 600 |
| cgccgcatac actattctca gaatgacttg gttgagtact caccagtcac agaaaagcat | 660 |
| cttacggatg gcatgacagt aagagaatta tgcagtgctg ccataaccat gagtgataac | 720 |
| actgcggcca acttacttct gacaacgatc ggaggaccga aggagctaac cgcttttttg | 780 |
| cacaacatgg gggatcatgt aactcgcctt gatcgttggg aaccggagct gaatgaagcc | 840 |
| ataccaaacg acgagcgtga ccaccacgatg cctgtagcaa tggcaacaac gttgcgcaaa | 900 |
| ctattaactg gcgaactact tactctagct tcccggcaac aattaataga ctggatggag | 960 |
| gcggataaag ttgcaggacc acttctgcgc tcggcccttc cggctggctg gtttattgct | 1020 |
| gataaatctg gagccggtga gcgtgggtct cgcggtatca ttgcagcact ggggccagat | 1080 |
| ggtaagccct cccgtatcgt agttatctac acgacgggga gtcaggcaac tatggatgaa | 1140 |
| cgaaatagac agatcgctga gataggtgcc tcactgatta gcattggta actgtcagac | 1200 |
| caagtttact catatatact ttagattgat ttaaaacttc attttttaatt taaaaggatc | 1260 |
| taggtgaaga tccttttttga taatctcatg accaaaatcc cttaacgtga gttttcgttc | 1320 |
| cactgagcgt cagaccccgt agaaaagatc aaaggatctt cttgagatcc ttttttttctg | 1380 |
| cgcgtaatct gctgcttgca acaaaaaaa ccaccgctac cagcggtggt ttgtttgccg | 1440 |
| gatcaagagc taccaactct ttttccgaag gtaactggct tcagcagagc gcagatacca | 1500 |
| aatactgtcc ttctagtgta gccgtagtta ggccaccact tcaagaactc tgtagcaccg | 1560 |
| cctacatacc cgctctgct aatcctgtta ccagtgctg ctgccagtgg cgataagtcg | 1620 |
| tgtcttaccg ggttggactc aagacgatag ttaccggata aggcgcagcg gtcgggctga | 1680 |
| acggggggtt cgtgcacaca gcccagcttg gagcgaacga cctacaccga actgagatac | 1740 |
| ctacagcgtg agctatgcga aagcgccacg cttcccgaag ggagaaaggc ggacaggtat | 1800 |
| ccggtaagcg gcagggtcgg agcaggagag cgcacgaggg agcttccagg gggaaacgcc | 1860 |
| tggtatcttt atagtcctgt cgggtttcgc cacctctgac ttgagcgtcg attttttgtga | 1920 |
| tgctcgtcag gggggcggag cctatggaaa aacgccagca acgcggcctt tttacggttc | 1980 |

| | |
|---|---|
| ctggcctttt gctggccttt tgctcacatg ttctttcctg cgttatcccc tgattctgtg | 2040 |
| gataaccgta ttaccgcctt tgagtgagct gataccgctc gccgcagccg aacgaccgag | 2100 |
| cgcagcgagt cagtgagcga ggaagcggaa gagcgcccaa tacgcaaacc gcctctcccc | 2160 |
| gcgcgtggcc gttcattaat gcagctggca cgacaggttt cccgactgcg gccgcgacac | 2220 |
| ggaaatgttg aatactcata ctcttccttt ttcaatatta ttgaagcatt tatcagggtt | 2280 |
| attgtctcat gagcggatac atatttgaat gtatttagaa aaataaacaa ataggggttc | 2340 |
| cgcgcacatt tccccgaaaa gtgccacctg catcgattta ttatgacaac ttgacggcta | 2400 |
| catcattcac tttttcttca caaccggcac ggaactcgct cgggctggcc ccggtgcatt | 2460 |
| ttttaaatac ccgcgagaaa tagagttgat cgtcaaaacc aacattgcga ccgacggtgg | 2520 |
| cgataggcat ccgggtggtg ctcaaaagca gcttcgcctg gctgatacgt tggtcctcgc | 2580 |
| gccagcttaa gacgctaatc cctaactgct ggcggaaaag atgtgacaga cgcgacggcg | 2640 |
| acaagcaaac atgctgtgcg acgctggcga tatcaaaatt gctgtctgcc aggtgatcgc | 2700 |
| tgatgtactg acaagcctcg cgtacccgat tatccatcgg tggatggagc gactcgttaa | 2760 |
| tcgcttccat gcgccgcagt aacaattgct caagcagatt tatcgccagc agctccgaat | 2820 |
| agcgcccttc cccttgcccg gcgttaatga tttgcccaaa caggtcgctg aaatgcggct | 2880 |
| ggtgcgcttc atccgggcga agaaccccg tattggcaaa tattgacggc cagttaagcc | 2940 |
| attcatgcca gtaggcgcgc ggacgaaagt aaacccactg gtgataccat cgcgagcct | 3000 |
| ccggatgacg accgtagtga tgaatctctc ctggcgggaa cagcaaaata tcacccggtc | 3060 |
| ggcaaacaaa ttctcgtccc tgatttttca ccacccctg accgcgaatg gtgagattga | 3120 |
| gaatataacc tttcattccc agcggtcggt cgataaaaaa atcgagataa ccgttggcct | 3180 |
| caatcggcgt taaacccgcc accagatggg cattaaacga gtatcccggc agcaggggat | 3240 |
| cattttgcgc ttcagccata cttttcatac tcccgccatt cagagaagaa accaattgtc | 3300 |
| catattgcat cagacattgc cgtcactgcg tcttttactg gctcttctcg ctaaccaaac | 3360 |
| cggtaacccc gcttattaaa agcattctgt aacaaagcgg gaccaaagcc atgacaaaaa | 3420 |
| cgcgtaacaa aagtgtctat aatcacggca gaaaagtcca cattgattat ttgcacggcg | 3480 |
| tcacactttg ctatgccata gcatttttat ccataagatt agcggatcct acctgacgct | 3540 |
| ttttatcgca actctctact gtttctccat acccgttttt ttggtaagga ggttatctag | 3600 |
| aatgcaccat caccatcacc acggcgcgcc taacctcgag ggtacctcca tggacaaaga | 3660 |
| ttgcgaaatg aaacgtacca ccctggatag cccgctgggc aaactggaac tgagcggctg | 3720 |
| cgaacagggc ctgcatgaaa ttaaactgct gggtaaaggc accagcgcgg ccgatgcggt | 3780 |
| tgaagttccg gcccggccg ccgtgctggg tggtccggaa ccgctgatgc aggcgaccgc | 3840 |
| gtggctgaac gcgtattttc atcagccgga agcgattgaa gaatttccgg ttccggcgct | 3900 |
| gcatcatccg gtgtttcagc aggagagctt tacccgtcag gtgctgtgga aactgctgaa | 3960 |
| agtggttaaa tttggcgaag tgattagcta tcagcagctg gcggccctgg cgggtaatcc | 4020 |
| ggcggccacc gccgccgtta aaaccgcgct gagcggtaac ccgtgccga ttctgattcc | 4080 |
| gtgccatcgt gtggttagct ctagcggtgc ggttggcggt tatgaaggtg gtctggcggt | 4140 |
| gaaagagtgg ctgctggccc atgaaggtca tcgtctgggt aaaccgggtc tgggacctgc | 4200 |
| acaagattac aaagatgacg acgataagtc tgcagggatg accactcaac tggaacaggc | 4260 |
| ctgggagcta gcgaaacagc gtttcgcggc ggtggggatt gatgtcgagg aggcgctgcg | 4320 |
| ccaacttgat cgtttacccg tttcaatgca ctgctggcag ggcgatgatg tttccggttt | 4380 |

```
tgaaaacccg gaaggttcgc tgaccggggg gattcaggcc acaggcaatt atccgggcaa    4440
agcgcgtaat gccagtgagc tacgtgccga tctggaacag gctatgcggc tgattccggg    4500
gccgaaacgg cttaatttac atgccatcta tctggaatca gatacgccag tctcgcgcga    4560
ccagatcaaa ccagagcact tcaaaaactg ggttgaatgg gcgaaagcca atcagctcgg    4620
tctggatttt aacccctcct gcttttcgca tccgctaagc gccgatggct ttacgctttc    4680
ccatgccgac gacagcattc gccagttctg gattgatcac tgcaaagcca gccgtcgcgt    4740
ttcggcctat tttggcgagc aactcggcac accatcggtg atgaacatct ggatcccgga    4800
tggtatgaaa gatatcaccg ttgaccgtct cgccccgcgt cagcgtctgc tggcagcact    4860
ggatgaggtg atcagcgaga agctaaaccc tgcgcaccat atcgacgccg ttgagagcaa    4920
attgtttggc attggcgcag agagctacac ggttggctcc aatgagtttt acatggggta    4980
tgccaccagc cgccagactg cgctgtgcct ggacgccggg cacttccacc cgactgaagt    5040
gatttccgac aagatttccg ccgccatgct gtatgtgccg cagttgctgc tgcacgtcag    5100
ccgtccggtt cgctgggaca gcgatcacgt agtgctgctg gatgatgaaa cccaggcaat    5160
tgccagtgag attgtgcgtc acgatctgtt tgaccgggtg catatcggcc ttgacttctt    5220
cgatgcctct atcaaccgca ttgccgcgtg ggtcattggt acacgcaata tgaaaaaagc    5280
cctgctgcgt gcgttgctgg aacctaccgc tgagctgcgc aagctggaag cgccgggcga    5340
ttacactgcg cgtctggcac tgctggaaga gcagaaatcg ttgccgtggc aggcggtctg    5400
ggaaatgtat tgccaacgtc acgatacgcc agcaggtagc gaatggctgg agagcgtgcg    5460
ggcttatgag aaagaaattt tgagtcgccg cgggtaaaag cttgaattcg cgcgctcact    5520
ggccgtcgtt ttacaacgtc gtgactggga aaaccctggc gttacccaac ttaatcgcct    5580
tgcagcacat ccccctttcg ccagctggcg taatagcgaa gaggcccgca ccgatcgccc    5640
ttcccaacag ttgcgcagcc tgaatggcga atgggacgcg ccctgtagcg gcgcattaag    5700
cgcggcgggt gtggtggtta cgcgcagcgt gaccgctaca cttgccagcg ccctagcgcc    5760
cgctcctttc gctttcttcc cttcctttct cgccacgttc gccggctttc cccgtcaagc    5820
tctaaatcgg gggctccctt tagggttccg atttagtgct ttacggcacc tcgaccccaa    5880
aaaacttgat tagggtgatg gttcacgtag tgggccatcg ccctgataga c              5931
```

<210> SEQ ID NO 5
<211> LENGTH: 48
<212> TYPE: DNA
<213> ORGANISM: Artificial Sequence
<220> FEATURE:
<223> OTHER INFORMATION: coding sequence for randmised spacer

<400> SEQUENCE: 5

```
ggtaccgcyg cygkkwtbgc kwtbgkkgkk gckgkkgcyg cyggtctg                    48
```

<210> SEQ ID NO 6
<211> LENGTH: 12
<212> TYPE: PRT
<213> ORGANISM: Artificial Sequence
<220> FEATURE:
<223> OTHER INFORMATION: peptide linker

<400> SEQUENCE: 6

Gly Ser Asn Ser Asn Asn Gln Ser Lys Pro Ser Ser
1               5                   10

```
<210> SEQ ID NO 7
<211> LENGTH: 12
<212> TYPE: PRT
<213> ORGANISM: Artificial Sequence
<220> FEATURE:
<223> OTHER INFORMATION: peptide linker

<400> SEQUENCE: 7

Gly Gly Pro Arg Asn Pro Gln Arg His Thr Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: peptide linker

<400> SEQUENCE: 8

Ser Gly Thr Arg His His Asn Ser His Asn Ser Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: peptide linker

<400> SEQUENCE: 9

Ser Ser Asn Arg Thr His Lys Ser Asn Asn Ser Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: peptide linker

<400> SEQUENCE: 10

Ser Gly His Arg Thr Thr Glu Arg Lys His Ser Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: peptide linker

<400> SEQUENCE: 11

Gly Gly His Arg His Thr Gln Arg His Asn Gly Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: peptide linker

<400> SEQUENCE: 12

Gly Gly Pro Arg Thr Pro Gln Ser Gln Pro Ser Gly
1               5                   10
```

<210> SEQ ID NO 13
<211> LENGTH: 456
<212> TYPE: PRT
<213> ORGANISM: Artificial Sequence
<220> FEATURE:
<223> OTHER INFORMATION: I27::RL6::KzPG::SNAP::DBP

<400> SEQUENCE: 13

```
Ser Leu Ile Glu Val Glu Lys Pro Leu Tyr Gly Val Glu Val Phe Val
1               5                   10                  15

Gly Glu Thr Ala His Phe Glu Ile Glu Leu Ser Glu Pro Asp Val His
            20                  25                  30

Gly Gln Trp Lys Leu Lys Gly Gln Pro Leu Thr Ala Ser Pro Asp Cys
        35                  40                  45

Glu Ile Ile Glu Asp Gly Lys Lys His Ile Leu Ile Leu His Asn Cys
    50                  55                  60

Gln Leu Gly Met Thr Gly Glu Val Ser Phe Gln Ala Ala Asn Ala Lys
65                  70                  75                  80

Ser Ala Ala Asn Leu Lys Val Lys Glu Leu Asn Ser Ser Ser Gln Thr
                85                  90                  95

Ser Gly Thr Arg His His Asn Ser His Asn Ser Ser Gly Thr Asn Ser
            100                 105                 110

Pro Pro Lys Val Leu Arg Lys Gly Asp Arg Gly Asp Glu Val Cys Gln
        115                 120                 125

Leu Gln Thr Leu Leu Asn Leu Cys Gly Tyr Asp Val Gly Lys Pro Asp
    130                 135                 140

Gly Ile Phe Gly Asn Asn Thr Phe Asn Gln Val Val Lys Phe Gln Lys
145                 150                 155                 160

Asp Asn Cys Leu Asp Ser Asp Gly Ile Val Gly Lys Asn Thr Trp Ala
                165                 170                 175

Glu Leu Phe Ser Lys Tyr Ser Pro Pro Ser Met Asp Lys Asp Cys Glu
            180                 185                 190

Met Lys Arg Thr Thr Leu Asp Ser Pro Leu Gly Lys Leu Glu Leu Ser
        195                 200                 205

Gly Cys Glu Gln Gly Leu His Glu Ile Lys Leu Leu Gly Lys Gly Thr
    210                 215                 220

Ser Ala Ala Asp Ala Val Glu Val Pro Ala Pro Ala Ala Val Leu Gly
225                 230                 235                 240

Gly Pro Glu Pro Leu Met Gln Ala Thr Ala Trp Leu Asn Ala Tyr Phe
                245                 250                 255

His Gln Pro Glu Ala Ile Glu Glu Phe Pro Val Pro Ala Leu His His
            260                 265                 270

Pro Val Phe Gln Gln Glu Ser Phe Thr Arg Gln Val Leu Trp Lys Leu
        275                 280                 285

Leu Lys Val Val Lys Phe Gly Glu Val Ile Ser Tyr Gln Gln Leu Ala
    290                 295                 300

Ala Leu Ala Gly Asn Pro Ala Ala Thr Ala Ala Val Lys Thr Ala Leu
305                 310                 315                 320

Ser Gly Asn Pro Val Pro Ile Leu Ile Pro Cys His Arg Val Val Ser
                325                 330                 335

Ser Ser Gly Ala Val Gly Gly Tyr Glu Gly Gly Leu Ala Val Lys Glu
            340                 345                 350

Trp Leu Leu Ala His Glu Gly His Arg Leu Gly Lys Pro Gly Leu Gly
        355                 360                 365
```

```
        Pro Ala Gly Asn Ser Gly Lys Gly Ala Val Asn Ile Asn Ala Ala Ser
            370                 375                 380

Gln Gln Glu Leu Glu Ala Leu Pro Gly Ile Gly Pro Ala Lys Ala Lys
        385                 390                 395                 400

Ala Ile Ala Glu Tyr Arg Ala Gln Asn Gly Ala Phe Lys Ser Val Asp
                        405                 410                 415

Asp Leu Ile Lys Val Lys Gly Ile Gly Pro Ala Val Leu Ala Lys Leu
                    420                 425                 430

Lys Asp Gln Ala Ser Val Gly Ala Pro Ala Pro Lys Gly Pro Ala Lys
                        435                 440                 445

Pro Val Leu Pro Ala Val Lys Lys
            450                 455

<210> SEQ ID NO 14
<211> LENGTH: 1371
<212> TYPE: DNA
<213> ORGANISM: Artificial Sequence
<220> FEATURE:
<223> OTHER INFORMATION: I27::RL6::KzPG::SNAP::DBP coding sequence

<400> SEQUENCE: 14
agcctgattg aagttgaaaa accgttgtac ggcgtggagg tgttcgtcgg cgagactgcc        60
cacttcgaaa ttgaactgag cgaaccggac gttcatggtc agtggaagct gaagggtcag       120
ccgctgaccg cgagcccgga ctgcgagatc atcgaggatg gtaagaagca tattctgatc       180
ctgcacaatt gtcagctggg tatgaccggc gaggtcagct ttcaagctgc gaacgcaaaa       240
agcgcagcga atttgaaagt taagagctg aactcgagca gccagaccag cggcaccgc         300 caccacaata gccataacag cagcggtacc aacagcccac cgaaagtgtt acgcaagggt       360
gatcgtggcg atgaagtgtg ccagctgcaa acgttactga atctctgcgg ttatgacgtt       420
ggcaaacctg atggcatttt cggcaataac accttcaacc aggttgtgaa attccagaag       480
gacaactgtt tagacagcga tggtattgtg ggtaaaaaca cgtgggcaga actgttcagc       540
aaatactcgc caccgtccat ggacaaagat tgcgaaatga aacgtaccac cctggatagc       600
ccgctgggca aactggaact gagcggctgc gaacagggcc tgcatgaaat taaactgctg       660
ggtaaaggca ccagcgcggc cgatgcggtt gaagttccgg ccccggccgc cgtgctgggt       720
ggtccggaac cgctgatgca ggcgaccgcg tggctgaacg cgtatttttca tcagccggaa       780 gcgattgaag aatttccggt tccggcgctg catcatccgg tgtttcagca ggagagcttt       840
acccgtcagg tgctgtggaa actgctgaaa gtggttaaat ttggcgaagt gattagctat       900
cagcagctgg cggccctggc gggtaatccg gcggccaccg ccgccgttaa aaccgcgctg       960
agcggtaacc cggtgccgat tctgattccg tgccatcgtg tggttagctc tagcggtgcg      1020
gttggcggtt atgaaggtgg tctggcggtg aaagagtggc tgctggccca tgaaggtcat      1080
cgtctgggta aaccgggtct gggacctgca gggaactcag gtaaaggcgc agtgaacatt      1140
aacgccgcat cacagcaaga actggaggcg ttaccgggta ttggccctgc aaaggccaaa      1200
gcgatcgctg aatatcgcgc acaaaatggc gcattcaaga gcgtcgacga tctgatcaaa      1260
gtcaagggca tcggtccggc agtgctagcc aagctgaaag accaggcatc agttggtgca      1320
ccggctccta aggtccggc caaaccggtc ctgcccgctg taaagaaata a                1371

<210> SEQ ID NO 15
<211> LENGTH: 5017
<212> TYPE: DNA
<213> ORGANISM: Artificial Sequence
```

<220> FEATURE:
<223> OTHER INFORMATION: Library scaffold vector

<400> SEQUENCE: 15

```
ggttttcgc cctttgacgt tggagtccac gttctttaat agtggactct tgttccaaac      60
tggaacaaca ctcaaccta tctcggtcta ttcttttgat ttataaggga ttttgccgat     120
ttcggcctat tggttaaaaa atgagctgat ttaacaaaaa tttaacgcga attttaacaa    180
aatattaacg cttacaattt aggtggcact tttcggggaa atgtgcgcgg aacccctatt    240
tgtttatttt tctaaataca ttcaaatatg tatccgctca tgagacaata accctgataa    300
atgcttcaat aatattgaaa aaggaagagt atgagtattc aacatttccg tgtcgccctt    360
attccctttt ttgcggcatt ttgccttcct gtttttgctc acccagaaac gctggtgaaa    420
gtaaaagatg ctgaagatca gttgggtgca cgagtgggtt acatcgaact ggatctcaac    480
agcggtaaga tccttgagag ttttcgcccc gaagaacgtt ttccaatgat gagcactttt    540
aaagttctgc tatgtggcgc ggtattatcc cgtattgacg ccgggcaaga gcaactcggt    600
cgccgcatac actattctca gaatgacttg gttgagtact caccagtcac agaaaagcat    660
cttacggatg gcatgacagt aagagaatta tgcagtgctg ccataaccat gagtgataac    720
actgcggcca acttacttct gacaacgatc ggaggaccga aggagctaac cgcttttttg    780
cacaacatgg ggatcatgt aactcgcctt gatcgttggg aaccggagct gaatgaagcc    840
ataccaaacg acgagcgtga caccacgatg cctgtagcaa tggcaacaac gttgcgcaaa    900
ctattaactg gcgaactact tactctagct tcccggcaac aattaataga ctggatggag    960
gcggataaag ttgcaggacc acttctgcgc tcggcccttc cggctggctg gtttattgct   1020
gataaatctg gagccggtga gcgtgggtct cgcggtatca ttgcagcact ggggccagat   1080
ggtaagccct cccgtatcgt agttatctac acgacgggga gtcaggcaac tatggatgaa   1140
cgaaatagac agatcgctga gataggtgcc tcactgatta gcattggta actgtcagac   1200
caagtttact catatatact ttagattgat ttaaaacttc attttaatt taaaaggatc   1260
taggtgaaga tccttttga taatctcatg accaaaatcc cttaacgtga gttttcgttc   1320
cactgagcgt cagaccccgt agaaaagatc aaaggatctt cttgagatcc ttttttctg   1380
cgcgtaatct gctgcttgca acaaaaaaa ccaccgctac cagcggtggt ttgtttgccg   1440
gatcaagagc taccaactct ttttccgaag gtaactggct tcagcagagc gcagatacca   1500
aatactgtcc ttctagtgta gccgtagtta ggccaccact tcaagaactc tgtagcaccg   1560
cctacatacc cgctctgct aatcctgtta ccagtggctg ctgccagtgg cgataagtcg   1620
tgtcttaccg ggttggactc aagacgatag ttaccggata aggcgcagcg tcgggctga   1680
acgggggtt cgtgcacaca gcccagcttg gagcgaacga cctacaccga actgagatac   1740
ctacagcgtg agctatgcga aagcgccacg cttcccgaag ggagaaaggc ggacaggtat   1800
ccggtaagcg gcagggtcgg agcaggagag cgcacgaggg agcttccagg gggaaacgcc   1860
tggtatcttt atagtcctgt cgggtttcgc cacctctgac ttgagcgtcg attttgtga   1920
tgctcgtcag ggggcggag cctatggaaa aacgccagca acgcggcctt tttacggttc   1980
ctggccttt gctggccttt tgctcacatg ttctttcctg cgttatcccc tgattctgtg   2040
gataaccgta ttaccgcctt tgagtgagct gataccgctc gccgcagccg aacgaccgag   2100
cgcagcgagt cagtgagcga ggaagcggaa gagcgcccaa tacgcaaacc gcctctcccc   2160
gcgcgtggcc gttcattaat gcagctggca cgacaggttt cccgactgcg ccgcgacac   2220
```

-continued

```
ggaaatgttg aatactcata ctcttccttt ttcaatatta ttgaagcatt tatcagggtt      2280
attgtctcat gagcggatac atatttgaat gtatttagaa aaataaacaa ataggggttc      2340
cgcgcacatt tccccgaaaa gtgccacctg catcgattta ttatgacaac ttgacggcta      2400
catcattcac tttttcttca caaccggcac ggaactcgct cgggctggcc ccggtgcatt      2460
ttttaaatac ccgcgagaaa tagagttgat cgtcaaaacc aacattgcga ccgacggtgg      2520
cgataggcat ccgggtggtg ctcaaaagca gcttcgcctg gctgatacgt tggtcctcgc      2580
gccagcttaa gacgctaatc cctaactgct ggcggaaaag atgtgacaga cgcgacggcg      2640
acaagcaaac atgctgtgcg acgctggcga tatcaaaatt gctgtctgcc aggtgatcgc      2700
tgatgtactg acaagcctcg cgtacccgat tatccatcgg tggatggagc gactcgttaa      2760
tcgcttccat gcgccgcagt aacaattgct caagcagatt tatcggcagc agctccgaat      2820
agcgcccttc cccttgcccg cgttaatga  tttgcccaaa caggtcgctg aaatgcggct      2880
ggtgcgtttc atccgggcga aagaaccccg tattggcaaa tattgacggc cagttaagcc      2940
attcatgcca gtaggcgcgc ggacgaaagt aaacccactg gtgataccat cgcgagcct      3000 ccggatgacg accgtagtga tgaatctctc ctggcgggaa cagcaaaata tcacccggtc      3060
ggcaaacaaa ttctcgtccc tgattttca  ccaccccctg accgcgaatg gtgagattga      3120
gaatataacc tttcattccc agcggtcggt cgataaaaaa atcgagataa ccgttggcct      3180
caatcggcgt taaacccgcc accagatggg cattaaacga gtatcccggc agcaggggat      3240
cattttgcgc ttcagccata cttttcatac tcccgccatt cagagaagaa accaattgtc      3300
catattgcat caaacattgc cgtcactgcg tcttttactg gctcttctcg ctaaccaaac      3360 cggtaaccc  gcttattaaa agcattctgt aacaaagcgg gaccaaagcc atgacaaaaa      3420
cgcgtaacaa aagtgtctat aatcacggca gaaaagtcca cattgattat ttgcacggcg      3480
tcacactttg ctatgccata gcatttttat ccataagatt agcggatcct acctgacgct      3540
ttttatcgca actctctact gtttctccat acccgttttt ttggtaagga ggttatctag      3600
aatgggagac gcctaatgaa gttcgtctca gaccagcctg attgaagttg aaaaaccgtt      3660
gtacggcgtg gaggtgttcg tcggcgagac tgcccactc  gaaattgaac tgagcgaacc      3720
ggacgttcat ggtcagtgga agctgaaggg tcagccgctg accgcgagcc cggactgcga      3780
gatcatcgag gatggtaaga agcatattct gatcctgcac aattgtcagc tgggtatgac      3840
cggcgaggtc agctttcaag ctgcgaacgc aaaaagcgca gcgaatttga agttaaaga       3900 gctgaactcg agcagccaga ccagcggcac ccgccaccac aatagccata acagcagcgg      3960
taccaacagc ccaccgaaag tgttacgcaa gggtgatcgt ggcgatgaag tgtgccagct      4020
gcaaacgtta ctgaatctct gcggttatga cgttggcaaa cctgatggca ttttcggcaa      4080
taacaccttc aaccaggttg tgaaattcca gaaggacaac tgtttagaca gcgatggtat      4140
tgtgggtaaa aacacgtggg cagaactgtt cagcaaatac tcgccaccgt ccatggacaa      4200
agattgcgaa atgaaacgta ccaccctgga tagcccgctg gcaaactgg  aactgagcgg      4260 ctgcgaacag ggcctgcatg aaattaaact gctgggtaaa ggcaccagcg cggccgatgc      4320
ggttgaagtt ccgccccggc cgccgtgct  gggtggtccg gaaccgctga tgcaggcgac      4380
cgcgtggctg aacgcgtatt ttcatcagcc ggaagcgatt gaagaatttc cggttccggc      4440
gctgcatcat ccggtgtttc agcaggagag ctttacccgt caggtgctgt ggaaactgct      4500
gaaagtggtt aaatttggcg aagtgattag ctatcagcag ctggcggccc tggcgggtaa      4560
tccggcggcc accgccgccg ttaaaaccgc gctgagcggt aacccggtgc cgattctgat      4620
```

```
tccgtgccat cgtgtggtta gctctagcgg tgcggttggc ggttatgaag gtggtctggc    4680
ggtgaaagag tggctgctgg cccatgaagg tcatcgtctg ggtaaaccgg gtctgggacc    4740
tgcagggaac tcaggtaaag gcgcagtgaa cattaacgcc gcatcacagc aagaactgga    4800
ggcgttaccg ggtattggcc ctgcaaaggc caaagcgatc gctgaatatc gcgcacaaaa    4860
tggcgcattc aagagcgtcg acgatctgat caaagtcaag gcatcggtc cggcagtgct     4920 agccaagctg aaagaccagg catcagttgg tgcaccggct cctaaaggtc cggccaaacc    4980
ggtcctgccc gctgtaaaga aataaaagct tgaattc                             5017

<210> SEQ ID NO 16
<211> LENGTH: 90
<212> TYPE: PRT
<213> ORGANISM: Artificial Sequence
<220> FEATURE:
<223> OTHER INFORMATION: peptide spacer

<400> SEQUENCE: 16

Ser Leu Ile Glu Val Glu Lys Pro Leu Tyr Gly Val Glu Val Phe Val
1               5                   10                  15

Gly Glu Thr Ala His Phe Glu Ile Glu Leu Ser Glu Pro Asp Val His
            20                  25                  30

Gly Gln Trp Lys Leu Lys Gly Gln Pro Leu Thr Ala Ser Pro Asp Cys
        35                  40                  45

Glu Ile Ile Glu Asp Gly Lys Lys His Ile Leu Ile Leu His Asn Cys
    50                  55                  60

Gln Leu Gly Met Thr Gly Glu Val Ser Phe Gln Ala Ala Asn Ala Lys
65                  70                  75                  80

Ser Ala Ala Asn Leu Lys Val Lys Glu Leu
                85                  90

<210> SEQ ID NO 17
<211> LENGTH: 498
<212> TYPE: DNA
<213> ORGANISM: Artificial Sequence
<220> FEATURE:
<223> OTHER INFORMATION: P2 phage K endolysin gene

<400> SEQUENCE: 17
atgccggtaa ttaacacgca tcagaatatc gccgcctttc tcgacatgct ggccgtgtcc     60
gaagggacgg cgaatcatcc actgacgaaa aaccggggct atgacgtgat agtcaccgga    120
ctggacggga agccggaaat tttcaccgac tacagtgacc acccgttcgc acatggccga    180
ccggcgaagg tgtttaaccg tcgcggtgaa aaatccacgg cctccggtcg ctatcagcag    240
ctttacctgt tctggccgca ttaccgcaaa cagcttgccc tgccggattt cagtccgttg    300
tcacaggaca gactcgccat tcagttgatc cgcgaacgcg gagcactgga tgacatccgg    360
gcgggacgca ttgagcgcgc catttcacgc tgtcgcaata tctgggcgtc cctgccgggt    420
gccggttacg gtcagcgtga gcattcactg gaaaaactgg tcaccgtctg gcgtaccgct    480
ggcggcgtac cggcttaa                                                  498

<210> SEQ ID NO 18
<211> LENGTH: 282
<212> TYPE: DNA
<213> ORGANISM: Artificial Sequence
<220> FEATURE:
<223> OTHER INFORMATION: P2 phage Y holin gene
```

<400> SEQUENCE: 18

```
atgacagcag aagaaaaaag cgtcctgtcg cttttcatga ttggggtgct gattgttgtc    60
ggcaaggtgc ttgccggtgg tgaacctatc accccgcgtc tgtttatcgg gcgcatgttg   120
ctcggtggtt ttgtctcgat ggttgccggt gttgttctgg tgcagtttcc tgacctgtca   180
ctgccagcgg tgtgcggcat cggctccatg ctgggtatcg ccggttatca ggtgattgag   240
attgccattc agcgccgctt taagggcagg gggaaacagt aa                      282
```

<210> SEQ ID NO 19
<211> LENGTH: 4260
<212> TYPE: DNA
<213> ORGANISM: Artificial Sequence
<220> FEATURE:
<223> OTHER INFORMATION: pACYC (ChIR)::cI857::P4 delta construct

<400> SEQUENCE: 19

```
cagaatgcag attcttgctc aattgttatc agctatgcgc cgaccagaac accttgccga    60
tcagccaaac gtctcttcag gccactgact agcgataact tccccacaa cggaacaact   120
ctcattgcat gggatcattg gtactgtgg gtttagtggt tgtaaaaaca cctgaccgct   180
atccctgatc agtttcttga aggtaaactc atcaccccca gtctggcta tgcagaaatc   240
acctggctca acagcctgct cagggtcaac gagaattaac attccgtcag gaaagcttgg   300
cttggagcct gttggtgcgg tcatggaatt accttcaacc tcaagccaga atgcagaatc   360
actggctttt ttggttgtgc ttacccatct ctccgcatca cctttggtaa aggttctaag   420
cttaggtgag aacatccctg cctgaacatg agaaaaaaca gggtactcat actcacttct   480
aagtgacggc tgcatactaa ccgcttcata catctcgtag atttctctgg cgattgaagg   540
gctaaattct tcaacgctaa ctttgagaat ttttgtaagc aatgcggcgt tataagcatt   600
taatgcattg atgccattaa ataaagcacc aacgcctgac tgccccatcc ccatcttgtc   660
tgcgacagat tcctgggata agccaagttc attttctctt ttttcataaa ttgctttaag   720
gcgacgtgcg tcctcaagct gctcttgtgt taatggtttc ttttttgtgc tcatacgtta   780
aatctatcac cgcaagggat aaatatctaa caccgtgcgt gttgactatt ttacctctgg   840
cggtgataat ggttgcatgt actaaggagg ttgtatgatt tactgtccgt cgtgtggaca   900
tgttgctcac acccgtcgcg cacatttcat ggacgatggc accaagataa tgattgcaca   960
gtgccggaat atttattgct ctgcgacatt tgaagcgagt gaaagctttt tctctgacag  1020
taaagattca ggaatggaat acatttcagg caaacagaga taccgcgatt cactgacgtc  1080
agcctcctgc ggtatgaaac gcccgaaaag aatgcttgtt accggatatt gttgtcggag  1140
atgtaaaggc cttgcactgt caagaacatc gcggcgtctg tctcaggaag tcaccgagcg  1200
tttttatgtg tgcacggatc cgggctgtgg tctggtgttt aaaacgcttc agaccatcaa  1260
ccgcttcatt gtccgcccgg tcacgccgga cgaactggca gaacgcctgc atgaaaaaca  1320
ggaactgccg ccagtacggt taaaaacaca atcatattcg ctgcgtctgg aatgaatgga  1380
agccggcggc acctcgctaa cggattcacc actccaagaa ttggagccaa tcaattcttg  1440
cggagaactg tgaatgcgca aaccaaccct tggcagaaca tatccatcgc gtccgccatc  1500
tccagcagcc gcacgcggcg catctcgggc agcgttgggt cctggccacg ggtgcgcatg  1560
atcgtgctcc tgtcgttgag gacccggcta ggctggcggg gttgccttac tggttagcag  1620
aatgaatcac cgatacgcga gcgaacgtga agcgactgct gctgcaaaac gtctgcgacc  1680
tgagcaacaa catgaatggt cttcggtttc cgtgtttcgt aaagtctgga aacgcggaag  1740
```

```
tcccctacgt gctgctgaag ttgcccgcaa cagagagtgg aaccaaccgg tgataccacg   1800
atactatgac tgagagtcaa cgccatgagc ggcctcattt cttattctga gttacaacag   1860
tccgcaccgc tgtccggtag ctccttccgg tgggcgcggg gcatgactat cgtcgccgca   1920
cttatgactg tcttctttat catgcaactc gtaggacagg tgccggcagc gcccaacagt   1980
cccccggcca cggggcctgc caccataccc acgccgaaac aagcgccctg caccattatg   2040
ttccggatct gcatcgcagg atgctgctgg ctaccctgtg aaacacctac atctgtatta   2100
acgaagcgct aaccgttttt atcaggctct gggaggcaga ataaatgatc atatcgtcaa   2160
ttattacctc cacggggaga gcctgagcaa actggcctca ggcatttgag aagcacacgg   2220
tcacactgct tccggtagtc aataaaccgg taaaccagca atagacataa gcggctattt   2280
aacgaccctg ccctgaaccg acgaccgggt cgaatttgct ttcgaatttc tgccattcat   2340
ccgcttatta tcacttattc aggcgtagca ccaggcgttt aagggcacca ataactgcct   2400 taaaaaatt acgccccgcc ctgccactca tcgcagtact gttgtaattc attaagcatt    2460
ctgccgacat ggaagccatc acagacggca tgatgaacct gaatcgccag cggcatcagc   2520
accttgtcgc cttgcgtata atatttgccc atggtgaaaa cggggggcgaa gaagttgtcc   2580 atattggcca cgtttaaatc aaaactggtg aaactcaccc agggattggc tgagacgaaa   2640
aacatattct caataaaccc tttagggaaa taggccaggt tttcaccgta acacgccaca   2700
tcttgcgaat atatgtgtag aaactgccgg aaatcgtcgt ggtattcact ccagagcgat   2760
gaaaacgttt cagtttgctc atggaaaacg gtgtaacaag ggtgaacact atcccatatc   2820
accagctcac cgtctttcat tgccatacgg aattccggat gagcattcat caggcgggca   2880
agaatgtgaa taaaggccgg ataaaacttg tgcttatttt tctttacggt ctttaaaaag   2940
gccgtaatat ccagctgaac ggtctggtta taggtacatt gagcaactga ctgaaatgcc   3000
tcaaaatgtt ctttacgatg ccattgggat atatcaacgg tggtatatcc agtgatttt    3060 ttctccattt tagcttcctt agctcctgaa aatctcgata actcaaaaaa tacgcccggt   3120
agtgatctta tttcattatg gtgaaagttg gaacctctta cgtgccgatc aacgtctcat   3180
tttcgccaaa agttggccca gggcttcccg gtatcaacag ggacaccagg atttatttat   3240
tctgcgaagt gatcttccgt cacaggtatt tattcggcgc aaagtgcgtc gggtgatgct   3300
gccaacttac tgatttagtg tatgatggtg ttttgaggt gctccagtgg cttctgtttc    3360
tatcagctgt ccctcctgtt cagctactga cggggtggtg cgtaacggca aaagcaccgc   3420
cggacatcag cgctagcgga gtgtatactg gcttactatg ttggcactga tgagggtgtc   3480
agtgaagtgc ttcatgtggc aggagaaaaa aggctgcacc ggtgcgtcag cagaatatgt   3540
gatacaggat atattccgct tcctcgctca ctgactcgct acgctcggtc gttcgactgc   3600
ggcgagcgga aatggcttac gaacggggcg gagatttcct ggaagatgcc aggaagatac   3660
ttaacaggga agtgagaggg ccgcggcaaa gccgtttttc cataggctcc gccccctga    3720 caagcatcac gaaatctgac gctcaaatca gtggtggcga aacccgacag gactataaag   3780
ataccaggcg tttccccctg gcggctccct cgtgcgctct cctgttcctg cctttcggtt   3840
taccggtgtc attccgctgt tatggccgcg tttgtctcat tccacgcctg acactcagtt   3900
ccgggtaggc agttcgctcc aagctggact gtatgcacga accccccgtt cagtccgacc   3960
gctgcgcctt atccggtaac tatcgtcttg agtccaaccc ggaaagacat gcaaaagcac   4020
cactggcagc agccactggt aattgattta gaggagttag tcttgaagtc atgcgccggt   4080
taaggctaaa ctgaaaggac aagttttggt gactgcgctc ctccaagcca gttacctcgg   4140
```
ttcaaagagt tggtagctca gagaaccttc gaaaaaccgc cctgcaaggc ggttttttcg     4200
ttttcagagc aagagattac gcgcagacca aaacgatctc aagaagatca tcttattaat     4260

<210> SEQ ID NO 20
<211> LENGTH: 398
<212> TYPE: PRT
<213> ORGANISM: Artificial Sequence
<220> FEATURE:
<223> OTHER INFORMATION: Amino acid sequence of the alphaGFP::I27::gp1
      fusion protein

<400> SEQUENCE: 20

```
Met Gly Asp Gly Met Gln Val Gln Leu Val Glu Ser Gly Gly Ala Leu
1               5                   10                  15

Val Gln Pro Gly Gly Ser Leu Arg Leu Ser Cys Ala Ala Ser Gly Phe
            20                  25                  30

Pro Val Asn Arg Tyr Ser Met Arg Trp Tyr Arg Gln Ala Pro Gly Lys
        35                  40                  45

Glu Arg Glu Trp Val Ala Gly Met Ser Ser Ala Gly Asp Arg Ser Ser
    50                  55                  60

Tyr Glu Asp Ser Val Lys Gly Arg Phe Thr Ile Ser Arg Asp Asp Ala
65                  70                  75                  80

Arg Asn Thr Val Tyr Leu Gln Met Asn Ser Leu Lys Pro Glu Asp Thr
                85                  90                  95

Ala Val Tyr Tyr Ser Asn Val Asn Val Gly Phe Glu Tyr Trp Gly Gln
            100                 105                 110

Gly Thr Gln Val Thr Val Ser Ser Asn Ser Ser Ser Gln Thr Ser Leu
        115                 120                 125

Ile Glu Val Glu Lys Pro Leu Tyr Gly Val Glu Val Phe Val Gly Glu
    130                 135                 140

Thr Ala His Phe Glu Ile Glu Leu Ser Glu Pro Asp Val His Gly Gln
145                 150                 155                 160

Trp Lys Leu Lys Gly Gln Pro Leu Thr Ala Ser Pro Asp Cys Glu Ile
                165                 170                 175

Ile Glu Asp Gly Lys Lys His Ile Leu Ile Leu His Asn Cys Gln Leu
            180                 185                 190

Gly Met Thr Gly Glu Val Ser Phe Gln Ala Ala Asn Ala Lys Ser Ala
        195                 200                 205

Ala Asn Leu Lys Val Lys Glu Leu Asn Ser Ser Asp Tyr Lys Asp
    210                 215                 220

Asp Asp Asp Lys Gly Asn Gly Thr Leu Ile Ile Pro Arg Lys Glu Ala
225                 230                 235                 240

Pro Val Ser Gly Glu Gly Thr Val Val Ile Pro Gln Pro Ala Gly Asp
                245                 250                 255

Glu Pro Val Ile Lys Asn Thr Phe Phe Phe Pro Asp Ile Asp Pro Lys
            260                 265                 270

Arg Val Arg Glu Arg Met Arg Leu Glu Gln Thr Val Ala Pro Ala Arg
        275                 280                 285

Leu Arg Glu Ala Ile Lys Ser Gly Met Ala Glu Thr Asn Ala Glu Leu
    290                 295                 300

Tyr Glu Tyr Arg Glu Gln Lys Ile Ala Ala Gly Phe Thr Arg Leu Ala
305                 310                 315                 320

Asp Val Pro Ala Asp Asp Ile Asp Gly Glu Ser Ile Lys Val Phe Tyr
                325                 330                 335
```

```
Tyr Glu Arg Ala Val Cys Ala Met Ala Thr Ala Ser Leu Tyr Glu Arg
                340                 345                 350

Tyr Arg Gly Val Asp Ala Ser Ala Lys Gly Asp Lys Lys Ala Asp Ser
            355                 360                 365

Ile Asp Ser Thr Ile Asp Glu Leu Trp Arg Asp Met Arg Trp Ala Val
370                 375                 380

Ala Arg Ile Gln Gly Lys Pro Arg Cys Ile Val Ser Gln Ile
385                 390                 395

<210> SEQ ID NO 21
<211> LENGTH: 403
<212> TYPE: PRT
<213> ORGANISM: Artificial Sequence
<220> FEATURE:
<223> OTHER INFORMATION: Amino acid sequence of the gp1::alphaGFP::I27
      fusion protein

<400> SEQUENCE: 21

Met Met Thr Leu Ile Ile Pro Arg Lys Glu Ala Pro Val Ser Gly Glu
1               5                   10                  15

Gly Thr Val Val Ile Pro Gln Pro Ala Gly Asp Glu Pro Val Ile Lys
            20                  25                  30

Asn Thr Phe Phe Pro Asp Ile Asp Pro Lys Arg Val Arg Glu Arg
        35                  40                  45

Met Arg Leu Glu Gln Thr Val Ala Pro Ala Arg Leu Arg Glu Ala Ile
50                  55                  60

Lys Ser Gly Met Ala Glu Thr Asn Ala Glu Leu Tyr Glu Tyr Arg Glu
65                  70                  75                  80

Gln Lys Ile Ala Ala Gly Phe Thr Arg Leu Ala Asp Val Pro Ala Asp
                85                  90                  95

Asp Ile Asp Gly Glu Ser Ile Lys Val Phe Tyr Tyr Glu Arg Ala Val
            100                 105                 110

Cys Ala Met Ala Thr Ala Ser Leu Tyr Glu Arg Tyr Arg Gly Val Asp
            115                 120                 125

Ala Ser Ala Lys Gly Asp Lys Lys Ala Asp Ser Ile Asp Ser Thr Ile
130                 135                 140

Asp Glu Leu Trp Arg Asp Met Arg Trp Ala Val Ala Arg Ile Gln Gly
145                 150                 155                 160

Lys Pro Arg Cys Ile Val Ser Gln Ile Gly Gly Gly Ser Ser Arg Met
                165                 170                 175

Gly Asp Gly Met Gln Val Gln Leu Val Glu Ser Gly Gly Ala Leu Val
            180                 185                 190

Gln Pro Gly Gly Ser Leu Arg Leu Ser Cys Ala Ala Ser Gly Phe Pro
        195                 200                 205

Val Asn Arg Tyr Ser Met Arg Trp Tyr Arg Gln Ala Pro Gly Lys Glu
210                 215                 220

Arg Glu Trp Val Ala Gly Met Ser Ser Ala Gly Asp Arg Ser Ser Tyr
225                 230                 235                 240

Glu Asp Ser Val Lys Gly Arg Phe Thr Ile Ser Arg Asp Asp Ala Arg
            245                 250                 255

Asn Thr Val Tyr Leu Gln Met Asn Ser Leu Lys Pro Glu Asp Thr Ala
        260                 265                 270

Val Tyr Tyr Ser Asn Val Asn Val Gly Phe Glu Tyr Trp Gly Gln Gly
            275                 280                 285

Thr Gln Val Thr Val Ser Ser Asn Ser Ser Ser Gln Ser Leu Ile
290                 295                 300
```

```
Glu Val Glu Lys Pro Leu Tyr Gly Val Glu Val Phe Val Gly Glu Thr
305                 310                 315                 320

Ala His Phe Glu Ile Glu Leu Ser Glu Pro Asp Val His Gly Gln Trp
                325                 330                 335

Lys Leu Lys Gly Gln Pro Leu Thr Ala Ser Pro Asp Cys Glu Ile Ile
                340                 345                 350

Glu Asp Gly Lys Lys His Ile Leu Ile Leu His Asn Cys Gln Leu Gly
                355                 360                 365

Met Thr Gly Glu Val Ser Phe Gln Ala Ala Asn Ala Lys Ser Ala Ala
                370                 375                 380

Asn Leu Lys Val Lys Glu Leu Asn Ser Ser Ser Asp Tyr Lys Asp Asp
385                 390                 395                 400

Asp Asp Lys

<210> SEQ ID NO 22
<211> LENGTH: 5230
<212> TYPE: DNA
<213> ORGANISM: Artificial Sequence
<220> FEATURE:
<223> OTHER INFORMATION: Nucleotide sequence of the alphaGFP::I27::gp1
      fusion protein expression vector

<400> SEQUENCE: 22 ggttttttcgc cctttgacgt tggagtccac gttctttaat agtggactct tgttccaaac      60
tggaacaaca ctcaaccccta tctcggtcta ttcttttgat ttataaggga ttttgccgat     120
ttcggcctat tggttaaaaa atgagctgat ttaacaaaaa tttaacgcga atttttaacaa     180 aatattaacg cttacaattt aggtggcact tttcggggaa atgtgcgcgg aaccccctatt     240 tgttatttt tctaaataca ttcaaatatg tatccgctca tgagacaata accctgataa      300
atgcttcaat aatattgaaa aaggaagagt atgagtattc aacatttccg tgtcgccctt     360
attccctttt ttgcggcatt ttgccttcct gtttttgctc acccagaaac gctggtgaaa     420
gtaaaagatg ctgaagatca gttgggtgca cgagtgggtt acatcgaact ggatctcaac     480
agcggtaaga tccttgagag ttttcgcccc gaagaacgtt ttccaatgat gagcactttt     540
aaagttctgc tatgtggcgc ggtattatcc cgtattgacg ccgggcaaga gcaactcggt     600
cgccgcatac actattctca gaatgacttg gttgagtact caccagtcac agaaaagcat     660
cttacggatg gcatgacagt aagagaatta tgcagtgctg ccataaccat gagtgataac     720
actgcggcca acttacttct gacaacgatc ggaggaccga aggagctaac cgcttttttg     780
cacaacatgg ggatcatgt aactcgcctt gatcgttggg aaccggagct gaatgaagcc     840
ataccaaacg acgagcgtga caccacgatg cctgtagcaa tggcaacaac gttgcgcaaa     900
ctattaactg gcgaactact tactctagct tcccggcaac aattaataga ctggatggag     960
gcggataaag ttgcaggacc acttctgcgc tcggcccttc cggctggctg gtttattgct    1020
gataaatctg gagccggtga gcgtgggtct cgcggtatca ttgcagcact ggggccagat    1080
ggtaagccct cccgtatcgt agttatctac acgacgggga gtcaggcaac tatggatgaa    1140
cgaaatagac agatcgctga gataggtgcc tcactgatta agcattggta actgtcagac    1200
caagtttact catatatact ttagattgat ttaaaacttc attttttaatt taaaaggatc    1260 taggtgaaga tccttttttga taatctcatg accaaaatcc cttaacgtga gttttcgttc    1320
cactgagcgt cagaccccgt agaaaagatc aaaggatctt cttgagatcc ttttttttctg    1380 cgcgtaatct gctgcttgca aacaaaaaaa ccaccgctac cagcggtggt ttgtttgccg    1440
```

```
gatcaagagc taccaactct tttccgaag gtaactggct tcagcagagc gcagatacca    1500
aatactgtcc ttctagtgta gccgtagtta ggccaccact tcaagaactc tgtagcaccg    1560
cctacatacc ccgctctgct aatcctgtta ccagtggctg ctgccagtgg cgataagtcg    1620
tgtcttaccg ggttggactc aagacgatag ttaccggata aggcgcagcg gtcgggctga    1680 acgggggggtt cgtgcacaca gcccagcttg gagcgaacga cctacaccga actgagatac    1740
ctacagcgtg agctatgcga aagcgccacg cttcccgaag ggagaaaggc ggacaggtat    1800
ccggtaagcg gcagggtcgg agcaggagag cgcacgaggg agcttccagg gggaaacgcc    1860
tggtatcttt atagtcctgt cgggtttcgc cacctctgac ttgagcgtcg attttttgtga   1920 tgctcgtcag gggggcggag cctatggaaa aacgccagca acgcggcctt tttacggttc    1980
ctggcctttt gctggccttt tgctcacatg ttctttcctg cgttatcccc tgattctgtg    2040
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160
gcgcgtggcc gttcattaat gcagctggca cgacaggttt cccgactgcg gccgcgacac    2220
ggaaatgttg aatactcata ctcttccttt ttcaatatta ttgaagcatt tatcagggtt    2280
attgtctcat gagcggatac atatttgaat gtatttagaa aaataaacaa ataggggttc    2340
cgcgcacatt tccccgaaaa gtgccacctg catcgattta ttatgacaac ttgacggcta    2400
catcattcac ttttctttca caaccggcac ggaactcgct cgggctggcc ccggtgcatt    2460
ttttaaatac ccgcgagaaa tagagttgat cgtcaaaacc aacattgcga ccgacggtgg    2520
cgataggcat ccgggtggtg ctcaaaagca gcttcgcctg gctgatacgt tggtcctcgc    2580
gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat gcgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga aagaaccccg tattggcaaa tattgacggc cagttaagcc    2940
attcatgcca gtaggcgcgc ggacgaaagt aaacccactg gtgataccat tcgcgagcct    3000
ccggatgacg accgtagtga tgaatctctc ctggcgggaa cagcaaaata tcacccggtc    3060
ggcaaacaaa ttctcgtccc tgatttttca ccaccccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
aatgggagac ggcatgcaag tgcagctggt tgagagtggt ggagcactgg ttcagccagg    3660
tggaagcctt cgtctgtcat gcgcagcgtc tggattcccg gttaatcgct actcaatgcg    3720
ctggtatcgg caggcaccgg gtaaagaacg ggaatgggtt gccggtatgt caagcgcagg    3780
cgatcgcagt tcgtatgaag attctgttaa aggccgtttc accatttcgc gtgatgacgc    3840
```

```
acgcaacacg gtttacctcc agatgaactc gcttaaaccg aagacaccg cggtttatta      3900 cagcaacgtg aacgttggct ttgaatattg gggccaggga acccaagtga ctgtgagctc     3960
aaacagctcg tctcagacca gcctgattga agttgaaaaa ccgttgtacg gcgtggaggt     4020
gttcgtcggc gagactgccc acttcgaaat tgaactgagc gaaccggacg ttcatggtca     4080
gtggaagctg aagggtcagc cgctgaccgc gagcccggac tgcgagatca tcgaggatgg     4140
taagaagcat attctgatcc tgcacaattg tcagctgggt atgaccggcg aggtcagctt     4200
tcaagctgcg aacgcaaaaa gcgcagcgaa tttgaaagtt aaagagctga actcgagcag     4260
cgattacaag gacgatgatg acaaaggcaa cggaacgctg attattccgc gaaaggaggc     4320
tcccgtgtcc ggtgagggta cggtggtcat cccgcaaccg gcaggcgacg agccggtgat     4380
taaaaacacg ttctttttc ccgatatcga cccgaagcgc gtccgggaac gtatgcgcct     4440
tgagcagacc gtcgcccccg cccgtctgcg tgaggccatc aagtcaggca tggctgaaac     4500
gaatgcggag ctgtacgagt accgcgaaca gaaaattgcc gccggtttta cgcgtctggc     4560
tgacgtcccg gcgacgata tcgacggtga agcatcaag gttttttact acgagcgcgc      4620
cgtgtgtgcg atggcgaccg cgtcgcttta tgagcgttat cgcggtgtgg atgccagtgc     4680
gaaaggcgac aagaaggctg acagcattga cagcaccatt gatgagctgt ggcgggatat     4740
gcgctgggcg gtggcgcgca tccagggcaa gccgcgctgc atcgtgagtc aaatctaagc     4800
ttgaattcgc gcgctcactg gccgtcgttt tacaacgtcg tgactgggaa accctggcg      4860 ttacccaact taatcgcctt gcagcacatc cccctttcgc cagctggcgt aatagcgaag     4920
aggcccgcac cgatcgccct tcccaacagt tgcgcagcct gaatggcgaa tgggacgcgc     4980
cctgtagcgg cgcattaagc gcggcgggtg tggtggttac gcgcagcgtg accgctacac     5040
ttgccagcgc cctagcgccc gctcctttcg ctttcttccc ttcctttctc gccacgttcg     5100 ccggcttcc ccgtcaagct ctaaatcggg ggctccctt agggttccga tttagtgctt      5160
tacggcacct cgaccccaaa aaacttgatt agggtgatgg ttcacgtagt gggccatcgc     5220
cctgatagac                                                           5230
```

<210> SEQ ID NO 23
<211> LENGTH: 318
<212> TYPE: DNA
<213> ORGANISM: Artificial Sequence
<220> FEATURE:
<223> OTHER INFORMATION: Nucleotide sequence of the lambda holin gene

<400> SEQUENCE: 23

```
atgccagaaa acatgacct gttggccgcc attctcgcgg caaaggaaca aggcatcggg        60
gcaatccttg cgtttgcaat ggcgtacctt cgcggcagat ataatggcgg tgcgtttaca      120
aaaacagtaa tcgacgcaac gatgtgcgcc attatcgcct ggttcattcg tgaccttctc     180
gacttcgccg gactaagtag caatctcgct tatataacga gcgtgtttat cggctacatc     240
ggtactgact cgattggttc gcttatcaaa cgcttcgctg ctaaaaaagc cggagtagaa     300
gatggtagaa atcaataa                                                  318
```

<210> SEQ ID NO 24
<211> LENGTH: 477
<212> TYPE: DNA
<213> ORGANISM: Artificial Sequence
<220> FEATURE:
<223> OTHER INFORMATION: Nucleotide sequence of the lambda phage
      lysozyme gene

<400> SEQUENCE: 24

```
atggtagaaa tcaataatca acgtaaggcg ttcctcgata tgctggcgtg gtcggaggga      60
actgataacg gacgtcagaa accagaaat catggttatg acgtcattgt aggcggagag     120
ctatttactg attactccga tcaccctcgc aaacttgtca cgctaaaccc aaaactcaaa     180
tcaacaggcg ccggacgcta ccagcttctt tcccgttggt gggatgccta ccgcaagcag     240
cttggcctga agacttctc tccgaaaagt caggacgctg tggcattgca gcagattaag     300
gagcgtggcg ctttacctat gattgatcgt ggtgatatcc gtcaggcaat cgaccgttgc     360
agcaatatct gggcttcact gccgggcgct ggttatggtc agttcgagca taaggctgac     420
agcctgattg caaaattcaa agaagcgggc ggaacggtca gagagattga tgtatga       477
```

<210> SEQ ID NO 25
<211> LENGTH: 20
<212> TYPE: PRT
<213> ORGANISM: Artificial Sequence
<220> FEATURE:
<223> OTHER INFORMATION: Amino acid sequence of lambda lysis cluster
      deletion remnant

<400> SEQUENCE: 25

```
Met Lys Met Pro Glu Lys Gln Leu Glu Gly Thr Gln Lys Tyr Ile Asn
1               5                   10                  15

Glu Gln Cys Arg
            20
```

<210> SEQ ID NO 26
<211> LENGTH: 401
<212> TYPE: DNA
<213> ORGANISM: Artificial Sequence
<220> FEATURE:
<223> OTHER INFORMATION: Nucleotide sequence of the lambda cos region

<400> SEQUENCE: 26

```
cttccattgt tcattccacg gacaaaaaca gagaaaggaa acgacagagg ccaaaaagct      60
cgctttcagc acctgtcgtt tcctttcttt tcagagggta ttttaaataa aaacattaag     120
ttatgacgaa gaagaacgga aacgccttaa accggaaaat tttcataaat agcgaaaacc     180
cgcgaggtcg ccgccccgta acctgtcgga tcaccggaaa ggacccgtaa agtgataatg     240
attatcatct acatatcaca acgtgcgtgg aggccatcaa accacgtcaa ataatcaatt     300
atgacgcagg tatcgtatta attgatctgc atcaacttaa cgtaaaaaca acttcagaca     360
atacaaatca gcgacactga atacggggca acctcatgtc c                         401
```

<210> SEQ ID NO 27
<211> LENGTH: 4019
<212> TYPE: DNA
<213> ORGANISM: Artificial Sequence
<220> FEATURE:
<223> OTHER INFORMATION: Nucleotide sequence of the lambda SR deletion
      vector

<400> SEQUENCE: 27

```
tcgcgcgttt cggtgatgac ggtgaaaacc tctgacacat gcagctcccg gagacggtca      60
cagcttgtct gtaagcggat gccggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagtctag     240
accaagctat ttaggtgaca ctatagaaag cggccgcgaa ttcctcgagc tgcagtggcc     300
```

```
aacgtggcct gaatgcctta agagcattga gtcgataatc gtgaagagtc ggcgagcctg    360
gttagccagt gctctttccg ttgtgctgaa ttaagcgaat accggaagca gaaccggatc    420
accaaatgcg tacaggcgtc atcgccgccc agcaacagca caacccaaac tgagccgtag    480
ccactgtctg tcctgaattc attagtaata gttacgctgc ggccttttac acatgacctt    540
cgtgaaagcg ggtggcagga ggtcgcgcta acaacctcct gccgttttgc ccgtgcatat    600
cggtcacgaa caaatctgat tactaaacac agtagcctgg atttgttcta tcagtaatcg    660
accttattcc taattaaata gagcaaatcc ccttattggg ggtaagacat gaagatgcca    720
gaaaaacaac tggaaggaac ccagaagtat attaatgagc agtgcagata gagttgccca    780
tatcgatggg caactcatgc aattattgtg agcattagaa gaactcgtca agaaggcgat    840
agaaggcgat gcgctgcgaa tcgggagcgg cgataccgta aagcacgagg aagcggtcag    900
cccattcgcc gccaagctct tcagcaatat cacgggtagc caacgctatg tcctgatagc    960
ggtccgccac acccagccgg ccacagtcga tgaatccaga aaagcggcca ttttccacca   1020
tgatattcgg caagcaggca tcgccatggg tcacgacgag atcctcgccg tcgggcatgc   1080
gcgccttgag cctggcgaac agttcggctg cgcgagccc ctgatgctct tcgtccagat   1140
catcctgatc gacaagaccg gcttccatcc gagtacgtgc tcgctcgatg cgatgtttcg   1200
cttggtggtc gaatgggcag gtagccggat caagcgtatg cagccgccgc attgcatcag   1260
ccatgatgga tactttctcg gcaggagcaa ggtgagatga caggagatcc tgccccggca   1320
cttcgcccaa tagcagccag tcccttcccg cttcagtgac aacgtcgagc acagctgcgc   1380
aaggaacgcc cgtcgtggcc agccacgata gccgcgctgc ctcgtcctgc agttcattca   1440
gggcaccgga caggtcggtc ttgacaaaaa gaaccgggcg ccctgcgct gacagccgga   1500
acacggcggc atcagagcag ccgattgtct gttgtgccca gtcatagccg aatagcctct   1560
ccacccaagc ggccggagaa cctgcgtgca atccatcttg ttcaatcatg gtgttattcc   1620
cgatgctttt tgaagttcgc agaatcgtat gtgtagaaaa ttaaacaaac cctaaacaat   1680
gagttgaaat ttcatattgt taatatttat taatgtatgt caggtgcgat gaatcgtcat   1740
tgtattcccg gattaactat gtccacagcc ctgacgggga acttctctgc gggagtgtcc   1800
gggaataatt aaaacgatgc acacagggtt tagcgcgtac acgtattgca ttatgccaac   1860
gccccggtgc tgacacggaa gaaaccggac gttatgattt agcgtggaaa gatttgtgta   1920
gtgttctgaa tgctctcagt aaatagtaat gaattatcaa aggtatagta atatctttta   1980
tgttcatgga tatttgtaac ccatcggaaa ggcattctgg cctctcaggc ctggtaccga   2040
agcttggatc cggcgcgccg ccctatagtg agtcgtatta cgagctccaa aggcggtaat   2100
acggttatcc acagaatcag gggataacgc aggaaagaac atgtgagcaa aaggccagca   2160
aaaggccagg aaccgtaaaa aggccgcgtt gctggcgttt ttccataggc tccgcccccc   2220
tgacgagcat cacaaaaatc gacgctcaag tcagaggtgg cgaaacccga caggactata   2280
aagataccag gcgtttcccc ctggaagctc cctcgtgcgc tctcctgttc cgaccctgcc   2340
gcttaccgga tacctgtccg cctttctccc ttcgggaagc gtggcgcttt ctcatagctc   2400
acgctgtagg tatctcagtt cggtgtaggt cgttcgctcc aagctgggct gtgtgcacga   2460
accccccgtt cagcccgacc gctgcgcctt atccggtaac tatcgtcttg agtccaaccc   2520
ggtaagacac gacttatcgc cactggcagc agccactggt aacaggatta gcagagcgag   2580
gtatgtaggc ggtgctacag agttcttgaa gtggtggcct aactacggct acactagaag   2640
gacagtattt ggtatctgcg ctctgctgaa gccagttacc ttcggaaaaa gagttggtag   2700
```

```
ctcttgatcc ggcaaacaaa ccaccgctgg tagcggtggt ttttttgttt gcaagcagca    2760
gattacgcgc agaaaaaaag gatctcaaga agatcctttg atcttttcta cggggtctga    2820
cgctcagtgg aacgaaaact cacgttaagg gattttggtc atgagattat caaaaaggat    2880
cttcacctag atccttttaa attaaaaatg aagtttttaaa tcaatctaaa gtatatatga    2940
gtaaacttgg tctgacagtt accaatgctt aatcagtgag gcacctatct cagcgatctg    3000
tctatttcgt tcatccatag ttgcctgact ccccgtcgtg tagataacta cgatacggga    3060
gggcttacca tctggcccca gtgctgcaat gataccgcga gacccacgct caccggctcc    3120
agatttatca gcaataaacc agccagccgg aagggccgag cgcagaagtg gtcctgcaac    3180
tttatccgcc tccatccagt ctattaattg ttgccgggaa gctagagtaa gtagttcgcc    3240
agttaatagt ttgcgcaacg ttgttgccat tgctacaggc atcgtggtgt cacgctcgtc    3300
gtttggtatg gcttcattca gctccggttc ccaacgatca aggcgagtta catgatcccc    3360
catgttgtgc aaaaaagcgg ttagctcctt cggtcctccg atcgttgtca gaagtaagtt    3420
ggccgcagtg ttatcactca tggttatggc agcactgcat aattctctta ctgtcatgcc    3480
atccgtaaga tgcttttctg tgactggtga gtactcaacc aagtcattct gagaatagtg    3540
tatgcggcga ccgagttgct cttgcccggc gtcaatacgg gataataccg cgccacatag    3600
cagaacttta aaagtgctca tcattggaaa acgttcttcg gggcgaaaac tctcaaggat    3660
cttaccgctg ttgagatcca gttcgatgta acccactcgt gcacccaact gatcttcagc    3720
atcttttact ttcaccagcg tttctgggtg agcaaaaaca ggaaggcaaa atgccgcaaa    3780
aaagggaata agggcgacac ggaaatgttg aatactcata ctcttccttt ttcaatatta    3840
ttgaagcatt tatcagggtt attgtctcat gagcggatac atatttgaat gtatttagaa    3900
aaataaacaa atagggggttc cgcgcacatt tccccgaaaa gtgccacctg acgtctaaga    3960
aaccattatt atcatgacat taacctataa aataggcgt atcacgaggc cctttcgtc     4019
```